US009347945B2

(12) United States Patent
Colpitts et al.

(10) Patent No.: US 9,347,945 B2
(45) Date of Patent: *May 24, 2016

(54) METHODS AND MARKER COMBINATIONS FOR SCREENING FOR PREDISPOSITION TO LUNG CANCER

(75) Inventors: Tracey Colpitts, Round Lake, IL (US); Eric L. Russell, Gurnee, IL (US); Stephen Frost, Gurnee, IL (US); Javier Ramirez, Gurnee, IL (US); Bhawani Singh, Wilmette, IL (US); John C. Russell, Kenosha, WI (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/771,727

(22) Filed: Jun. 29, 2007

(65) Prior Publication Data

US 2008/0160546 A1    Jul. 3, 2008

Related U.S. Application Data

(63) Continuation-in-part of application No. 11/644,365, filed on Dec. 21, 2006, now abandoned.

(60) Provisional application No. 60/753,331, filed on Dec. 22, 2005.

(51) Int. Cl.
*G01N 33/53* (2006.01)
*G01N 33/574* (2006.01)
*C07K 14/47* (2006.01)

(52) U.S. Cl.
CPC ...... *G01N 33/57423* (2013.01); *C07K 14/4738* (2013.01); *G01N 2333/4703* (2013.01); *G01N 2333/4725* (2013.01); *G01N 2333/4742* (2013.01); *G01N 2333/705* (2013.01); *G01N 2333/70596* (2013.01); *G01N 2333/775* (2013.01); *G01N 2333/8125* (2013.01)

(58) Field of Classification Search
CPC ............... G01N 2800/60; G01N 33/57423; G06F 19/10; G06F 19/24; G06F 19/707
See application file for complete search history.

(56) References Cited

U.S. PATENT DOCUMENTS

| | | | |
|---|---|---|---|
| 5,719,060 A | | 2/1998 | Hutchens et al. |
| 5,770,385 A | * | 6/1998 | Yamaguchi et al. ............ 435/7.9 |
| 6,251,603 B1 | * | 6/2001 | Jager et al. ..................... 435/6 |
| 2003/0003454 A1 | * | 1/2003 | Livneh et al. .................. 435/6 |
| 2003/0078370 A1 | | 4/2003 | Coats et al. |
| 2003/0104499 A1 | | 6/2003 | Pressman et al. |
| 2003/0198316 A1 | | 10/2003 | Dewaele et al. |
| 2004/0203083 A1 | * | 10/2004 | Buechler et al. ............... 435/7.92 |
| 2006/0003465 A1 | | 1/2006 | Zhukov et al. |
| 2006/0211019 A1 | | 9/2006 | Halling et al. |
| 2006/0223127 A1 | * | 10/2006 | Yip et al. ....................... 435/7.23 |
| 2007/0065888 A1 | | 3/2007 | Ring et al. |
| 2007/0178504 A1 | | 8/2007 | Colpitts et al. |
| 2008/0160546 A1 | | 7/2008 | Colpitts et al. |

FOREIGN PATENT DOCUMENTS

| | | |
|---|---|---|
| JP | 2003521669 A | 7/2003 |
| JP | 2003240774 | 8/2003 |
| WO | 0058728 A1 | 10/2000 |
| WO | 03/080640 | 10/2003 |
| WO | 2004061410 A2 | 7/2004 |
| WO | 2004090550 A2 | 10/2004 |
| WO | 2005017523 A2 | 2/2005 |
| WO | 2005090603 A2 | 9/2005 |
| WO | 2006010047 A2 | 1/2006 |
| WO | WO-2006010047 A2 | 1/2006 |
| WO | 2006126008 A2 | 11/2006 |
| WO | 2007076439 A2 | 7/2007 |

OTHER PUBLICATIONS

Maeda et al., Internal Medicine, 1996, 35(10): 764-771.*
Lubin et al., Nat. Med., 1995, 1(7): 701-2.*
Bondarenko, et al. Journal of Lipid Research, vol. 40 (1999) pp. 543-555.
Duda, et al. In Pattern Classifications Second Edition (Wiley-Interscience 2001) pp. 485.
Menon, et al. Journal Clinical Oncology, vol. 23, No. 31 (Nov. 1, 2005), pp. 7919-7926.
Mor, PNAS, vol. 102, No. 21 (May 24, 2005), pp. 7677-7682.
Ottenbacher, et al. Journal of Clinical Epidemiology, vol. 57 (2007), pp. 1147-1152.
Pepe, The Statistical Evaluation of Medical Tests for Classification and Prediction (New York, Oxford University Press, 2003), pp. 178-187.
Sackett, et al. Clinical Epidemiology, (Boston/Toronto, Little, Brown and Company, 1985), pp. 100-108.
Skates, et al. Journal Clinical Oncology, vol. 22, No. 20 (Oct. 15, 2004), pp. 4059-4066.
Skates, et al. Journal Clinical Oncology, vol. Supplemental 21, No. 10 (May 15, 2003), pp. 206-210.
Stephan, Cancer letters, vol. 249 (2007), pp. 18-29.
Wan, J. Am. Soc. Mass Spectrom, vol. 13 (2002), pp. 85-88.
Meyer and Miller "CABIOS", vol. 4 (1989), pp. 11-17.
Kutteh, W. et al., "Multiples of the Median: An Alternative Method for Reporting Antiphospholipid Antibodies in Women With Recurrent Pregnancy Loss", Obstetrics & Gynecology, vol. 84, No. 5, 811-815 (1994).
Palomaki et al., "Using Multiples of the Median to Normalize Serum Protein Measurements", Clin Chem Lab Med 2001; 39(11):1137-1145.
Strausberg, S.L. et al. CCNE2 protein [*Homo sapiens*]. GenBank Accession No. AAH07015. Sep. 16, 2005.
Gudas, J.M. et al. "Cyclin E2, a Novel G1 Cyclin That Binds Cdk2 and is Aberrantly Expressed in Human Cancers", Mol. Cell. Biol., Jan. 1999, vol. 19, No. 1, pp. 612-622.

(Continued)

*Primary Examiner* — Hong Sang
(74) *Attorney, Agent, or Firm* — Lisa V. Mueller; Michael Best & Friedrich LLP

(57) ABSTRACT

The present invention relates to rapid, sensitive methods for determining whether a subject is at risk of developing lung cancer or has lung cancer based on certain combinations or biomarkers or biomarkers and biometric parameters.

12 Claims, 11 Drawing Sheets

(56) References Cited

OTHER PUBLICATIONS

Lee, J.H. et al., Cancer Patients With Effusions From Primary Lung Enolase, and Cytokeratin 19 Fragments in Carcinoembryonic Antigen, Neuron-Specific Diagnostic Utility of Serum and Pleural Fluid. Chest. Oct. 2005, vol. 128, No. 4, pp. 2298-2303.
Lai, C.-L. et al., Presence of Serum Anti-p53 Antibodies is Associated with Pleural Effusion and Poor Prognosis in Lung Cancer Pateients. Clin. Cancer Res. Dec. 1993, vol. 4, pp. 3025-3030.
International Search Report issued in PCT/US06/62488 mailed Jul. 18, 2007.
Written Opinion issued in PCT/US06/62488 mailed Jul. 18, 2007.
"European Search Report of EP Patent Application No. EP06840341, dated Jun. 24, 2009, 2 pages total.,".
Brechot J. M. et al., "Diagnostic and Prognostic Value of Cyfra 21-I Compared with Other Tumour Markers in Patients with Non-small Cell Lung Cancer: A Prospective Study of 116 Patients," European Journal of Cancer, 1997, pp. 385-391, vol. 33 (3), Pergamonpress, Oxford, GB.
Cioffi M. et al., "Serum anti-p53 antibodies in lung cancer: comparison with established tumor markers," Lung Cancer, 2001, pp. 163-169, vol. 33 (2-3).
International Search Report for application No. PCT/US2008/068625, Mailed on Dec. 24, 2008, 4 pages.
Kalabay L. et al., "Human serum fetuin A/alpha2HS-glycoprotein level is associated with long-term survival in patients with alcoholic liver cirrhosis, comparison with the Child-Pugh and MELD scores," BMC Gastroenterol, 2007, pp. 1-9, vol. 7(15), Biomed Central Ltd., London, GB.
PCT International Application No. PCT/US2008/068462, Search Report and Written Opinion of the International Searching Authority Mailed on Oct. 10, 2008.
Sadler D.W. et al., "Post mortem markers of chronic alcoholism," Forensic Sci Int, 1996, pp. 153-163, vol. 82 (2).
Sangrajrang Suleporn et al., "Serum p53 antibodies in patients with lung cancer:correlation with clinicopathologic features and smoking," Lung Cancer, 2003, pp. 297-301, vol. 39 (3).
Bialek E., et al., "Alpha 1-Antitrypsin (alpha 1-proteinase inhibitor) Concentration in the Patients with Neoplastic Disease," Materia Medica Polana, 1988, vol. 20 (3), pp. 180-183.
Chaffin P., et al., "Part 1. Bronchogenic Carcinoma a Review and Study," The Nurse Practitioner, 1981, vol. 6 (1), Abstract.
Charokopos N., et al., "Increased Levels of Albumin in Bronchial Washing Fluid of Patients with Bronchial Carcinoma. Could Albumin be Considered as a Tumor Marker?," The International Journal of Biological Markers, 2004, vol. 19 (4), pp. 316-321.
Daddi G., et al., "Alfa-Antitrypsin Increase in Lung Cancer," Boll Ist Sieroter Milan., 1976, vol. 55 (6), pp. 510-512.
Etzioni R., et al., "The Case for Early Detection," Nature Reviews Cancer, 2003, vol. 3 (4), pp. 243-252.
European Search Report for Application No. EP11178834, mailed on Oct. 24, 2011, 2 pages.
Examination Report for Application No. EP08781113.9, mailed on Dec. 5, 2012, 4 pages.
Extended European Search Report for Application No. EP12156879.4, mailed on Oct. 24, 2012, 29 pages.
Gao W.M., et al., "Distinctive Serum Protein Profiles Involving Abundant Proteins in Lung Cancer Patients based upon Antibody Microarray Analysis," BMC Cancer, 2005, vol. 5 (1), pp. 110.
Harris C.C., et al., "Elevated Alpha1-Antitrypsin Serum Levels in Lung Cancer Patients," Cancer, 1974, vol. 34 (2), pp. 280-281.
Howard B.A., et al., "Identification and Validation of a Potential Lung Cancer Serum Biomarker Detected by Matrix-Assisted Laser Desorption/ionization—Time of Flight Spectra Analysis," Proteomics, 2003, vol. 3 (9), pp. 1720-1724.
International Preliminary Report on Patentability and Written Opinion for Application No. PCT/US2008/068625, mailed on Jan. 5, 2010, 7 pages.
International Preliminary Report on Patentability for Application No. PCT/US2006/062488, mailed on Jun. 24, 2008, 1 page.
Khan N., et al., "Clinical Utility of Serum Amyloid A and Macrophage Migration Inhibitory Factor as Serum Biomarkers for the Detection of Nonsmall Cell Lung Carcinoma," Cancer, 2004, vol. 101 (2), 2004, pp. 379-384.
Mercer D.W., "Use of Multiple Markers to Enhance Clinical Utility," Immunology Series, 1990, vol. 53, pp. 39-54.
Nash D.R., et al., "Pretreatment, Prediagnosis Immunoglobulin, and Alpha 1-Antitrypsin Levels in Patients with Bronchial Carcinoma," Journal of the National Cancer Institute, 1980, vol. 64 (4), pp. 721-724.
Non-Final Office Action mailed Apr. 4, 2013 for U.S. Appl. No. 12/667,069, filed Feb. 14, 2011.
Pollan M., et al., "Clinical Value of p53, c-erbB-2, CEA and CA125 Regarding Relapse, Metastasis and Death in Resectable Non-Small Cell Lung Cancer," International Journal of Cancer, 2003, vol. 107 (5), pp. 781-790.
Shi G.L., et al., "The Value of Serum Tumor Marker in the Diagnosis of Lung Cancer," Chinese Journal of Oncology, 2005, vol. 27 (5), pp. 299-301.
Supplementary European Search Report for Application No. EP08781113, mailed on Jun. 15, 2010, 2 pages.
Wu C., et al., "Relationship between the Expression of Alpha 1-Antitrypsinase in Bronchioalveolar Carcinoma and Clinical Pathology," Journal of Tongji Medical University, 2000, vol. 20 (1), pp. 26-28.
Zimmerman L., et al., "Truncation forms of Serum Amyloid A Contribute to a Serum Proteomic Signature of Lung Cancer," American Association for Cancer Research, 2005, vol. 46, pp. 1133.
Office Action mailed May 10, 2013 for European Application No. 11178834.5 filed Jun. 27, 2008.
Non-Final Office Action mailed May 1, 2014 for U.S. Appl. No. 12/667,069, filed Feb. 14, 2011.
Tockman M.S., et al., "Considerations in Bringing a Cancer Biomarker to Clinical Application," Cancer Research, 1992, vol. 52 (9 Suppl), pp. 2711s-2718s.
Extended European Search Report for Application No. EP13166996.2, mailed on Sep. 13, 2013, 6 pages.
Lee L., et al., "NY-ESO-1 may be a Potential Target for Lung Cancer Immunotherapy," The Cancer Journal from Scientific American, 1999, vol. 5 (1), pp. 20-25.
Office Action mailed Jan. 3, 2014 for European Application No. 12156879.4 filed Dec. 21, 2006.
Office Action mailed Aug. 16, 2013 for European Application No. 06840341.9 filed Dec. 21, 2006.
Zhong L., et al., "Identification of Circulating Antibodies to Tumor-associated Proteins for Combined use as Markers of Non-small Cell Lung Cancer," Proteomics, 2004, vol. 4 (4), pp. 1216-1225.
Communication from the Examining Division and Annex mailed Jun. 6, 2014 for European Application No. 13166996.2 filed Jun. 27, 2008.
Final Office Action mailed Aug. 11, 2014 for U.S. Appl. No. 12/667,069, filed Feb. 14, 2011.
European Patent Office Action for Application No. 12156879.4 dated May 13, 2015 (5 pages).
Cha, H-J. et al., "Role of thymosin Beta4 in tumor metastasis and angiogenesis," J. Natl. Cancer Inst. (2003) 95 (22):1674-1680.
Ji, P. et al., "MALAT-1, a novel noncoding RNA, and thymosin Beta4 predict metastasis and survival in early-stage non-small cell lung cancer," Oncogene (2003) 22:8031-8041.
Ping, H. et al., "The clinical significance of thymosin Beta4 expression in human non-small cell lung cancer," Chin. J. Lung Cancer (2004) 7(6):483-487.
European Patent Office Action for Application No. 131669962 dated Dec. 1, 2015 (5 pages).

\* cited by examiner

SFFSFLGEAF DGAR

EANYIG SDK

METHODS AND MARKER COMBINATIONS FOR SCREENING FOR PREDISPOSITION TO LUNG CANCER

RELATED APPLICATION INFORMATION

This application is a continuation-in-part of U.S. application Ser. No. 11/644,365 filed on Dec. 21, 2006 now abandoned, which claims priority to U.S. Patent Application No. 60/753,331 filed on Dec. 22, 2005, the contents of which are herein incorporated by reference.

SEQUENCE LISTING

The instant application contains a Sequence Listing which has been submitted electronically in ASCII format and is hereby incorporated by reference in its entirety. Said ASCII copy, created on Jan. 21, 2008, is named "SEQUENCELISTINGFINAL.txt" and is 10,557 bytes in size.

BACKGROUND OF THE INVENTION

Lung cancer is the second most common cancer for both men and women in the United States, with an estimated 172,500 new cases projected to be diagnosed during 2005 (American Cancer Society statistics). It is the most common cause of cancer death for both sexes, with over 163,000 lung cancer related deaths expected in 2005. Lung cancer is also a major health problem in other areas of the world. In the European Union, approximately 135,000 new cases occur each year (*Genesis Report*, February 1995). Also, incidence is rapidly increasing in Central and Eastern Europe where men have the world's highest cigarette consumption rates (See, T. Reynolds, *J. Natl. Cancer Inst.* 87: 1348-1349 (1995)). Tobacco alone is responsible for over 90% of all cases of cancer of the lung, trachea, and bronchus (See, CPMCnet, *Guide to Clinical Preventive Services*). The International Agency for Research on Cancer of the World Health Organization estimated that in 2002, worldwide, there were 1,352,000 cases of lung cancer with 1,179,000 deaths due to the disease.

Early stage lung cancer can be detected by chest radiograph and the sputum cytological examination, however these procedures do not have sufficient accuracy to be routinely used as screening tests for asymptomatic individuals. The potential technical problems that can limit the sensitivity of chest radiograph include suboptimal technique, insufficient exposure, and positioning and cooperation of the patient (See, T. G. Tape, et al., *Ann. Intern. Med.* 104: 663-670 (1986)). Radiologists often disagree on interpretations of chest radiographs and over 40% of these are significant or potentially significant (See, P. G. Herman, et al., *Chest* 68: 278-282 (1975)). False-negative interpretations are the cause of most errors and inconclusive results require follow-up testing for clarification (See, T. G. Tape et al., supra).

Sputum cytology is less sensitive than chest radiography in detecting early lung cancer (See, The National Cancer Institute Cooperative Early Lung Cancer Detection Program, *Am. Rev. Resp. Dis.* 130: 565-567 (1984)). Factors affecting the ability of sputum cytology to diagnose lung cancer include the ability of the patient to produce sufficient sputum, the size of the tumor, the proximity of the tumor to major airways, the histologic type of the tumor, and the experience and training of the cytopathologist (See, R. J. Ginsberg et al. In: *Cancer: Principles and Practice of Oncology, Fourth Edition*, pp. 673-723, Philadelphia, Pa.: J/B. Lippincott Co. (1993)).

Most new lung cancers will be detected when the disease has spread beyond the lung. In the United States only 16% of new non-small cell lung cancers are detected at a localized stage when 5-year survival is highest at 49.7%. In contrast, 68% of new cases are detected when the disease has already spread locally or metastasized to distant sites that have 5-year survival rates of 18.5% and 1.8%, respectively. Similarly, 80% of newly detected small-cell lung cancers are discovered with local invasion or distant metastasis which have 5 year survival rates of 9.5% and 1.7%, respectively (See, Stat Bite, *J. Natl. Cancer Inst.* 87:1662 (1995)). These statistics show that current procedures are failing to detect lung cancer at an early, treatable stage of the disease and that improved methods of detection and treatment are needed to reduce mortality.

The most frequently used methods for monitoring lung cancer patients after primary therapy are clinic visit, chest X-ray, complete blood count, liver function testing and chest computed tomography (CT). Detecting recurrence by regular monitoring, however, does not greatly affect the mode of treatment and the overall survival time leading to the conclusion that current monitoring methods are not cost effective (See, K. S. Naunheim et al., *Ann. Thorac. Surg.* 60:1612-1616 (1995); G. L. Walsh et al., *Ann. Thorac. Surg.* 60: 1563-1572 (1995)).

More recently, there has been a re-examination of the use of computed tomography (CT) to screen asymptomatic persons who are at high risk for lung cancer. C. I. Henschke et al., (*Clin. Imaging* 28:317-321 (2004)) reported two studies that indicated that CT scanning can detect asymptomatic lung cancer without generating too many false positives. J. Gohagan et al., (*Chest* 126:114-121 (2004)) evaluated a trial protocol for a randomized study comparing chest X-ray with low dose spiral CT and concluded that a large randomized clinical trial to screen for lung cancer was feasible. However, even if implemented in clinical practice, the cost of CT screening would be high and the number of false positives leading to additional testing would also be high. A low cost blood test with good specificity would complement CT for the early detection of cancer. Another strategy for improving the utility of CT involves the use of a high sensitivity blood test for early stage lung cancer. Such a test could be offered to patients as an alternative to CT or X-ray. If the test were positive, the patient would be imaged; if the test were negative, the patient would not be scanned, but could be retested in the future. Whether a blood test offers high sensitivity or high specificity or, ideally, both, such a test would find utility in the current protocols used to detect early stage lung cancer.

Additionally, there has been a recent re-examination of tumor markers and their usefulness when combined into panels to identify individuals who are at risk for lung cancer. However, the lack of sensitivity that was characteristic of individual markers still prevents panels of tumor markers from being useful for early detection of lung cancer. The tumor antigens that have been found by classical biochemical methods, including alpha Fetoprotein (AFP), CA19-9, CA125, Carcinoembryonic Antigen (CEA), Cytokeratin 8, Cytokeratin 18, Cytokeratin 19 fragments (CYFRA 21-1), Neuron-Specific Enolase (NSE), pro-Grastrin-Releasing Peptide (proGRP), and Squamous Cell Carcinoma Antigen (SCC). These markers have been found to be useful in staging, classifying, predicting outcomes for, and monitoring of lung cancer patients after their diagnosis has been made; however, these markers have not been found to be useful, either alone or in panels, for the early detection of the disease (See, S. Ando, et al., Anticancer Res. 21: 3085-3092 (2001); U.S. Preventive Services Task Force, *Annals of Internal Medicine* 140:738-739 (2004)). In contrast, a panel of known immunoassay markers, specifically, CEA, CYFRA 21-1, SCC, NSE, and ProGRP, are known to be useful in making a histological diagnosis of lung cancer in those circumstances when obtaining a biopsy sample is difficult (See, C. Gruber et al., *Tumor Biology* 27 (Supplement 1): 71 (2006) and P. Stieber et al., *Tumor Biology*, 27 (Supplement 2):S5-4 (2006)).

Attempts have been made to discover improved tumor markers for lung cancer by first identifying differentially expressed cellular components in lung tumor tissue compared to normal lung tissue. Two-dimensional polyacrylamide gel electrophoresis has been used to characterize quantitative and qualitative differences in polypeptide composition (See, T. Hirano et al., *Br. J. Cancer* 72:840-848 (1995); A. T. Endler et al., *J. Clin. Chem Clin. Biochem.* 24:981-992 (1986)). The sensitivity of this technique, however, is limited by the degree of protein resolution of the two electrophoretic steps and by the detection step that depends on staining protein in gels. Also, polypeptide instability will generate artifacts in the two-dimensional pattern.

Attempts have also been made to identify biomarkers and their use in aiding in the diagnosis of lung cancer, such as those described in International Publication No. WO 2005/098445 A2. The biomarkers discussed in WO 2005/098445 were identified using surface-enhanced laser desorption/ionization mass spectrometry (SELDI). Various markers, kits, methods and a decision tree analytical method are disclosed. However, these markers, kits and methods have not been adopted for use in routine practice as these markers and methods have not been duplicated in any laboratory.

The human immune system has long been known to be involved in the development and control of cancer (See, K. de Visser, et al., *Nature Reviews Cancer*, 6: 24-37 (2006)). Therefore, it is not surprising that proteins representing both the innate and the adaptive immune response have been explored as tumor markers for lung cancer.

Acute phase proteins, members of the innate immune family of proteins, including serum amyloid A (SAA), serum amyloid P (SAP), and C-reactive protein (CRP), alpha-1-antichymotrypsin (alpha-1-ACT), alpha-1-antitrypsin (alpha-1-AT), alpha-2-macroglobulin (alpha-2-M), ceruloplasmin (Cp), haptoglobin (Hp), and transferrin (Tf) have been evaluated as biomarkers in early, resectable, lung cancer (See, M. Kasprzyk, et al., *Przegl. Lek.*, 63: 936-940 (2006)). Fibrinogen and CRP have been studied as biomarkers for resectable lung cancer (See, J. Jones, et al., *Lung Cancer*, 53: 97-101 (2006)). Apolipoprotein CIII (apoCIII) has been not been reported to be a biomarker for lung cancer, but it has been reported to be associated with pancreatic cancer (See, J. Chen, et al., *J. Chromatogr. A*, (2007), doi: 10.1016/j.chroma.2007.03.096). The association of acute phase proteins with lung cancer has been known for more than 2 decades (See, P. Weinstein, et al., *Scand. J. Immunol.* 19: 193-198 (1984)); however, no acute phase protein is routinely used in the diagnosis of early stage lung cancer.

There are proteins which are not usually thought to be acute phase proteins, but which are elevated in response to a stress on the subject. Such proteins can be termed host response proteins, a broader category than innate or adaptive immune proteins. One such protein is thymosin beta-4 (TP4), a 44 amino acid peptide which is involved in wound healing. Expression of thymosin beta-4 in tumor tissue is thought to predict a more aggressive and metastatic phenotype for the tumor. Early stage lung cancer patients who express thymosin beta-4 mRNA at high levels have worse survival than patients with lower expression (See, C. Muller-Tidow, et al., *Lung Cancer* 45: S145-150 (2004)).

Autoantibodies, immunoglobulins which react with a patients own proteins (termed autoantigens), comprise the proteins which implement the actions of the adaptive immune system. Scientific publications on the presence of autoantibodies in lung cancer patients date back 40 years (See, G. Levine, et al., *J. Lab. Clin. Med.* 69: 749-757 (1967)). Occasionally, particularly in small cell lung cancer, autoantibodies against nervous system components result in the patient exhibiting neurological symptoms characterized as a paraneoplastic syndrome (See, U. Seneviratne, et al., *Postgrad. Med. J.* 75: 516-520 (1999)). Although dramatic, very few patients exhibit a paraneoplastic syndrome, so neither the syndrome nor autoantibodies against neurological cells or proteins are diagnostically useful for the population at large. The early autoantibody literature has numerous references to circulating anti-p53 antibodies. P53 is a tumor supressor protein which is inactivated by mutation in many cancers. Although patient anti-p53 antibodies react with both native and mutated p53, it is thought that the longer tissue half-life of mutated p53 results in the appearance of this autoantibody in about 30% of lung cancer patients (See, R. Lubin, et al., *Nat. Med.* 1: 701-702 (1995)). There are reports of intracellular proteins, involved in the regulation of cell machinery, which give rise to autoantibodies in cancer. Antibodies to human heat shock protein 40 (Hsp40) have been reported to be found in the serum of lung cancer patients (See, M. Oka, et al., *Jpn. J. Cancer Res.* 92: 316-320 (2001)). This protein is also known as DnaJB1 or hDJ1. Although many proteins have been described which become autoantigens, giving rise to circulating autoantibodies in lung cancer, given the million or more proteins thought to exist in a human subject, there remain many more proteins, both known and unknown, which may prove to be cause diagnostically useful autoantibodies in patients with lung cancer and other chronic diseases.

If multiple autoantibodies are used to classify patients or make a diagnosis, a data analysis protocol is required. J. Koziol, et al., (*Clin. Cancer Res.* 9:5120-5126 (2003)) used recursive partitioning to select autoantibodies for optimal diagnosis of various tumors. They used seven tumor associated antigens: c-myc, cyclin B1, IMP2, Koc, p53, p62, and survivin and achieved good results for a small group (56) of lung cancer patients.

Systematic approaches to find diagnostically useful autoantibodies include the use of protein arrays to screen patient and disease-free sera for reactive autoantibodies. Arrays have been constructed from tumor cell lysates (See, J. Qiu, et al., *J. Proteome Res.* 3:261-267 (2004)) and used to search for novel autoantigens which give rise to diagnostically useful autoantibody signatures in patient sera. Arrays can also be constructed from recombinantly expressed proteins (See, D. Mattoon, et al., *Expert. Rev. Proteomics* 2: 879-889 (2005)). Affinity chromatography methodologies have been described which may prove useful to find diagnostic autoantibodies (*J. Sep. Sci.* 30:352-358 (2007)). To date none of these approaches have yielded novel autoantibodies useful for the early detection of lung cancer.

Another systematic approach to discovering diagnostically useful autoantibodies is the so-called SEREX method. SEREX stands for Serological Analysis of Recombinant cDNA Expression Libraries and has been used to discover a novel testicular antigen which is aberrantly expressed in a variety of cancers (See, Y. Chen, et al., *Proc. Natl. Acad. Sci. U.S.A.* 94: 1914-1918 (1997)). NY-ESO-1 is a protein of about 18 kD and has been extensively studied as a tumor autoantibody. Approximately 20% of non-small cell lung cancer patients have circulating antibodies against the protein as measured by an ELISA (See, O. Tureci, et al., *Cancer Lett.* 236: 64-71 (2006)).

Attempts have also been made to discover an immune response specific for lung cancer by surveying peptide libraries expressed in yeast or bacteria with sera from diseased and non-diseased individuals. Publications from the laboratory of Hirschowitz (See, L. Zhong et al., *Chest* 125:105-106 (2004), L. Zhong et al., *Am. J. Respir. Crit. Care Med.* 15:1308-1314 (2005)) have described the use of phage libraries to find proteins which are autoantigens to patients with lung cancer. The authors have reported on the successful identification of both symptomatic and asymptomatic lung cancer patients in controlled studies. However, the number of cases and controls are limited (<200 total subjects) and the method needs to be validated on a much larger population.

Currently, the identification of individuals at risk for lung cancer is based largely on the smoking history of the individual. Other environmental exposures such as asbestos, particulates, etc., can increase the risk of developing lung cancer as well. These known risk factors have been combined in one or more algorithms and are accessible to clinicians and the public for assessing the risk of individuals for lung cancer (See, P. B. Bach et al., *J. Natl. Cancer Inst.* 95:470-478 (2003)). Unfortunately, this algorithm is neither sensitive nor specific enough to be useful for the detection of early stage lung cancer. Indeed, based on the cited algorithm, an individual with a significant smoking history will have a relative risk of 1/500 to 1/100 for developing lung cancer. This means that even using the method of Bach et al. as many as 499 out of 500 CT scans will not lead to the discovery of a case of lung cancer.

Thereupon, there remains a need in the art for methods and markers useful for detecting lung cancer that are fast, convenient and cost-effective to perform. It would also be advantageous to provide specific methods and certain combinations of markers that could be used to determine whether a patient is at risk of developing lung cancer or has lung cancer. Such methods would include a method for testing a sample for one or more markers indicative of lung cancer and detecting such markers. Such methods can include improved methods for analyzing mass spectra of a biological sample for markers or assaying a sample and then detecting markers as a risk of developing lung cancer or as indication of lung cancer.

SUMMARY OF THE INVENTION

The invention is based in part on the discovery that rapid, sensitive methods for aiding in the detection of lung cancer in a subject suspected of having lung cancer can be based on certain combinations of biomarkers and biomarkers and biometric parameters.

In one aspect, the method can comprise the steps of:
a. quantifying in a test sample obtained from a subject, the amount of one or more biomarkers in a panel;
b. comparing the amount of each biomarker in the panel to a predetermined cutoff for said biomarker and assigning a score for each biomarker based on said comparison;
c. combining the assigned score for each biomarker determined in step b to obtain a total score for said subject;
d. comparing the total score determined in step c with a predetermined total score; and
e. determining whether said subject has a risk of lung cancer based on the comparison of the total score in step d.

In the above method, the DFI of the biomarkers relative to lung cancer is preferably less than about 0.4.

Optionally, the above method can further comprise the step of obtaining a value for at least one biometric parameter from a subject. An example of a biometric parameter that can be obtained is the smoking history of the subject. If the above method further comprises the step of obtaining a value for at least one biometric parameter from the subject, then the method can further comprise the step of comparing the value of the at least one biometric parameter against a predetermined cutoff for each said biometric parameter and assigning a score for each biometric parameter based on said comparison, combining the assigned score for each biometric parameter with the assigned score for each biomarker quantified in step b to obtain a total score for said subject in step c, comparing the total score with a predetermined total score in step d and determining whether said subject has a risk of lung cancer based on the total score in step e.

Examples of biomarkers that can be quantified in the above method are one or more biomarkers selected from the group of antibodies, antigens, regions of interest or any combinations thereof. More specifically, the biomarkers that can be quantified include, but are not limited to, one or more of: anti-p53, anti-TMP21, anti-NY-ESO-1, anti-HDJ1, anti-Niemann-Pick C1-Like protein 1, C terminal peptide-domain (anti-NPC1L1C-domain), anti-TMOD1, anti-CAMK1, anti-RGS1, anti-PACSIN1, anti-RCV1, anti-MAPKAPK3, anti-Cyclin E2 (namely, at least one antibody against immunoreactive Cyclin E2), cytokeratin 8, cytokeratin 19, cytokeratin 18, CEA, CA125, CA15-3, SCC, CA19-9, proGRP, serum amyloid A, alpha-1-anti-trypsin, apolipoprotein CIII and T04, Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959.

Optionally, the panel used in the above method can comprise quantifying the amount of two or more biomarkers, three or more biomarkers, four or more biomarkers, five or more biomarkers, six or more biomarkers, seven or more biomarkers, eight biomarkers, nine or more biomarkers, ten or more biomarkers, eleven or more biomarkers, twelve or more biomarkers, thirteen or more biomarkers, fourteen or more biomarkers, fifteen or more biomarkers, sixteen or more biomarkers, seventeen or more biomarkers, eighteen or more biomarkers, nineteen or more biomarkers or twenty biomarkers or more, etc.

In another aspect, the method can comprise the steps of:
a. obtaining a value for at least one biometric parameter of a subject;
b. comparing the value of the at least one biometric parameter against a predetermined cutoff for each said biometric parameter and assigning a score for each biometric parameter based on said comparison;
c. quantifying in a test sample obtained from a subject, the amount of two or more biomarkers in a panel, the panel comprising at least one antibody and at least one antigen;
d. comparing the amount of each biomarker quantified in the panel to a predetermined cutoff for said biomarker and assigning a score for each biomarker based on said comparison;
e. combining the assigned score for each biometric parameter determined in step b with the assigned score for each biomarker determined in step d to obtain a total score for said subject;
f. comparing the total score determined in step e with a predetermined total score; and
g. determining whether said subject has a risk of lung cancer based on the comparison of the total score determined in step f.

In the above method, the DFI of the biomarkers relative to lung cancer is preferably less than about 0.4.

In the above method, the panel can comprise at least one antibody selected from the group consisting of: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2 and at least one antigen selected from the group consisting of: cytokeratin 8, cytokeratin 19, cytokeratin 18, CEA, CA125, CA15-3, SCC, CA19-9, proGRP, serum amyloid A, alpha-1-anti-trypsin, apolipoprotein CIII and T04.

In the above method, the biometric parameter obtained from the subject is selected from the group consisting of the subject's smoking history, age, carcinogen exposure and gender. Preferably, the biometric parameter is the subject's pack-years of smoking.

Optionally, the method can further comprise quantifying at least one region of interest in the test sample. If a region of interest is to be quantified in the test sample, then the panel can further comprise at least one region of interest selected from the group consisting of: Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959.

Optionally, the above method can also employ a Weighted Scoring Method to determine whether a subject is at risk of developing lung cancer. If the above method employs such a Weighted Scoring Method, then in said method, step b comprises comparing the value of at least one biometric parameter to a number of predetermined cutoffs for said biometric parameter and assigning a score for each biometric parameter based on said comparison, step d comprises comparing the amount of each biomarker in the panel to a number of predetermined cutoffs for said biomarker and assigning a score for each biomarker based on said comparison, step e comprises combining the assigned score for each biometric parameter in step b with the assigned score for each biomarker in step d to come up a total score for said subject, step f comprises comparing the total score determined in step e with a predetermined total score and step g comprises determining whether said subject has lung cancer based on the comparison of the total score determined in step f.

In another aspect, the method can comprise the steps of:

a. quantifying in a test sample obtained from a subject, the amount of two or more biomarkers in a panel, the panel comprising at least one antibody and at least one antigen;

b. comparing the amount of each biomarker quantified in the panel to a predetermined cutoff for said biomarker and assigning a score for each biomarker based on said comparison;

c. combining the assigned score for each biomarker quantified in step b to obtain a total score for said subject;

d. comparing the total score determined in step c with a predetermined total score; and e. determining whether said subject has a risk of lung cancer based on the comparison of the total score determined in step d.

In the above method, the DFI of the biomarkers relative to lung cancer is preferably less than about 0.4.

In the above method, the panel can comprise at least one antibody selected from the group consisting of: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2. The panel can comprise at least one antigen selected from the group consisting of: cytokeratin 8, cytokeratin 19, cytokeratin 18, CEA, CA125, CA15-3, SCC, CA19-9, proGRP, serum amyloid A, alpha-1-anti-trypsin, apolipoprotein CIII and Tβ4.

Optionally, the method can further comprise quantifying at least one region of interest in the test sample. If a region of interest is to be quantified, then the panel can further comprise at least one region of interest selected from the group consisting of: Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959.

Optionally, the above method can also employ a Weighted Scoring Method to determine whether a subject is at risk of developing lung cancer. If the above method employs such a Weighted Scoring Method, then in said method, step b comprises comparing the amount of each biomarker in the panel to a number of predetermined cutoffs for said biomarker and assigning a score for each biomarker based on said comparison, step c comprises combining the assigned score for each biomarker quantified in step b to obtain a total score for said subject, step d comprises comparing the total score determined in step c with a predetermined total score and step e comprises determining whether said subject has lung cancer based on the comparison of the total score determined in step d.

In another aspect, the method can comprise the steps of:

a. quantifying in a test sample obtained from a subject, an amount of at least one biomarker in a panel, the panel comprising at least one anti-Cyclin E2;

b. comparing the amount of each biomarker quantified in the panel to a predetermined cutoff for said biomarker and assigning a score for each biomarker based on said comparison;

c. combining the assigned score for each biomarker quantified in step b to obtain a total score for said subject;

d. comparing the total score determined in step c with a predetermined total score; and e. determining whether said subject has a risk of lung cancer based on the comparison of the total score determined in step d.

In the above method, the DFI of the biomarkers relative to lung cancer is preferably less than about 0.4.

Optionally, the above method can further comprise quantifying at least one antigen in the test sample, quantifying at least one antibody in the test sample, or quantifying a combination of at least one antigen and at least one antibody in the test sample. Thereupon, if at least one antigen, at least one antibody or a combination of at least one antigen and at least one antibody are to be quantified in the test sample, then the panel can further comprise at least one antigen selected from the group consisting of: cytokeratin 8, cytokeratin 19, cytokeratin 18, CEA, CA125, CA15-3, SCC, CA19-9, proGRP, serum amyloid A, alpha-1-anti-trypsin, apolipoprotein CIII and Tβ4, at least one antibody selected from the group consisting of: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 or any combinations thereof.

Optionally, the method can further comprise quantifying at least one region of interest in the test sample. If a region of interest is to be quantified, then the panel can further comprise at least one region of interest selected from the group consisting of: Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959.

Optionally, the above method can also employ a Weighted Scoring Method to determine whether a subject is at risk of developing lung cancer. If the above method employs such a Weighted Scoring Method, then in said method, step b comprises comparing the amount of each biomarker in the panel to a number of predetermined cutoffs for said biomarker and assigning a score for each biomarker based on said comparison, step c comprises combining the assigned score for each biomarker quantified in step b to obtain a total score for said subject, step d comprises comparing the total score determined in step c with a predetermined total score and step e comprises determining whether said subject has lung cancer based on the comparison of the total score determined in step d.

Optionally, the above method can further comprise the step of obtaining a value for at least one biometric parameter from a subject. A biometric parameter that can be obtained from a subject can be selected from the group consisting of: a subject's smoking history, age, carcinogen exposure and gender. A preferred biometric parameter that is obtained is the subject's pack-years of smoking. If the above method further comprises the step of obtaining a value for at least one biometric parameter from the subject, then the method can further comprise the step of comparing the value of at least one biometric parameter against a predetermined cutoff for each said biometric parameter and assigning a score for each biometric parameter based on said comparison, combining the assigned score for each biometric parameter with the assigned score for each biomarker quantified in step b to obtain a total score for said subject, comparing the total score with a predetermined total score in step c and determining whether said subject has a risk of lung cancer based on the comparison of the total score in step d.

In another aspect, the method can comprise the steps of:

a. quantifying in a test sample obtained from a subject at least one biomarker in a panel, the panel comprising at least one biomarker selected from the group consisting of: cytokeratin 8, cytokeratin 19, cytokeratin 18, CEA, CA125, CA15-3, SCC, CA19-9, proGRP, serum amyloid A, alpha-1-antitrypsin, apolipoprotein CIII and Tβ4;

b. comparing the amount of each biomarker quantified in the panel to a predetermined cutoff for said biomarker and assigning a score for each biomarker based on said comparison;

c. combining the assigned score for each biomarker quantified in step b to obtain a total score for said subject;

d. comparing the total score quantified in step c with a predetermined total score; and e. determining whether said subject has lung cancer based on the comparison of the total score in step d.

In the above method, the DFI of the biomarkers relative to lung cancer is preferably less than about 0.4.

Optionally, the above method can further comprise quantifying at least one antibody in the test sample. Thereupon, the panel can further comprise at least one antibody selected from the group consisting of: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2 or any combinations thereof.

Optionally, the method can further comprise quantifying at least one region of interest in the test sample. If a region of interest is to be quantified, then the panel can further comprise at least one region of interest selected from the group consisting of: Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959.

Optionally, the above method can also employ a Weighted Scoring Method to determine whether a subject is at risk of developing lung cancer. If the above method employs such a Weighted Scoring Method, then in said method, step b comprises comparing the amount of each biomarker in the panel to a number of predetermined cutoffs for said biomarker and assigning a score for each biomarker based on said comparison, step c comprises combining the assigned score for each biomarker quantified in step b to obtain a total score for said subject, step d comprises comparing the total score determined in step c with a predetermined total score and step e comprises determining whether said subject has lung cancer based on the comparison of the total score determined in step d.

Optionally, the above method can further comprise the step of obtaining a value for at least one biometric parameter from a subject. A biometric parameter that can be obtained from a subject can be selected from the group consisting of: a subject's smoking history, age, carcinogen exposure and gender. A preferred biometric parameter that is obtained is the subject's pack-years of smoking. If the above method further comprises the step of obtaining a value for at least one biometric parameter from the subject, then the method can further comprise the step of comparing the value of at least one biometric parameter against a predetermined cutoff for each said biometric parameter and assigning a score for each biometric parameter based on said comparison, combining the assigned score for each biometric parameter with the assigned score for each biomarker quantified in step b to obtain a total score for said subject, comparing the total score with a predetermined total score in step c and determining whether said subject has a risk of lung cancer based on the comparison of the total score in step d.

In another aspect, the method can comprise the steps of:

a. quantifying in a test sample obtained from a subject, at least one biomarker in a panel, the panel comprising at least one biomarker, wherein the biomarker is a region of interest selected from the group consisting of: Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959;

b. comparing the amount of each biomarker quantified in the panel to a predetermined cutoff for said biomarker and assigning a score for each biomarker based on said comparison;

c. combining the assigned score for each biomarker quantified in step b to obtain a total score for said subject;

d. comparing the total score quantified in step c with a predetermined total score; and e. determining whether said subject has lung cancer based on the comparison of the total score determined in step d.

In the above method, the DFI of the biomarkers relative to lung cancer is preferably less than about 0.4.

Optionally, the above method can further comprise quantifying at least one antigen in the test sample, quantifying at least one antibody in the test sample, or quantifying a combination of at least one antigen and at least one antibody in the test sample. Thereupon, if at least one antigen, at least one antibody or a combination of at least one antigen or antibody are to be quantified in the test sample, then the panel can further comprise at least one antigen selected from the group consisting of: cytokeratin 8, cytokeratin 19, cytokeratin 18, CEA, CA125, CA15-3, SCC, CA19-9, proGRP, serum amyloid A, alpha-1-anti-trypsin, apolipoprotein CIII and T04, at least one antibody selected from the group consisting of: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2 or any combinations thereof.

Optionally, the above method can also employ a Weighted Scoring Method to determine whether a subject is at risk of developing lung cancer. If the above method employs such a Weighted Scoring Method, then in said method, step b comprises comparing the amount of each biomarker in the panel to a number of predetermined cutoffs for said biomarker and assigning a score for each biomarker based on said comparison, step c comprises combining the assigned score for each biomarker quantified in step b to obtain a total score for said subject, step d comprises comparing the total score determined in step c with a predetermined total score and step e comprises determining whether said subject has lung cancer based on the comparison of the total score determined in step d.

Optionally, the above method can further comprise the step of obtaining a value for at least one biometric parameter from a subject. A biometric parameter that can be obtained from a subject can be selected from the group consisting of: a subject's smoking history, age, carcinogen exposure and gender. A preferred biometric parameter that is obtained is the subject's pack-years of smoking. If the above method further comprises the step of obtaining a value for at least one biometric parameter from the subject, then the method can further comprise the step of comparing the value of at least one biometric parameter against a predetermined cutoff for each said biometric parameter and assigning a score for each biometric parameter based on said comparison, combining the assigned score for each biometric parameter with the assigned score for each biomarker quantified in step b to obtain a total score for said subject, comparing the total score with a predetermined total score in step c and determining whether said subject has a risk of lung cancer based on the comparison of the total score in step d.

In another aspect, the method can comprise the steps of:
a. quantifying in a test sample obtained from a subject, the amount of two or more biomarkers in a panel, the panel comprising two or more of: cytokeratin 19, cytokeratin 18, CA 19-9, CEA, CA15-3, CA125, SCC, ProGRP, ACN9459, Pub11597, Pub4789, TFA2759, TFA9133, Pub3743, Pub8606, Pub4487, Pub4861, Pub6798, Tfa6453 and Hic3959;
b. comparing the amount of each biomarker in the panel to a predetermined cutoff for said biomarker and assigning a score for reach biomarker based on said comparison;
c. combining the assigned score for each biomarker determined in step b to obtain a total score for said subject;
d. comparing the total score determined in step c with a predetermined total score; and
e. determining whether said subject has risk of lung cancer based on the comparison of the total score determined in step d.

In the above method, the DFI of the biomarkers relative to lung cancer is preferably less than about 0.4.

Optionally, the panel in the above method can comprise: (1) cytokeratin 19, CEA, ACN9459, Pub11597, Pub4789 and TFA2759; (2) cytokeratin 19, CEA, ACN9459, Pub11597, Pub4789, TFA2759 and TFA9133; (3) cytokeratin 19, CA19-9, CEA, CA15-3, CA125, SCC, cytokeratin 18 and ProGRP; (4) Pub11597, Pub3743, Pub8606, Pub4487, Pub4861, Pub6798, Tfa6453 and Hic3959; or (5) cytokeratin 19, CEA, CA125, SCC, cytokeratin 18, ProGRP, ACN9459, Pub11597, Pub4789, TFA2759, TFA9133.

Optionally, the above method can also employ a Weighted Scoring Method to determine whether a subject is at risk of developing lung cancer. If the above method employs such a Weighted Scoring Method, then in said method, step b comprises comparing the amount of each biomarker in the panel to a number of predetermined cutoffs for said biomarker and assigning a score for each biomarker based on said comparison, step c comprises combining the assigned score for each biomarker quantified in step b to obtain a total score for said subject, step d comprises comparing the total score determined in step c with a predetermined total score and step e comprises determining whether said subject has lung cancer based on the comparison of the total score determined in step d.

In another aspect, the method can comprise the steps of:
a. quantifying in a test sample obtained from a subject, the amount of two or more biomarkers in a panel, wherein the panel comprises anti-p53, anti-NY-ESO-1, anti-MAPKAPK3, anti-Cyclin E2, cytokeratin 19, CEA, CA 125 and ProGRP;
b. comparing the amount of each biomarker quantified in the panel to a predetermined cutoff for said biomarker and assigning a score for each biomarker based on said comparison;
c. combining the assigned score for each biomarker quantified in step b to obtain a total score for said subject;
d. comparing the total score determined in step c with a predetermined total score; and
e. determining whether said subject has a risk of lung cancer based on the comparison of the total score determined in step d.

Optionally, the panel can comprise quantifying the amount of three or more biomarkers, four or more biomarkers, five or more biomarkers, six or more biomarkers, seven or more biomarkers or eight biomarkers.

Optionally, in the above method, the anti-Cyclin E2 can be an antibody against SEQ ID NO:3, SEQ ID NO:4 or SEQ ID NO:5.

Optionally, the above method can further comprise the step of obtaining a value for at least one biometric parameter from a subject. A biometric parameter that can be obtained from a subject can be selected from the group consisting of: a subject's smoking history, age, carcinogen exposure and gender. A preferred biometric parameter that is obtained is the subject's pack-years of smoking. If the above method further comprises the step of obtaining a value for at least one biometric parameter from the subject, then the method can further comprise the step of comparing the value of the at least one biometric parameter against a predetermined cutoff for each said biometric parameter and assigning a score for each biometric parameter based on said comparison, combining the assigned score for each biometric parameter with the assigned score for each biomarker quantified in step b to obtain a total score for said subject, comparing the total score with a predetermined total score in step d and determining whether said subject has a risk of lung cancer based on the comparison of the total score in step e.

Optionally, the above method can also employ a Weighted Scoring Method to determine whether a subject is at risk of developing lung cancer. If the above method employs such a Weighted Scoring Method, then in said method, step b comprises comparing the amount of each biomarker in the panel to a number of predetermined cutoffs for said biomarker and assigning a score for each biomarker based on said comparison, step c comprises combining the assigned score for each biomarker quantified in step b to obtain a total score for said subject, step d comprises comparing the total score determined in step c with a predetermined total score and step e comprises determining whether said subject has risk of lung cancer based on the comparison of the total score determined in step d.

The present invention also relates to a variety of different kits that can be used in the methods described above. In one aspect, a kit can comprise a peptide selected from the group consisting of: SEQ ID NO:1, SEQ ID NO:3, SEQ ID NO:4, SEQ ID NO:5 or any combinations thereof. In another aspect, a kit can comprise at least one antigen reactive against immunoreactive Cyclin E2 or any combinations thereof. In another aspect, a kit can comprise at least one antigen reactive against immunoreactive Cyclin E2 or any combinations thereof. In a further aspect, a kit can comprise (a) reagents containing at least one antibody for quantifying one or more antigens in a test sample, wherein said antigens are: cytokeratin 8, cytokeratin 19, cytokeratin 18, CEA, CA125, CA15-3, SCC, CA19-9, proGRP, serum amyloid A, alpha-1-anti-trypsin, apolipoprotein CIII and Tβ4; (b) reagents containing one or more antigens for quantifying at least one antibody in a test sample; wherein said antibodies are: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2; and (c) one or more algorithms for combining and comparing the amount of each antigen and antibody in the test sample against a predetermined cutoff and assigning a score for each antigen and antibody based on said comparison, combining the assigned score for each antigen and antibody to obtain a total score, comparing the total score with a predetermined total score and using said comparison as an aid in determining whether a subject has lung cancer. In a further aspect, a kit can comprise (a) reagents containing at least one antibody for quantifying one or more antigens in a test sample, wherein said antigens are: cytokeratin 8, cytokeratin 19, cytokeratin 18, CEA, CA125, CA15-3, SCC, CA19-9, proGRP, serum amyloid A, alpha-1-anti-trypsin, apolipoprotein CIII and Tβ4; (b) reagents containing one or more antigens for quantifying at least one antibody in a test sample; wherein said antibodies are: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2; (c) reagents for quantifying one or more regions of interest selected from the group consisting of: ACN9459, Pub11597, Pub4789, TFA2759, TFA9133, Pub3743, Pub8606, Pub4487, Pub4861, Pub6798, Tfa6453 and Hic3959; and (d) one or more algorithms for combining and comparing the amount of each antigen, antibody and region of interest quantified in the test sample against a predetermined cutoff and assigning a score for each antigen, antibody and region of interest quantified based on said comparison, combining the assigned score for each antigen, antibody and region of interest quantified to obtain a total score, comparing the total score with a predetermined total score and using said comparison as an aid in determining whether a subject has lung cancer. In yet still another aspect, a kit can comprise: (a) reagents containing at least one antibody for quantifying one or more antigens in a test sample, wherein said antigens are cytokeratin 19, cytokeratin 18, CA19-9, CEA, CA-15-3, CA125, SCC and ProGRP; (b) reagents for quantifying one or more regions of interest selected from the group consisting of: ACN9459, Pub11597, Pub4789, TFA2759, TFA9133, Pub3743, Pub8606, Pub4487, Pub4861, Pub6798, Tfa6453 and Hic3959; and (c) one or more algorithms for combining and comparing the amount of each antigen and region of interest quantified in the test sample against a predetermined cutoff, assigning a score for each antigen and biomarker quantified based on said comparison, combining the assigned score for each antigen and region of interest quantified to obtain a total score, comparing the total score with a predetermined total score and using said comparison as an aid in determining whether a subject has lung cancer. Examples of antigens and regions of interest that can be quantified are: (a) cytokeratin 19 and CEA and Acn9459, Pub11597, Pub4789 and Tfa2759; (b) cytokeratin 19 and CEA and Acn9459, Pub11597, Pub4789, Tfa2759 and Tfa9133; and (c) cytokeratin 19, CEA, CA 125, SCC, cytokeratin 18, and ProGRP and ACN9459, Pub11597, Pub4789 and Tfa2759. In another aspect, a kit can comprise (a) reagents containing at least one antibody for quantifying one or more antigens in a test sample, wherein said antigens are cytokeratin 19, cytokeratin 18, CA 19-9, CEA, CA15-3, CA125, SCC and ProGRP; and (b) one or more algorithms for combining and comparing the amount of each antigen quantified in the test sample against a predetermined cutoff and assigning a score for each antigen quantified based on said comparison, combining the assigned score for each antigen quantified to obtain a total score, comparing the total score with a predetermined total score and using said comparison as an aid in determining whether a subject has lung cancer. Examples of antigens that can be quantified using the kit are cytokeratin 19, cytokeratin 18, CA19-9, CEA, CA15-3, CA125, SCC and ProGRP. In another aspect, a kit can comprise (a) reagents for quantifying one or more biomarkers, wherein said biomarkers are regions of interest selected from the group consisting of: ACN9459, Pub11597, Pub4789, TFA2759, TFA9133, Pub3743, Pub8606, Pub4487, Pub4861, Pub6798, Tfa6453 and Hic3959; and (b) one or more algorithms for combining and comparing the amount of each biomarker quantified in the test sample against a predetermined cutoff and assigning a score for each biomarker quantified based on said comparison, combining the assigned score for each biomarker quantified to obtain a total score, comparing the total score with a predetermined total score and using said comparison as an aid in determining whether a subject has lung cancer. Examples of regions of interest that can be quantified using the kit can be selected from the group consisting of: Pub11597, Pub3743, Pub8606, Pub4487, Pub4861, Pub6798, Tfa6453 and Hic3959. In yet another aspect, a kit can comprise (a) reagents containing at least one antibody for quantifying one or more antigens in a test sample, wherein said antigens are: cytokeratin 19, CEA, CA 125 and ProGRP; (b) reagents containing one or more antigens for quantifying at least one antibody in a test sample; wherein said antibodies are: anti-p53, anti-NY-ESO-1, anti-MAPKAPK3 and anti-Cyclin E2; and (c) one or more algorithms for combining and comparing the amount of each antigen and antibody quantified in the test sample against a predetermined cutoff and assigning a score for each antigen and antibody quantified based on said comparison, combining the assigned score for each antigen and antibody quantified to obtain a total score, comparing the total score with a predetermined total score and using said comparison as an aid in determining whether a subject has lung cancer. Optionally, the kit can comprise reagents for quantifying each of cytokeratin 19, CEA, CA125 and ProGRP in a test sample, reagents for quantifying each of anti-p53, anti-NY-ESO-1, anti-MAPKAPK3 and anti-Cyclin E2 in a test sample or reagents for quantifying each of cytokeratin 19, CEA, CA 125 ProGRP, anti-p53, anti-NY-ESO-1, anti-MAPKAPK3 and anti-Cyclin E2 in a test sample.

The present invention also relates to isolated or purified polypeptides. The isolated or purified polypeptides contemplated by the present invention are: (a) an isolated or purified polypeptide having (comprising) an amino acid sequence selected from the group consisting of: SEQ ID NO:3 and a polypeptide having 60% homology to the amino acid sequence of SEQ ID NO:3; (b) an isolated or purified polypeptide consisting essentially of an amino acid sequence selected from the group consisting of: SEQ ID NO:3 and a polypeptide having 60% homology to the amino acid sequence of SEQ ID NO:3; (c) an isolated or purified polypeptide consisting of an amino acid sequence of SEQ ID NO:3; (d) an isolated or purified polypeptide having an amino acid sequence selected from the group consisting of: SEQ ID NO:4 and a polypeptide having 60% homology to the amino acid sequence of SEQ ID NO:4; (e) an isolated or purified polypeptide consisting essentially of an amino acid sequence selected from the group consisting of: SEQ ID NO:4 and a polypeptide having 60% homology to the amino acid sequence of SEQ ID NO:4; (f) an isolated or purified polypeptide consisting of an amino acid sequence of SEQ ID NO:4; (g) an isolated or purified polypeptide having an amino acid sequence selected from the group consisting of: SEQ ID NO:5 and a polypeptide having 60% homology to the amino acid sequence of SEQ ID NO:5; (h) an isolated or purified polypeptide consisting essentially of an amino acid sequence selected from the group consisting of: SEQ ID NO:5 and a polypeptide having 60% homology to the amino acid sequence of SEQ ID NO:5; and (i) an isolated or purified polypeptide consisting of an amino acid sequence of SEQ ID NO:5.

The present invention also relates to a unique Weighted Scoring Method. This method can be used for scoring one or more markers obtained from a subject. This method can comprise the steps of:

a. quantifying the amount of a marker obtained from a test sample of a subject;

b. comparing the amount of each marker quantified to a number of predetermined cutoffs for said marker and assigning a score for each marker based on said comparison; and c. combining the assigned score for each marker quantified in step b to obtain a total score for said subject.

In the above method, the predetermined cutoffs are based on ROC curves and the score for each marker is calculated based on the specificity of the marker. Additionally, the marker in the above method can be a biomarker, a biometric parameter or a combination of a biomarker and a biometric parameter.

Additionally, the present invention provides a method for determining a subject's risk of developing a medical condition using the Weighted Scoring Method. This method can comprise the steps of:

a. quantifying in a test sample obtained from a subject the amount of at least one marker;

b. comparing the amount of each marker quantified to a number of predetermined cutoffs for said marker and assigning a score for each marker based on said comparison;

c. combining the assigned score for each marker quantified in step b to obtain a total score for said subject;

d. comparing the total score determined in step c with a predetermined total score; and e. determining whether said subject has a risk of developing a medical condition based on the comparison of the total score determined in step d.

In the above method, the predetermined cutoffs are based on ROC curves and the score for each marker is calculated based on the specificity of the marker. Additionally, the marker in the above method can be a biomarker, a biometric parameter or a combination of a biomarker and a biometric parameter.

BRIEF DESCRIPTION OF THE FIGURES

In FIG. 6, -◊- is the SSM score based on split points to give maximum accuracy; -■- is the SSM score based on split points to give 98% specificity; and -●- is the MoM score.

In FIG. 7, —— is less than 20 pack years (packyr) of smoking; -□- is greater than 20 packyr; and -●- is unknown packyr.

FIG. 8 shows the ability of each individual biomarker tested to differentiate early and late stage lung cancer from normal and benign lung disease subjects. In this FIG. 8, -●- shows early versus normal; -○- shows early versus benign; —— shows late versus normal; and ------- - shows late versus benign.

DETAILED DESCRIPTION OF THE INVENTION

Definitions

Figure 1:
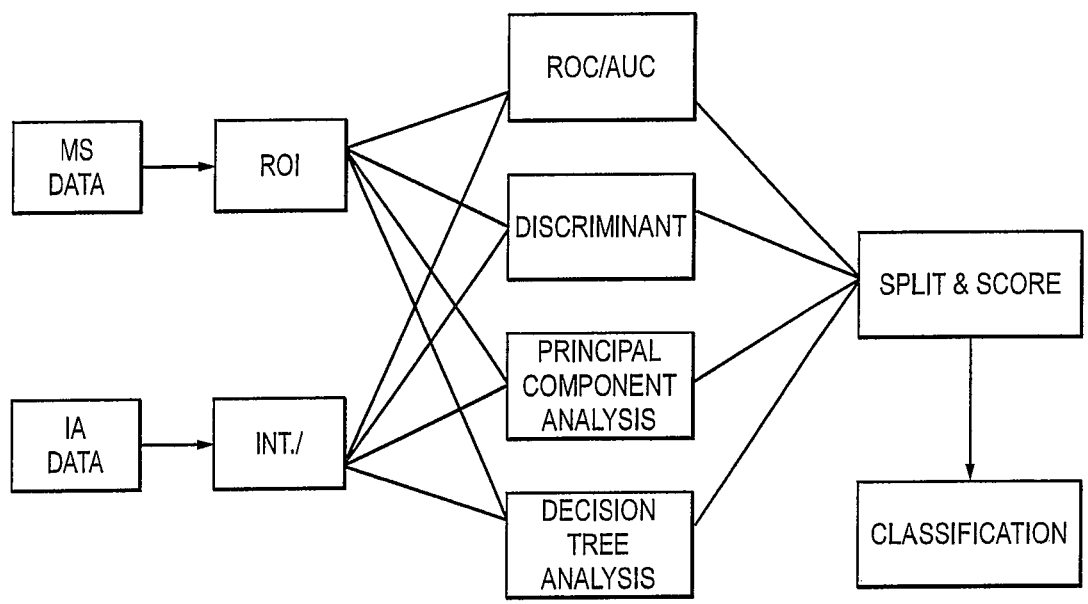
FIG. 1 is a diagram of a bio-informatics workflow. Specifically, MS data and IA data were subjected to various statistical methods. Logistic regression was used to generate Receiver Operator Characteristic (ROC) curves and obtain the Area Under the Curve (AUC) for each marker. The top markers with the highest AUC were selected as candidate markers. Multi-variate analysis (MVA) such as Discriminant Analysis (DA), Principal Component Analysis (PCA) and Decision Trees (DT) identified additional markers for input into the model. Biometric parameters can also be included. Robust markers that occur in at least 50% of the training sets are identified by the Split and Score method/algorithm (SSM) and are selected as putative biomarkers. The process is repeated n times until a suitable number of markers is obtained for the final predictive model.

As used in this application, the following terms have the following meanings. All other technical and scientific terms have the meaning commonly understood by those of ordinary skill in this art.

The term "adsorbent" refers to any material that is capable of accumulating (binding) a biomolecule. The adsorbent typically coats a biologically active surface and is composed of a single material or a plurality of different materials that are capable of binding a biomolecule or a variety of biomolecules based on their physical characteristics. Such materials include, but are not limited to, anion exchange materials, cation exchange materials, metal chelators, polynucleotides, oligonucleotides, peptides, antibodies, polymers (synthetic or natural), paper, etc.

As used herein, the term "antibody" refers to an immunoglobulin molecule or immunologically active portion thereof, namely, an antigen-binding portion. Examples of immunologically active portions of immunoglobulin molecules include F(ab) and F(ab')$_2$ fragments which can be generated by treating an antibody with an enzyme, such as pepsin. Examples of antibodies include, but are not limited to, polyclonal antibodies, monoclonal antibodies, chimeric antibodies, human antibodies, humanized antibodies, recombinant antibodies, single-chain Fvs ("scFv"), an affinity maturated antibody, single chain antibodies, single domain antibodies, F(ab) fragments, F(ab') fragments, disulfide-linked Fvs ("sdFv"), and antiidiotypic ("anti-Id") antibodies and functionally active epitope-binding fragments of any of the above. As used herein, the term "antibody" also includes autoantibodies (Autoantibodies are antibodies which a subject or patient synthesizes which are directed toward normal self proteins (or self antigens) such as, but not limited to, p53, calreticulin, alpha-enolase, and HOXB7. Autoantibodies against a wide range of self antigens are well known to those skilled in the art and have been described in many malignant diseases including lung cancer, breast cancer, prostate cancer, and pancreatic cancer among others). An antibody is a type of biomarker.

As used herein, the term "antigen" refers a molecule capable of being bound by an antibody and that is additionally capable of inducing an animal to produce antibodies capable of binding to at least one epitope of that antigen. Additionally, a region of interest may also be an antigen (in other words, it may ultimately be determined to be an antigen). An antigen is a type of biomarker.

The term "AUC" refers to the Area Under the Curve of a ROC Curve. It is used as a figure of merit for a test on a given sample population and gives values ranging from 1 for a perfect test to 0.5 in which the test gives a completely random response in classifying test subjects. Since the range of the AUC is only 0.5 to 1.0, a small change in AUC has greater significance than a similar change in a metric that ranges for 0 to 1 or 0 to 100%. When the % change in the AUC is given, it will be calculated based on the fact that the full range of the metric is 0.5 to 1.0. The JMP™ statistical package reports AUC for each ROC curve generated. AUC measures are a valuable means for comparing the accuracy of the classification algorithm across the complete data range. Those classification algorithms with greater AUC have by definition, a greater capacity to classify unknowns correctly between the two groups of interest (diseased and not-diseased). The classification algorithm may be as simple as the measure of a single molecule or as complex as the measure and integration of multiple molecules.

The term "benign lung disease" or "benign" refers to a disease condition associated with the pulmonary system of any given subject. In the context of the present invention, a benign lung disease includes, but is not limited to, chronic obstructive pulmonary disorder (COPD), acute or chronic inflammation, benign nodule, benign neoplasia, dysplasia, hyperplasia, atypia, bronchiectasis, histoplasmosis, sarcoidosis, fibrosis, granuloma, hematoma, emphysema, atelectasis, histiocytosis and other non-cancerous diseases.

The term "biologically active surface" refers to any two- or three-dimensional extension of a material that biomolecules can bind to, or interact with, due to the specific biochemical properties of this material and those of the biomolecules. Such biochemical properties include, but are not limited to, ionic character (charge), hydrophobicity, or hydrophilicity.

The terms "biological sample" and "test sample" refer to all biological fluids and excretions isolated from any given subject. In the context of the present invention such samples include, but are not limited to, blood, blood serum, blood plasma, nipple aspirate, urine, semen, seminal fluid, seminal plasma, prostatic fluid, excreta, tears, saliva, sweat, biopsy, ascites, cerebrospinal fluid, milk, lymph, bronchial and other lavage samples, or tissue extract samples. Typically, blood, serum, plasma and bronchial lavage are preferred test samples for use in the context of the present invention.

The term "biomarker" refers to a biological molecule (or fragment of a biological molecule) that is correlated with a physical condition. For example, the biomarkers of the present invention are correlated with cancer, preferably, lung cancer and can be used as aids in the detection of the presence, absence or risk of lung cancer. Such biomarkers include, but are not limited to, biomolecules comprising nucleotides, amino acids, sugars, fatty acids, steroids, metabolites, polypeptides, proteins (such as, but not limited to, antigens and antibodies), carbohydrates, lipids, hormones, antibodies, regions of interest which serve as surrogates for biological molecules, combinations thereof (e.g., glycoproteins, ribonucleoproteins, lipoproteins) and any complexes involving any such biomolecules, such as, but not limited to, a complex formed between an antigen and an autoantibody that binds to an available epitope on said antigen. The term "biomarker" can also refer to a portion of a polypeptide (parent) sequence that comprises at least 5 consecutive amino acid residues, preferably at least 10 consecutive amino acid residues, more preferably at least 15 consecutive amino acid residues, and retains a biological activity and/or some functional characteristics of the parent polypeptide, e.g. antigenicity or structural domain characteristics.

The term "biometric parameter" refers to one or more intrinsic physical or behavioral traits used to uniquely identify patients as belonging to a well defined group or population. In the context of this invention, "biometric parameter" includes but is not limited to, physical descriptors of a patient. Examples of a biometric parameter include, but are not limited to, the height of a patient, the weight of the patient, the gender of a patient, smoking history, occupational history, exposure to carcinogens, exposure to second hand smoke, family history of lung cancer, and the like. Smoking history is usually quantified in terms of pack years (Pkyrs). As used herein, the term "Pack Years" refers to the number of years a person has smoked multiplied by the average number of packs smoked per day. A person who has smoked, on average, 1 pack of cigarettes per day for 35 years is referred to have 35 pack years of smoking history. Biometric parameter information can be obtained from a subject using routine techniques known in the art, such as from the subject itself by use of a routine patient questionnaire or health history questionnaire, etc. Alternatively, the biometric parameter can be obtained from a nurse, a nurse practitioner, physician's assistant or a physician from the subject.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a protein is preferably replaced with another amino acid residue from the same side chain family.

The phrase "Decision Tree Analysis" refers to the classical approach where a series of simple dichotomous rules (or symptoms) provides a guide through a decision tree to a final classification outcome or terminal node of the tree. Its inherently simple and intuitive nature makes recursive partitioning very amenable to a diagnostic process.

The method requires two types of variables: factor variables (X's) and response variables (Y's). As implemented, the X variables are continuous and the Y variables are categorical (Nominal). In such cases, the JMP statistical package uses an algorithm that generates a cutoff value, which maximizes the purity of the nodes. The samples are partitioned into branches or nodes based on values that are above and below this cutoff value.

For the categorical response variable, as in this case, the fitted value becomes the estimated probability for each response level. In this case the split is determined by the largest likelihood-ratio chi-square statistic ($G^2$). This has the effect of maximizing the difference in the responses between the two branches of the split. A more detailed discussion of the method and its implementation can be found in the JMP statistics and Graphics guide.

Building a tree, however, has its own concerns associated with it. A common concern is deciding the optimum size of the tree that will provide the best predictive model without over fitting the data. With this in mind, a method was developed that made use of the information that can be extracted at the various nodes of the tree to construct an ROC curve. As implemented, the method involves constructing a reference tree with enough nodes that will surely over fit the data set being modeled. Subsequently, the tree is pruned back, successively removing the worst node at each step until the minimum number of nodes is reached (two terminal nodes). This creates a series or a family of trees of decreasing complexity (fewer nodes).

The recursive partitioning program attempts to create pure terminal nodes, i.e., only specimens of one classification type are included. However, this is not always possible. Sometimes the terminal nodes have mixed populations. Thus, each terminal node will have a different probability for cancer. In a pure terminal node for cancer, the probability of being a cancer specimen will be 100% and conversely, for a pure terminal node for non-cancer, the probability of being a cancer specimen will be 0%. The probability of cancer at each terminal node is plotted against (1-probability of non-cancer) at each node.

These values are plotted to generate an ROC curve that is representative of that particular tree. The calculated AUC for each tree represents the "goodness" of the tree or model. Just as in any diagnostic application, the higher the AUC, the better the assay, or in this case the model. A plot of AUC against the tree size (number of nodes) will have as its maximum the best model for the training set. A similar procedure is carried out with a second but smaller subset of the data to validate the results. Models that have similar performance in both the training and validation sets are deemed to be optimal and are hence chosen for further analysis and/or validation.

The terms "developmental data set" or "data set" refers to the features including the complete biomarker or biomarker and biometric parameter data collected for a set of biological samples. These samples themselves are drawn from patients with known diagnosed outcomes. A feature or set of features is subjected to a statistical analysis aiming towards a classification of samples into two or more different sample groups (e.g., cancer and non cancer) correlating to the known patient outcomes. When mass spectra is used, then the mass spectra within the set can differ in their intensities, but not in their apparent molecular masses within the precision of the instrumentation.

The term "classifier" refers to any algorithm that uses the features derived for a set of samples to determine the disease associated with the sample. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of 'variable 1' larger than 'threshold 1'; then go left, else go right". Accordingly, the given feature space is partitioned into a set of rectangles with each rectangle assigned to one class.

The terms "diagnostic assay" and "diagnostic method" refer to the detection of the presence or nature of a pathologic condition. Diagnostic assays differ in their sensitivity and specificity. Subjects who test positive for lung cancer and are actually diseased are considered "true positives". Within the context of the invention, the sensitivity of a diagnostic assay is defined as the percentage of the true positives in the diseased population. Subjects having lung cancer but not detected by the diagnostic assay are considered "false negatives". Subjects who are not diseased and who test negative in the diagnostic assay are considered "true negatives". The term specificity of a diagnostic assay, as used herein, is defined as the percentage of the true negatives in the non-diseased population.

The term "discriminant analysis" refers to a set of statistical methods used to select features that optimally discriminate between two or more naturally occurring groups. Application of discriminant analysis to a data set allows the user to focus on the most discriminating features for further analysis.

The phrase "Distance From Ideal" or "DFI" refers to a parameter taken from a ROC curve that is the distance from ideal, which incorporates both sensitivity and specificity and is defined as $[(1\text{-sensitivity})^2+(1\text{-specificity})^2]^{1/2}$. DFI is 0 for an assay with performance of 100% sensitivity and 100% specificity and increases to 1.414 for an assay with 0% sensitivity and 0% specificity. Unlike the AUC which uses the complete data range for its determination, DFI measures the performance of a test at a particular point on the ROC curve. Tests with lower DFI values perform better than those with higher DFI values. DFI is discussed in detail in U.S. Patent Application Publication No. 2006/0211019 A1.

The terms "ensemble", "tree ensemble" or "ensemble classifier" can be used interchangeably and refer to a classifier that consists of many simpler elementary classifiers, e.g., an ensemble of decision trees is a classifier consisting of decision trees. The result of the ensemble classifier is obtained by combining all the results of its constituent classifiers, e.g., by majority voting that weights all constituent classifiers equally. Majority voting is especially reasonable where constituent classifiers are then naturally weighted by the frequency with which they are generated.

The term "epitope" is meant to refer to that portion of an antigen capable of being bound by an antibody that can also be recognized by that antibody. Epitopic determinants usually consist of chemically active surface groupings of molecules such as amino acids or sugar side chains and have specific three dimensional structural characteristics as well as specific charge characteristics.

The terms "feature" and "variable" may be used interchangeably and refer to the value of a measure of a characteristic of a sample. These measures may be derived from physical, chemical, or biological characteristics of the sample. Examples of the measures include but are not limited to, a mass spectrum peak, mass spectrum signal, a function of the intensity of a ROI.

Calculations of homology or sequence identity between sequences (the terms are used interchangeably herein) are performed as follows.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 95%, 99% or 100% of the length of the reference sequence amino acid residues are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (*CABIOS*, 4:11-17 (1989)) which has been incorporated into the ALIGN program (version 2.0), using a PAM 120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., *J. Mol. Biol.* 215:403-10 (1990). BLAST protein searches can be performed with the XBLAST program, score=50, wordlength=3 to obtain amino acid sequences homologous to an immunoreactive Cyclin E2 protein of the present invention. To obtain gapped alignments for comparison purposes, Gapped BLAST can be utilized as described in Altschul et al., *Nucleic Acids Res.* 25(17):3389-3402 (1997). When utilizing BLAST and Gapped BLAST programs, the default parameters of the respective programs (e.g., XBLAST and NBLAST) can be used.

As used herein, the term "immunoreactive Cyclin E2" refers to (1) a polypeptide having an amino acid sequence of any of SEQ ID NO:1, SEQ ID NO:3, SEQ ID NO:4, or SEQ ID NO:5; (2) any combinations of any of SEQ ID NO:1, SEQ ID NO:3, SEQ ID NO:4 or SEQ ID NO:5; (3) a polypeptide having an amino acid sequence that is at least 60%, preferably at least 70%, more preferably at least 75, 80, 81, 82, 83, 84, 85, 86, 87, 88, 89, 90, 91, 92, 93, 94, 95, 96, 97, 98, 99% homologous to SEQ ID NO:1, a polypeptide having an amino acid sequence that is at least 60%, preferably at least 70%, more preferably at least 75, 80, 81, 82, 83, 84, 85, 86, 87, 88, 89, 90, 91, 92, 93, 94, 95, 96, 97, 98, 99% homologous to SEQ ID NO:3, a polypeptide having an amino acid sequence that is at least 60%, preferably at least 70%, more preferably at least 75, 80, 81, 82, 83, 84, 85, 86, 87, 88, 89, 90, 91, 92, 93, 94, 95, 96, 97, 98, 99% homologous to SEQ ID NO:4, a polypeptide having an amino acid sequence that is at least 60%, preferably at least 70%, more preferably at least 75, 80, 81, 82, 83, 84, 85, 86, 87, 88, 89, 90, 91, 92, 93, 94, 95, 96, 97, 98, 99% homologous to SEQ ID NO:5 and any combinations thereof; (4) a Cyclin E2 polypeptide that exhibits similar immunoreactivity to SEQ ID NO:1, SEQ ID NO:3, SEQ ID NO:4 or SEQ ID NO:5; and (5) a polypeptide that exhibits similar immunoreactivity to SEQ ID NO:1, SEQ ID NO:3, SEQ ID NO:4 or SEQ ID NO:5.

An "isolated" or "purified" polypeptide or protein is substantially free of cellular material or other contaminating proteins from the cell or tissue source from which the protein is derived, or substantially free from chemical precursors or other chemicals when chemically synthesized. When a protein or biologically active portion thereof is recombinantly produced, it is also preferably substantially free of culture medium, namely, culture medium represents less than about 20%, more preferably less than about 10%, and most preferably less than about 5% of the volume of the protein preparation.

As used herein, the phrase "Linear Discriminate Analysis" refers to a type of analysis that provides a tool for identifying those variables or features that are best at correctly categorizing a sample and which can be implemented, for example, by the JMP™ statistical package. Using the stepwise feature of the software, variables may be added to a model until it correctly classifies all samples. Generally, the set of variables selected in this manner is substantially smaller than the original number of variables in the data set. This reduction in the number of features simplifies any following analysis, for example, the development of a more general classification engine using decision trees, artificial neural networks, or the like.

The term "lung cancer" refers to a cancer state associated with the pulmonary system of any given subject. In the context of the present invention, lung cancers include, but are not limited to, adenocarcinoma, epidermoid carcinoma, squamous cell carcinoma, large cell carcinoma, small cell carcinoma, non-small cell carcinoma, and bronchoalveolar carcinoma. Within the context of the present invention, lung cancers may be at different stages, as well as varying degrees of grading. Methods for determining the stage of a lung cancer or its degree of grading are well known to those skilled in the art.

The term "mass spectrometry" refers to the use of an ionization source to generate gas phase ions from a sample on a surface and detecting the gas phase ions with a mass spectrometer. The term "laser desorption mass spectrometry" refers to the use of a laser as an ionization source to generate gas phase ions from a sample on a surface and detecting the gas phase ions with a mass spectrometer. A preferred method of mass spectrometry for biomolecules is matrix-assisted laser desorption/ionization mass spectrometry or MALDI. In MALDI, the analyte is typically mixed with a matrix material that, upon drying, co-crystallizes with the analyte. The matrix material absorbs energy from the energy source which otherwise would fragment the labile biomolecules or analytes. Another preferred method is surface-enhanced laser desorption/ionization mass spectrometry or SELDI. In SELDI, the surface on which the analyte is applied plays an active role in the analyte capture and/or desorption. In the context of the invention the sample comprises a biological sample that may have undergone chromatographic or other chemical processing and a suitable matrix substrate.

In mass spectrometry the "apparent molecular mass" refers to the molecular mass (in Daltons)-to-charge value, m/z, of the detected ions. How the apparent molecular mass is derived is dependent upon the type of mass spectrometer used. With a time-of-flight mass spectrometer, the apparent molecular mass is a function of the time from ionization to detection.

The term "matrix" refers to a molecule that absorbs energy as photons from an appropriate light source, for example a UV/Vis or IR laser, in a mass spectrometer thereby enabling desorption of a biomolecule from a surface. Cinnamic acid derivatives including α-cyano cinnamic acid, sinapinic acid and dihydroxybenzoic acid are frequently used as energy absorbing molecules in laser desorption of biomolecules. Energy absorbing molecules are described in U.S. Pat. No. 5,719,060, which is incorporated herein by reference.

The term "normalization" and its derivatives, when used in conjunction with mass spectra, refer to mathematical methods that are applied to a set of mass spectra to remove or minimize the differences, due primarily to instrumental parameters, in the overall intensities of the spectra.

The term "region of interest" or "ROI" refers to a statistical adaptation of a subset of a mass spectrum. An ROI has fixed minimum length of consecutive signals. The consecutive signals may contain gaps of fixed maximum length depending on how the ROI is chosen. Regions of interest are related to biomarkers and can serve as surrogates to biomarkers. Regions of interest may later be determined to represent a protein, polypeptide, antigen, antibody, lipid, hormone, carbohydrate, etc.

The phrase "Receiver Operating Characteristic Curve" or "ROC curve" refers to, in its simplest application, a plot of the performance of a particular feature (for example, a biomarker or biometric parameter) in distinguishing between two populations (for example, cases (i.e., those subjects that are suffering from lung cancer) and controls (i.e., those subjects that are normal or benign for lung cancer)). The feature data across the entire population (namely, the cases and controls), is sorted in ascending order based on the value of a single feature. Then, for each value for that feature, the true positive and false positive rates for the data are calculated. The true positive rate is determined by counting the number of cases above the value for that feature under consideration and then dividing by the total number of cases. The false positive rate is determined by counting the number of controls above the value for that feature under consideration and then dividing by the total number of controls. While this definition has described a scenario in which a feature is elevated in cases compared to controls, this definition also encompasses a scenario in which a feature is suppressed in cases compared to the controls. In this scenario, samples below the value for that feature under consideration would be counted.

ROC curves can be generated for a single feature as well as for other single outputs, for example, a combination of two or more features are mathematically combined (such as, added, subtracted, multiplied, etc.) together to provide a single sum value, this single sum value can be plotted in a ROC curve. Additionally, any combination of multiple features, whereby the combination derives a single output value can be plotted in a ROC curve. These combinations of features may comprise a test. The ROC curve is the plot of the true positive rate (sensitivity) of a test against the false positive rate (1-specificity) of the test. The area under the ROC curve is a figure of merit for the feature for a given sample population and gives values ranging from 1 for a perfect test to 0.5 in which the test gives a completely random response in classifying test subjects. ROC curves provide another means to quickly screen a data set. Features that appear to be diagnostic can be used preferentially to reduce the size of large feature spaces.

The term "screening" refers to a diagnostic decision regarding the patient's disposition toward lung cancer. A patient is determined to be at high risk of lung cancer with a positive "screening test". As a result, the patient can be given additional tests, e.g., imaging, sputum testing, lung function tests, bronchoscopy and/or biopsy procedures and a final diagnosis made.

The term "signal" refers to any response generated by a biomolecule under investigation. For example, the term signal refers to the response generated by a biomolecule hitting the detector of a mass spectrometer. The signal intensity correlates with the amount or concentration of the biomolecule. The signal is defined by two values: an apparent molecular mass value and an intensity value generated as described. The mass value is an elemental characteristic of the biomolecule, whereas the intensity value accords to a certain amount or concentration of the biomolecule with the corresponding apparent molecular mass value. Thus, the "signal" always refers to the properties of the biomolecule.

The phrase "Split and Score Method" refers to a method adapted from Mor et al., *PNAS,* 102(21):7677-7682 (2005). In this method, multiple measurements are taken on all samples. A cutoff value is determined for each measurement. This cutoff value may be set to maximize the accuracy of correct classifications between the groups of interest (e.g., diseased and not diseased) or may be set to maximize the sensitivity or specificity of one group. For each measure, it is determined whether the group of interest, e.g., diseased, lies above the cutoff or below the cutoff value. For each measurement, a score is assigned to that sample whenever the value of that measurement is found to be on the diseased side of the cutoff value. After all the measurements have been taken on one sample, the scores are summed to produce a total score for the panel of measurements. It is common to equally weight all measurements such that a panel of 10 measurements might have a maximum score of 10 (each measurement having a score of either 1 or 0) and a minimum score of 0. However, it may be valuable to weight the measurements unequally with a higher individual score for more significant measures.

After the total scores are determined, once again a cutoff is determined for classifying diseased from non-diseased samples based on the panel of measurements. Here again, for a panel of measurements with a maximum score of 10 and a minimum score of 0, a cutoff may be chosen to maximize sensitivity (score of 0 as cutoff), or to maximize specificity (score of 10 as cutoff), or to maximize accuracy of classification (score in between 0-10 as cutoff).

As used herein, the phrase "Weighted Scoring Method" refers to a method that involves converting the measurement of one biomarker or a biometric parameter (collectively referred to herein as a "marker(s)") that is identified and quantified in a test sample into one of many potential scores. The scores are obtained using the following equation:

$$\text{Score} = \text{AUC} \cdot \text{factor}/(1-\text{specificity})$$

where the "factor" is an integer (such as 0, 1, 2, 3, 4, 5, 6, 7, 8, 9, 10, 11, 12, 13, 14, 15, 16, 17, 18, 19, 20, 21, 22, 23, 24, 25, etc.) and the "specificity" is a chosen value that is less than or equal to 1. The magnitude of "factor" increases for markers having improved clinical performance, such as, but not limited to, higher AUC values, relatively small standard deviations, high specificity or sensitivity or low DFI. Thereupon, the measurement of one marker can be converted into as many or as few scores as desired. This method is based on the Receiver Operator Characteristic curve which reflects the marker/test performance in the population of interest. The ROC curve is the plot of the true positive rate (sensitivity) of a test against the false positive rate (1-specificity) of the test. Each point on the curve represents a single value of the feature/test (marker) being measured. Therefore, some values will have a low false positive rate in the population of interest (namely, subjects at risk of developing lung cancer) while other values of the feature will have high false positive rates in that population. This method provides higher scores for feature values (namely, biomarkers or biometric parameters) that have low false positive rates (thereby having high specificity) for the population of subjects of interest. The method involves choosing desired levels of false positivity (1-specificity) below which the test will result in an increased score. In other words, markers that are highly specific are given a greater score or a greater range of scores than markers that are less specific.

As used herein, the term "subject" refers to an animal, preferably a mammal, including a human or non-human. The terms patient and subject may be used interchangeably herein.

The phrase "Ten-fold Validation of DT Models" refers to the fact that good analytical practice requires that models be validated against a new population to assess their predictive value. In lieu of a new population, the data can be divided into independent training sets and validation sets. Ten random subsets are generated for use as validation sets. For each validation set, there is a corresponding independent training set having no samples in common. Ten DT models are generated from the ten training sets as described above and interrogated with the validation sets.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

The term "Transformed Logistic Regression Model" refers to a model, which is also implemented in the JMP™ statistical package, that provides a means of combining a number of features and allowing a ROC curve analysis. This approach is best applied to a reduced set of features as it assumes a simplistic model for the relationship of the features to one another. A positive result suggests that more sophisticated classification methods should be successful. A negative result while disappointing does not necessarily imply failure for other methods.

Cyclin E2 Polypeptides

In one embodiment, the present invention relates to isolated or purified immunoreactive Cyclin E2 polypeptides or biologically active fragments thereof that can be used as immunogens or antigens to raise or test (or more generally, to bind) antibodies that can be used in the methods described herein. The immunoreactive Cyclin E2 polypeptides of the present invention can be isolated from cells or tissue sources using standard protein purification techniques. Alternatively, the isolated or purified immunoreactive Cyclin E2 polypeptides and biologically active fragments thereof can be produced by recombinant DNA techniques or synthesized chemically. The isolated or purified immunoreactive Cyclin E2 polypeptides of the present invention have the amino acid sequences shown in SEQ ID NO:1, SEQ ID NO:3, SEQ ID NO:4 and SEQ ID NO:5. SEQ ID NO:1 is the amino acid sequence of a cDNA expressed form of human Cyclin E2 (Genbank Accession BC007015.1). SEQ ID NO:3 is a 38 amino acid sequence that comprises C-terminus of BC007015.1 plus one amino acid (cysteine) and is also referred to herein as "E2-1". SEQ ID NO:4 is 37 amino acids in length and is identical to SEQ ID NO:3 except that SEQ ID NO:4 does not contain, at its amino terminus, the very first cysteine of SEQ ID NO:3. SEQ ID NO:5 is a 19 amino acid sequence that comprises the C-terminus of BC007015.1 and is referred to herein as "E2-2". As described in more detail in the Examples, the immunoreactivity SEQ ID NO:1 was compared with the immunoreactivity of SEQ ID NO:2. SEQ ID NO:2 is another cDNA expressed form of human cyclin E2 (Genbank Accession BC020729.1). SEQ ID NO:1 was found to show strong immunoreactivity with several pools of cancer samples and exhibited much lower reactivity with benign and normal (non-cancer) pools. In contrast, SEQ ID NO:2 showed little reactivity with any cancer or non-cancer pooled samples. The immunoreactivity of SEQ ID NO:1 was determined to be the result of the first 37 amino acids present at the C-terminus of SEQ ID NO:1 that are not present in SEQ ID NO:2. SEQ ID NOS:3 and 5, which are both derived from the C-terminus of SEQ ID NO:1, have been found to show strong immunoreactivity between cancer or non-cancer pools. Therefore, antibodies generated against any of SEQ ID NO:1, SEQ ID NO:3, SEQ ID NO:4 and SEQ ID NO:5 or any combinations of these sequences (such as, antibodies generated against SEQ ID NO:1 and SEQ ID NO:3, antibodies generated against SEQ ID NO:1 and SEQ ID NO:4, antibodies generated against SEQ ID NO:1 and SEQ ID NO:5, antibodies generated against SEQ ID NO:1, SEQ ID NO:3 and SEQ ID NO:4, antibodies generated against SEQ ID NO:1, SEQ ID NO:3 and SEQ ID NO:5, antibodies generated against SEQ ID NO:1, SEQ ID NO:4 and SEQ ID NO:5, antibodies generated against SEQ ID NO:1, SEQ ID NO:3, SEQ ID NO:4 and SEQ ID NO:5, antibodies generated against SEQ ID NO:3 and SEQ ID NO:4, antibodies generated against SEQ ID NO:3 and SEQ ID NO:5, antibodies generated against SEQ ID NO: 3, SEQ ID NO:4 and SEQ ID NO:5, antibodies generated against SEQ ID NO:4 and SEQ ID NO:5 (all collectively referred to herein as "anti-Cyclin E2")) can be used in the methods described herein. For example, such antibodies can be subject antibodies generated against any of SEQ ID NO:1, SEQ ID NO:3, SEQ ID NO:4 and SEQ ID NO:5 or any combinations of these sequences. Such antibodies can be included in one or more kits for use in the methods of the present invention described herein.

The present invention also encompasses polypeptides that differ from the polypeptides described herein (namely, SEQ ID NO:1, SEQ ID NO:3, SEQ ID NO:4 and SEQ ID NO:5) by one or more conservative amino acid substitutions. Additionally, the present invention also encompasses polypeptides that have an overall sequence similarity (identity) or homology of at least 60%, preferably at least 70%, more preferably at least 75, 80, 81, 82, 83, 84, 85, 86, 87, 88, 89, 90, 91, 92, 93, 94, 95, 96, 97, 98, 99% or more, with a polypeptide of having the amino acid sequence of SEQ ID NO:1, SEQ ID NO:3, SEQ ID NO:4 and SEQ ID NO:5.

Use of Biomarkers and Biometric Parameters in Detecting the Presence or Risk of Lung Cancer In another embodiment, the present invention relates to methods that effectively aid in the differentiation between normal subjects and those with cancer or who are at risk of developing a medical condition. The medical condition is preferably cancer, even more preferably lung cancer. Normal subjects are considered to be those not diagnosed with any medical condition, such as cancer, more preferably those not diagnosed with lung cancer.

The present invention advantageously provides rapid, sensitive and easy to use methods for aiding in the diagnosis of a medical condition, preferably, cancer, and even more preferably, lung cancer. Moreover, the present invention can be used to identify individuals at risk for developing a medical condition, to screen subjects at risk for a medical condition and to monitor patients diagnosed with or being treated for a medical condition. The invention can also be used to monitor the efficacy of treatment of a patient being treated for a medical condition. Preferably, the medical condition is cancer and even more preferably, lung cancer. As used throughout this specification, particularly in connection with the methods described herein, subjects having a medical condition of interest (such as subjects having lung cancer) are considered to be the same as those subjects having a high risk of a medical condition of interest (such as subjects having a high risk of lung cancer).

In general, the methods of the present invention involve obtaining a test sample from a subject. Typically, a test sample is obtained from a subject and processed using standard methods known to those skilled in the art. For blood specimens and serum or plasma derived therefrom, the sample can be conveniently obtained from the antecubetal vein by veinipuncture, or, if a smaller volume is required, by a finger stick. In both cases, formed elements and clots are removed by centrifugation. Urine or stool can be collected directly from the patient with the proviso that they be processed rapidly or stabilized with preservatives if processing cannot be performed immediately. More specialized samples such as bronchial washings or pleural fluid can be collected during bronchoscopy or by transcutaneous or open biopsy and processed similarly to serum or plasma once particulate materials have been removed by centrifugation.

After processing, the test sample obtained from the subject is interrogated for the presence and quantity of one or more biomarkers that can be correlated with a diagnosis of lung cancer. Specifically, Applicants have found that the detection and quantification of one or more biomarkers or a combination of biomarkers and biometric parameters (such as at least 1 biomarker, at least 1 biomarker and at least 1 biometric parameter, at least 2 biomarkers, at least 2 biomarkers and 1 biometric parameter, at least 1 biomarker and at least 2 biometric parameters, at least 2 biomarkers and at least 2 biometric parameters, at least 3 biomarkers, etc.) are useful as an aid in diagnosing lung cancer in a patient. The one or more biomarkers identified and quantified in the methods described herein can be contained in one or more panels. The number of biomarkers comprising a panel can include 1 biomarker, 2 biomarkers, 3 biomarkers, 4 biomarkers, 5 biomarkers, 6 biomarkers, 7 biomarkers, 8 biomarkers, 9 biomarkers, 10 biomarkers, 11 biomarkers, 12 biomarkers, 13 biomarkers, 14 biomarkers, 15 biomarkers, 16 biomarkers, 17 biomarkers, 18 biomarkers, 19 biomarkers, 20 biomarkers, etc. However, when choosing biomarkers for inclusion in a panel, such biomarkers should be selected for complementarity so that the combinations of biomarkers selected provide for a better performance (in terms of AUC, DFI sensitivity and specificity or any combination of AUC, DFI, sensitivity and specificity) than individual combinations.

As mentioned above, after obtaining a test sample, the methods of the present invention involve identifying the presence of and then quantifying one or more biomarkers in a test sample. Any biomarkers that are useful or are believed to be useful for aiding in the diagnosis of a patient suspected of being at risk of lung cancer can be quantified in the methods described herein and can be contained in one or more panels. Thereupon, in one aspect, the panel can include one or more biomarkers. Examples of biomarkers that can be included in a panel, include, but are not limited to, anti-p53, anti-TMP21, anti-NY-ESO-1, anti-HDJ1, anti-Niemann-Pick C1-Like protein 1, C terminal peptide-domain (anti-NPC1L1C-domain), anti-TMOD1, anti-CAMK1, anti-RGS1, anti-PACSIN1, anti-RCV1, anti-MAPKAPK3, anti-Cyclin E2 (namely, at least one immunoreactive antibody against SEQ ID NO:1, SEQ ID NO:3, SEQ ID NO:4, SEQ ID NO:5 or any combinations thereof), antigens, such as, but not limited to, carcinoembryonic antigen (CEA), cancer antigen 125 (CA125), cancer antigen 15-3 (CA15-3), progastrin releasing peptide (proGRP), squamous cell antigen (SCC), cytokeratin 8, cytokeratin 19 peptides or proteins (also referred to just as "CK-19, CYFRA 21-1, Cyfra" herein), and cytokeratin 18 peptides or proteins (CK-18, TPS), carbohydrate antigens, such as cancer antigen 19-9 (CA19-9), which is the Lewis A blood group with added sialic acid residues, serum amyloid A, alpha-1-anti-trypsin, apolipoprotein CIII and thymosin β4 (Tβ4), regions of interest, such as, but not limited to, Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959 and any combinations thereof. Optionally, the panel used in the above method can comprise quantifying the amount of two or more biomarkers, three or more biomarkers, four or more biomarkers, five or more biomarkers, six or more biomarkers, seven or more biomarkers, eight biomarkers, nine or more biomarkers, ten or more biomarkers, eleven or more biomarkers, twelve or more biomarkers, thirteen or more biomarkers, fourteen or more biomarkers, fifteen or more biomarkers, sixteen or more biomarkers, seventeen or more biomarkers, eighteen or more biomarkers, nineteen or more biomarkers or twenty biomarkers or more, etc.

In another aspect, the panel can contain at least one antibody, at least one antigen, at least one region of interest, at least one antigen and at least one antibody, at least one antigen and at least one region of interest and at least one antibody and at least one region of interest. Examples of at least one antibody that can be included in the panel, include, but are not limited to, anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 or anti-Cyclin E2. Examples of at least one antigen that can be included in the panel are, but are not limited to, cytokeratin 8, cytokeratin 19, cytokeratin 18, CEA, CA125, SCC, CA19-9, proGRP, serum amyloid A, alpha-1-anti-trypsin, apolipoprotein CIII and Tβ4. Examples of at least one region of interest that can be included in the panel include, but are not limited to, Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959. Additionally, certain regions of interest have been found to be highly correlated (meaning that these regions of interest have high correlation coefficients among one another) with certain other regions of interest and thus are capable of being substituted for one another within the context of the present invention. Specifically, these highly correlated regions of interest have been assembled into certain correlating families or "groups". The regions of interest contained within these "groups" can be substituted for one another in the methods and kits of the present invention. These correlating families or "groups" of regions of interest are described below:

Group A: The regions of interest: Pub3448 and Pub3493.
Group B: The regions of interest: Pub4487 and Pub4682.
Group C: The regions of interest: Pub8766, Pub8930, Pub9142, Pub9216, Pub9363, Pub9433, Pub9495, Pub9648 and Pub9722.
Group D: The regions of interest: Pub5036, Pub5139, Pub5264, Pub5357, Pub5483, Pub5573, Pub5593, Pub5615, Pub6702, Pub6718, Pub10759, Pub11066, Pub12193, Pub13412, Acn10679 and Acn10877.
Group E: The regions of interest: Pub6391, Pub6533, Pub6587, Pub6798, Pub9317 and Pub13571.
Group F: The regions of interest: Pub7218, Pub7255, Pub7317, Pub7413, Pub7499, Pub7711, Pub14430 and Pub15599.
Group G: The regions of interest: Pub8496, Pub8546, Pub8606, Pub8662, Pub8734, Pub17121 and Pub17338.
Group H: The regions of interest: Pub6249, Pub12501 and Pub12717.
Group I: The regions of interest: Pub5662, Pub5777, Pub5898, Pub11597 and Acn11559.
Group J: The regions of interest: Pub7775, Pub7944, Pub7980, Pub8002 and Pub15895.
Group K: The regions of interest: Pub17858, Pub18422, Pub18766 and Pub18986.
Group L: The regions of interest: Pub3018, Pub3640, Pub3658, Pub3682, Pub3705, Pub3839, Hic2451, Hic2646, Hic3035, Tfa3016, Tfa3635 and Tfa4321.
Group M: The regions of interest: Pub2331 and Tfa2331.
Group N: The regions of interest: Pub4557 and Pub4592.
Group O: The regions of interest: Acn4631, Acn5082, Acn5262, Acn5355, Acn5449 and Acn5455.
Group P: The regions of interest: Acn6399, Acn6592, Acn8871, Acn9080, Acn9371 and Acn9662.
Group Q: The regions of interest: Acn9459 and Acn9471.
Group R: The regions of interest: Hic2506, Hic2980, Hic3176 and Tfa2984.
Group S: The regions of interest: Hic2728 and Hic3276.
Group T: The regions of interest: Hic6381, Hic6387, Hic6450, Hic6649, Hic6816 and Hic6823.
Group U: The regions of interest: Hic8791 and Hic8897.
Group V: The regions of interest: Tfa6453 and Tfa6652.
Group W: The regions of interest: Hic6005 and Hic5376.
Group X: The regions of interest: Pub4713, Pub4750 and Pub4861.

Preferred panels that can be used in the methods of the present invention, include, but are not limited to:

1. A panel comprising at least two biomarkers, wherein said biomarkers are at least one antibody and at least one antigen. This panel can also further comprise additional biomarkers such as at least one region of interest.

2. A panel comprising at least one biomarker, wherein said biomarker comprises anti-Cyclin E2. Additionally, the panel can also optionally further comprise additional biomarkers, such as, (a) at least one antigen; (b) at least one antibody; (c) at least one antigen and at least one antibody; (d) at least one region of interest; (e) at least one antigen and at least one region of interest; (f) at least one antibody and at least one region of interest; or (g) at least one antigen, at least one antibody and at least one region of interest.

3. A panel comprising at least one biomarker, wherein the biomarker is selected from the group consisting of: cytokeratin 8, cytokeratin 19, cytokeratin 18, CEA, CA125, SCC, proGRP, serum amyloid A, alpha-1-anti-trypsin and apolipoprotein CIII. The panel can optionally further comprise additional biomarkers, such as, at least one antibody, at least one region of interest and at least one region of interest and at least one antibody in the test sample.

4. A panel comprising at least one biomarker, wherein the biomarker is at least one region of interest is selected from the group consisting of: Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959. The panel can also optionally further comprise additional biomarkers, such as, at least one antigen, at least one antibody and at least one antigen and at least one antibody in the test sample.

5. A panel comprising at least one biomarker in a panel, wherein the at least one biomarker is selected from the group consisting of: cytokeratin 8, cytokeratin 19, cytokeratin 18, CEA, CA 125, SCC, proGRP, serum amyloid A, alpha-1-antitrypsin, apolipoprotein CIII, Acn6399, Acn9459, Pub11597, Pub4789, TFA2759, TFA9133, Pub3743, Pub8606, Pub4487, Pub4861, Pub6798, Pub6453, Pub2951, Pub2433, Pub17338, TFA6453 and HIC3959. The panel can also optionally further comprise additional biomarkers such as at least one antibody. Preferred panels are panels comprising: (a) cytokeratin 19, CEA, ACN9459, Pub11597, Pub4789 and TFA2759; (b) cytokeratin 19, CEA, ACN9459, Pub11597, Pub4789, TFA2759 and TFA9133; (c) cytokeratin 19, CA 19-9, CEA, CA 15-3, CA125, SCC, cytokeratin 18 and ProGRP; (d) Pub11597, Pub3743, Pub8606, Pub4487, Pub4861, Pub6798, Tfa6453 and Hic3959; and (e) cytokeratin 19, CEA, CA125, SCC, cytokeratin 18, ProGRP, ACN9459, Pub11597, Pub4789, TFA2759, TFA9133.

6. A panel comprising at least two biomarkers in a panel, wherein the at least two biomarkers are selected from the group consisting of: anti-p53, anti-NY-ESO-1, anti-MAPKAPK3, one or more antibodies against immunoreactive Cyclin E2, cytokeratin 19, CEA, CA125 and ProGRP. The panel can also comprise at least three biomarkers selected from the above group, at least four biomarkers selected from the above group, at least five biomarkers selected from the above group, at least six biomarkers selected from the above group, at least seven biomarkers selected from the above group or all eight of the above described biomarkers (namely, each of anti-p53, anti-NY-ESO-1, anti-MAPKAPK3, one or more antibodies against immunoreactive Cyclin E2, cytokeratin 19, CEA, CA 125 and ProGRP). Preferably, the panel comprises all eight of the above-described biomarkers.

The presence and quantity of one or more biomarkers in the test sample can be obtained and quantified using routine techniques known to those skilled in the art. For example, methods for quantifying antigens or antibodies in test samples are well known to those skilled in the art. For example, the presence and quantification of one or more antigens or antibodies in a test sample can be determined using one or more immunoassays that are known in the art. Immunoassays typically comprise: (a) providing an antibody (or antigen) that specifically binds to the biomarker (namely, an antigen or an antibody); (b) contacting a test sample with the antibody or antigen; and (c) detecting the presence of a complex of the antibody bound to the antigen in the test sample or a complex of the antigen bound to the antibody in the test sample.

To prepare an antibody that specifically binds to an antigen, purified antigens or their nucleic acid sequences can be used. Nucleic acid and amino acid sequences for antigens can be obtained by further characterization of these antigens. For example, antigens can be peptide mapped with a number of enzymes (e.g., trypsin, V8 protease, etc.). The molecular weights of digestion fragments from each antigen can be used to search the databases, such as SwissProt database, for sequences that will match the molecular weights of digestion fragments generated by various enzymes. Using this method, the nucleic acid and amino acid sequences of other antigens can be identified if these antigens are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 and U.S. Pat. No. 5,792,664. The ladder is then analyzed by mass spectrometry. The difference in the masses of the ladder fragments identify the amino acid removed from the end of the molecule.

If antigens are not known proteins in the databases, nucleic acid and amino acid sequences can be determined with knowledge of even a portion of the amino acid sequence of the antigen. For example, degenerate probes can be made based on the N-terminal amino acid sequence of the antigen. These probes can then be used to screen a genomic or cDNA library created from a sample from which an antigen was initially detected. The positive clones can be identified, amplified, and their recombinant DNA sequences can be subcloned using techniques which are well known. See, for example, *Current Protocols for Molecular Biology* (Ausubel et al., Green Publishing Assoc. and Wiley-Interscience 1989) and *Molecular Cloning: A Laboratory Manual,* 2nd Ed. (Sambrook et al., Cold Spring Harbor Laboratory, NY 1989).

Using the purified antigens or their nucleic acid sequences, antibodies that specifically bind to an antigen can be prepared using any suitable methods known in the art (See, e.g., Coligan, Current Protocols in Immunology (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975)). Such techniques include, but are not limited to, antibody preparation by selection of antibodies from libraries of recombinant antibodies in phage or similar vectors, as well as preparation of polyclonal and monoclonal antibodies by immunizing rabbits or mice (See, e.g., Huse et al., *Science* 246:1275-1281 (1989); Ward et al., *Nature* 341:544-546 (1989)).

After the antibody is provided, an antigen can be detected and/or quantified using any of a number of well recognized immunological binding assays (See, for example, U.S. Pat. Nos. 4,366,241, 4,376,110, 4,517,288, and 4,837,168). Assays that can be used in the present invention include, for example, an enzyme linked immunosorbent assay (ELISA), which is also known as a "sandwich assay", an enzyme immunoassay (EIA), a radioimmunoassay (RIA), a fluoroimmunoassay (FIA), a chemiluminescent immunoassay (CLIA) a counting immunoassay (CIA), a filter media enzyme immunoassay (MEIA), a fluorescence-linked immunosorbent assay (FLISA), agglutination immunoassays and multiplex fluorescent immunoassays (such as the Luminex™ LabMAP), etc. For a review of the general immunoassays, see also, *Methods in Cell Biology: Antibodies in Cell Biology*, volume 37 (Asai, ed. 1993); *Basic and Clinical Immunology* (Stites & Terr, eds., 7th ed. 1991).

Generally, a test sample obtained from a subject can be contacted with the antibody that specifically binds an antigen. Optionally, the antibody can be fixed to a solid support prior to contacting the antibody with a test sample to facilitate washing and subsequent isolation of the complex. Examples of solid supports include glass or plastic in the form of, for example, a microtiter plate, a glass microscope slide or cover slip, a stick, a bead, or a microbead. Antibodies can also be attached to a probe substrate or ProteinChip™ array described as above (See, for example, Xiao et al., *Cancer Research* 62: 6029-6033 (2001)).

After incubating the sample with antibodies, the mixture is washed and the antibody-antigen complex formed can be detected. This can be accomplished by incubating the washed mixture with a detection reagent. This detection reagent may be, for example, a second antibody which is labeled with a detectable label. In terms of the detectable label, any detectable label known in the art can be used. For example, the detectable label can be a radioactive label (such as, e.g., $^{3}$H, $^{125}$I, $^{35}$S, $^{14}$C, $^{32}$P, and $^{33}$P), an enzymatic label (such as, for example, horseradish peroxidase, alkaline phosphatase, glucose 6-phosphate dehydrogenase, and the like), a chemiluminescent label (such as, for example, acridinium esters, acridinium thioesters, acridinium sulfonamides, phenanthridinium esters, luminal, isoluminol and the like), a fluorescence label (such as, for example, fluorescein (for example, 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (for example, zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the antigen are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, biomarker (antigen), volume of solution, concentrations and the like. Usually the assays will be carried out at ambient temperature, although they can be conducted over a range of temperatures, such as 10° C. to 40° C.

Immunoassay techniques are well-known in the art, and a general overview of the applicable technology can be found in Harlow & Lane, supra.

The immunoassay can be used to determine a test amount of an antigen in a sample from a subject. First, a test amount of an antigen in a sample can be detected using the immunoassay methods described above. If an antigen is present in the sample, it will form an antibody-antigen complex with an antibody that specifically binds the antigen under suitable incubation conditions described above. The amount of an antibody-antigen complex can be determined by comparing to a standard. The AUC for the antigen can then be calculated using techniques known, such as, but not limited to, a ROC analysis. Alternatively, the DFI can be calculated. If the AUC is greater than about 0.5 or the DFI is less than about 0.5, the immunoassay can be used to discriminate subjects with disease or risk of disease (such as cancer, preferably, lung cancer) from normal (or benign) subjects.

Immunoassay kits for a number of antigens are commercially available. For example, kits for quantifying Cytokeratin 19 are available from F. Hoffmann-La Roche Ltd. (Basel, Switzerland) and Brahms Aktiengesellschaft (Hennigsdorf, Germany), kits for quantifying Cytokeratin 18 are available from IDL Biotech AD (Bromma, Sweden) and from Diagnostic Products Corporation (Los Angeles, Calif.), kits for quantifying CA125, CEA SCC and CA19-9 are each available from Abbott Diagnostics (Abbott Park, Ill.) and from F. Hoffman-La Roche Ltd., kits for quantifying serum amyloid A and apolipoprotein CIII are available from Linco Research, Inc. (St. Charles, Mo.), kits for quantifying ProGRP are available from Advanced Life Science Institute, Inc. (Wako, Japan) and from IBL Immuno-Biological Laboratories (Hamburg, Germany), kits for quantifying alpha 1 antitrypsin are available from Autoimmune Diagnostica GMBH (Strassberg, Germany) and GenWay Biotech, Inc. (San Diego, Calif.) and kits for quantifying Tβ4 are available from ALPCO (Salem, N.H.).

The presence and quantification of one or more antibodies in a test sample can be determined using immunoassays similar to those described above. Such immunoassays are performed in a similar manner to the immunoassays described above, except for the fact that the roles of the antibody and antigens in the assays described above are reversed. For example, one type of immunoassay that can be performed is an autoantibody bead assay. In this assay, an antigen, such as the commercially available antigen p53 (which can be purchased from BioMol International L.P., Plymouth Landing, Pa.), can be fixed to a solid support, for example, a bead, a plastic microplate, a glass microscope slide or cover slip or a membrane made of a material such as nitrocellulose which binds protein antigens, using routine techniques known in the art or using the techniques and methods described in Example 3 herein. Alternatively, if an antigen is not commercially available, then the antigen may be purified from cancer cell lines (preferably, lung cancer cell lines) or a subject's own cancer tissues (preferably, lung cancer tissues) (See, S-H Hong, et al., *Cancer Research* 64: 5504-5510 (2004)) or expressed from a cDNA clone (See, Y-L Lee, et al., *Clin. Chim. Acta* 349: 87-96 (2004)). The bead containing the antigen is then contacted with the test sample. After incubating the test sample with the bead containing the bound antigen, the bead is washed and any antibody-antigen complex formed is detected. This detection can be performed as described above, namely, by incubating the washed bead with a detection reagent. This detection reagent may be for example, a second antibody (such as, but not limited to, anti-human immunoglobulin G (IgG), anti-human immunoglobulin A (IgA), anti-human immunoglobulin M (IgM)) that is labeled with a detectable label. After detection, the amount of antibody-antigen complex can be determined by comparing the signal to that generated by a standard, as described above. Alternatively, the antibody-antigen complex can be detected by taking advantage of the multivalent nature of immunoglobulins. Instead of reacting the antibody-antigen complex with an anti-human antibody, the antibody-antigen complex can be exposed to a soluble antigen that is labeled with a detectable label that contains the same epitope as the antigen attached to the solid phase. Any unoccupied antibody binding sites will bind to the soluble antigen (that is labeled with the detectable label). After washing, the detectable label is detected using routine techniques known to those of ordinary skill in the art. Either of the above-described methods allow for the sensitive and specific quantification of a specific antibody in a test sample. The AUC for the antibody (and hence, the utility of the antibody, such as an autoantibody, for detecting lung cancer in a subject) can then be calculated using routine techniques known to those skilled in the art, such as, but not limited to, a ROC analysis. Alternatively, the DFI can be calculated. If the AUC is greater than about 0.5 or the DFI is less than about 0.5, the immunoassay can be used to discriminate subjects with disease or risk of disease (such as cancer, preferably, lung cancer) from normal (or benign) subjects.

The presence and quantity of regions of interest can be determined using mass spectrometric techniques. Using mass spectroscopy, Applicants have found 212 regions of interest that are useful as an aid in diagnosing and screening of lung cancer in test samples. Specifically, when mass spectrometric techniques are used to detect and quantify one or more biomarkers in a test sample, the test sample must first be prepared for mass spectrometric analysis. Sample preparation can take place in a variety of ways, but the most commonly used involve contacting the sample with one or more adsorbents attached to a solid phase. The adsorbents can be anionic or cationic groups, hydrophobic groups, metal chelating groups with or without a metal ligand, antibodies, either polyclonal or monoclonal, or antigens suitable for binding their cognate antibodies. The solid phase can be a planar surface made of metal, glass, or plastic. The solid phase can also be of a microparticulate nature, either microbeads, amorphous particulates, or insoluble polymers for increased surface area. Furthermore the microparticulate materials can be magnetic for ease of manipulation. The biomarkers of interest are adsorbed to the solid phase and the bulk molecules removed by washing. For mass analysis, the biomarkers of interest are eluted from the solid phase with a solvent that reduces the affinity of the biomarker for the adsorbent. The biomarkers are then introduced into the mass spectrometer for analysis. Preferably, outlying spectra are identified and disregarded in evaluating the spectra. Additionally, the immunoassays, such as those described above can also be used. Upon completion of an immunoassay, the analyte can be eluted from the immunological surface and introduced into the mass spectrometer for analysis.

Once the test sample is prepared, it is introduced into a mass analyzer. Laser desorption ionization (e.g., MALDI or SELDI) is a common technique for samples that are presented in solid form. In this technique, the sample is co-crystallized on a target plate with a matrix efficient in absorbing and transferring laser energy to the sample. The created ions are separated, counted, and calibrated against ions of known mass and charge. The mass data collected for any sample is an ion count at a specific mass/charge (m/z) ratio. It is anticipated that different sample preparation methods and different ionization techniques will yield different spectra.

Qualifying tests for mass spectrum data typically involve a rigorous process of outlier analysis with minimal pre-processing of the original data. The process of identifying outliers begins with the calculation of the total ion current (TIC) of the raw spectrum. No smoothing or baseline correction algorithms are applied to the raw spectra prior to the TIC calculation. The TIC is calculated by summing up the intensities at each m/z value across the detected mass (m/z) range. This screens for instrument failures, sample spotting problems, and other similar defects. In addition to the TIC, the average % CV (percent coefficient of variation) across the whole spectrum for each sample is calculated. Using the number of replicate measurements for each sample, a % CV is calculated at every m/z value across the detected mass range. These % CVs are then averaged together to get an average % CV that is representative for that particular sample. The average % CV may or may not be used as a first filtering step for identifying outliers. In general, replicates with high average % CVs (greater than 30% or any other acceptable value) indicate poor reproducibility.

As described above, the calculated TIC and the average % CV of each spectrum could be used as predictors for qualifying the reproducibility and the "goodness" of the spectra. However, while these measurements do provide a good descriptor for the bulk property of the spectrum, they do not give any information on the reproducibility of the salient features of the spectra such as the individual intensities at each m/z value. This hurdle was overcome by an adaptation of the Spectral Contrast Angle (SCA) calculations reported by Wan et. al. (*J. Am. Soc. Mass Spectrom.* 2002, 13, 85-88). In the SCA calculations, the whole spectrum is treated as a vector whose components are the individual m/z values. With this interpretation, the angle theta ($\theta$) between the two vectors is given by the standard mathematical formula $$\cos(\theta) = v_1 \cdot v_2 / (\sqrt{v_1 \cdot v_1} * \sqrt{v_2 \cdot v_2}).$$

Theta will be small, near zero, for similar spectra.

In use, the total number of calculations and comparisons are reduced by first calculating an average spectrum for either the sample replicates or for all the samples within a particular group (e.g., Cancers). Next, an SCA is calculated between each spectrum and the calculated average spectrum. Spectra that differ drastically from the average spectrum are deemed outliers, provided, they meet the criteria described below.

Using more than one predictor to select outliers is preferable because one predictor is not enough to completely describe a mass spectrum. A multivariate outlier analysis can be carried out using multiple predictors. These predictors could be, but are not limited to, the TIC, the average % CVs, and SCA. Using the JMP™ statistical package (SAS Institute Inc., Cary, N.C.), the Mahalanobis distances are calculated for each replicate measurement in the group (e.g., Cancer). A critical value (not a confidence limit) can be calculated such that about 95% of the observations fall below this value. The remaining 5% that fall above the critical value are deemed outliers and precluded from further analysis.

After qualification of mass spectral data, the spectra are usually normalized, scaling the intensities so that the TIC is the same for all spectra in the data set or scaling the intensities relative to one peak in all the spectra.

After normalization, the mass spectra are reduced to a set of intensity features. In other applications, these reduce to a list of spectral intensities at m/z values associated with biomolecules. Preferably, another type of feature, the region of interest or ROI, is used.

Regions of interest are products of a comparison between two or more data sets of interest. These data sets represent the groups of interest (e.g., diseased and not diseased). A t-test is performed on the intensity values across all samples at each m/z. Those m/z values with t-test p-values less than an operator-specified threshold are identified. Of the identified m/z values, those that are contiguous are grouped together and defined as a region of interest. The minimum number of contiguous m/z values required to form an ROI and any allowed gaps within that contiguous group can be user defined. Another qualifier for the ROI is the absolute value of the logarithm of the ratio of the means of the two groups. When this value is greater than some threshold cutoff value, say 0.6 when base 10 logarithms are used, the mass-to-charge location becomes a candidate of inclusion in an ROI. The advantage to using the ROI method is that it not only flags differences in the pattern of high intensities between the spectra of the two classes but also finds more subtle differences like shoulders and very low intensities that would be missed by peak finding methods.

Once the region of interest has been determined, the mean or median m/z value of the range of the ROI is often used as an identifier for the region. Each region is a potential marker differentiating the data sets. A variety of parameters (e.g., total intensity, maximum intensity, median intensity, or average intensity) can be extracted from the sample data and associated with the ROI. Thus, each sample spectrum has been reduced from many thousands of m/z, intensity pairs to 212 ROIs and their identifier, intensity function pairs. These descriptors are used as input variables for the data analysis techniques.

Optionally, either before obtaining a test sample or after obtaining a test sample and prior to identifying and quantifying one or more biomarkers in a test sample or after identifying and quantifying one or more biomarkers in a test sample, the methods of the present invention can include the step of obtaining a value of at least one biometric parameter from a subject. For example, 1, 2, 3, 4, 5, 6, 7, 8, 9, 10, etc. biometric parameters can be obtained from a subject. Alternatively, the methods of the present invention do not have to include a step of obtaining any values for any biometric parameters from a subject. The preferred biometric parameter obtained from a subject is the smoking history of the subject, specifically, the subject's pack-years of smoking. Other biometric parameters that can be obtained from the subject include, but are not limited to, age, carcinogen exposure, gender, family history of smoking, etc.

As mentioned above, in the methods of the present invention, the test sample is analyzed to determine the presence of one or more biomarkers contained in the panel. If a biomarker is determined to be present in the test sample, then the amount of each such detected biomarker is quantified (using the techniques described previously herein). Once the amount of each biomarker in the test sample is quantified, then the amount of each biomarker quantified is compared to a predetermined cutoff (which is typically, a value or a number, such as an integer, and is alternatively referred to herein as a "cutoff" or "split point") for that specific biomarker. The predetermined cutoff employed in the methods of the present invention can be determined using routine techniques known in the art, such as, but not limited to, multi-variate analysis (See FIG. 1), Transformed Logistic Regression, a Split and Score Method or any combinations thereof. For example, when the Split and Score Method is used, the value or number of the predetermined cutoff will depend upon the desired result to be achieved. If the desired result to be achieved is to maximize the accuracy of correct classifications of each marker in a group of interest (namely, correctly identifying those subjects at risk for developing lung cancer and those that are not at risk for developing lung cancer), then a specific value or number will be chosen for the predetermined cutoff for that biomarker based on that desired result. In contrast, if the desired result is to maximize the sensitivity of each marker, then a different value or number for the predetermined cutoff may be chosen for that biomarker based on that desired result. Likewise, if the desired result is to maximize the specificity of each marker, then a different value for the predetermined cutoff may be chosen for that biomarker based on that desired result. Once the amount of any biomarkers present in the test sample is quantified, this information can be used to generate ROC Curves, AUC and other information that can be used by one skilled in the art using routine techniques to determine the appropriate predetermined cutoff for each biomarker depending on the desired result. After the amount of each biomarker is compared to the predetermined cutoff, a score (namely, a number, which can be any integer, such as from 0 to 100) is then assigned to each biomarker based on the comparison. Moreover, if in addition to the one or more biomarkers, the values of one or more biometric parameters are obtained for a subject, then the value of each biometric parameter is compared against a predetermined cutoff for said biometric parameter. The predetermined cutoff for any biometric parameter can be determined using the same techniques as described herein with respect to determining the predetermined cutoffs for one or more biomarkers. As with the biomarker comparison, a score (namely, a number, which can be any integer, such as 0 to 100) is then assigned to that biometric parameter based on said comparison.

Alternatively, instead of using the scoring method described above, a Weighted Scoring Method can be used. If a Weighted Scoring Method is used, then once the amount of each biomarker in a test sample is quantified, then the amount of each biomarker detected in the test sample is compared to a number of predetermined cutoffs for that specific biomarker. From all of the different predetermined cutoffs available, a single score (namely, a number, which can be any integer, such as from 0 to 100) is then assigned to that biomarker. This Weighted Scoring Method can also be utilized with one or more biometric parameters as well.

Figure 5:
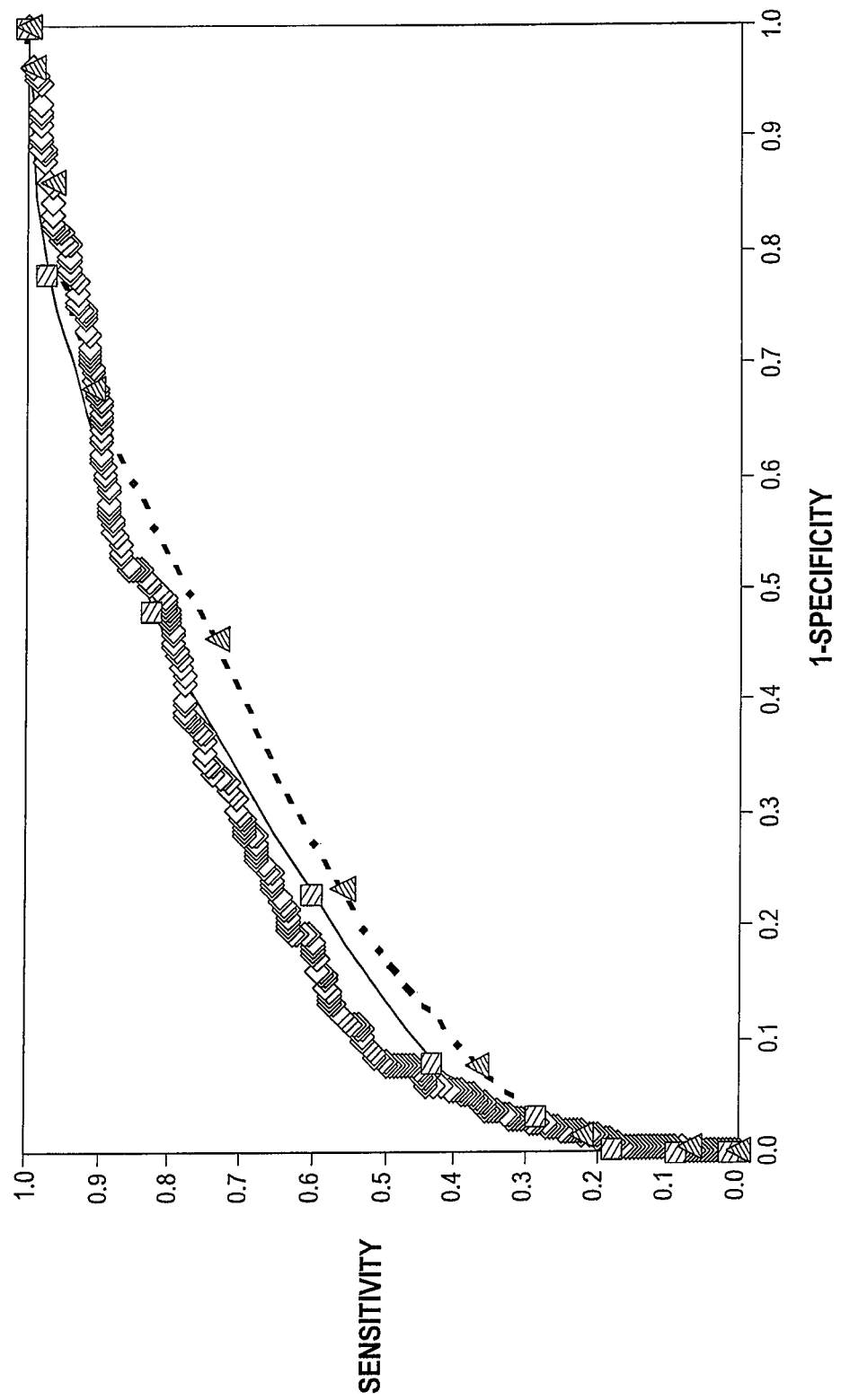
FIG. 5 gives ROC curves generated from an 8 immunoassay biomarker panel performed on 751 patient samples described in Example 1. The shaded diamonds represent the ROC curve generated from the total score using the Weighted Scoring Method. The squares represent the ROC curve generated from the total score using the binary scoring method using large cohort split points (cutoffs). The shaded triangles represent the ROC curve generated from the total score using the binary scoring method using the small cohort split points (cutoffs).

Once a score is assigned for each of the biomarkers quantified, and optionally, for any biometric parameters obtained from the subject, then the score for each biomarker or each biomarker and each biometric parameter is combined to obtain a total score for the subject. This total score is then compared with a predetermined total score. Based on this comparison, a determination can be made whether or not a subject is a risk of lung cancer. The determination of whether or not a subject is at risk of developing lung cancer may be based on whether or not the total score is higher or lower than the predetermined total score. For example, depending on the value assigned to the predetermined total score, a subject with a total score that is higher than the total predetermined score may be considered to be at higher risk and thus may be referred for further testing or follow-up procedures. The predetermined total score (alternatively referred to as a "threshold" herein) to be used in the method can be determined using the same techniques described above with respect to the predetermined scores for the biomarkers. For example, FIG. 5 provides three ROC curves. Each of these ROC curves represents the single output of combined markers, however, a single marker would produce a similar ROC curve. The ROC curves span from low sensitivity and low false positive rate (1-specificity) at one end to high sensitivity and high false positive rate at the other end. Curve shape in between these two ends can vary significantly. If a method were required to have at least 90% sensitivity, then based on the ROC curves shown in FIG. 5, the false positive rate would be 60-70% depending on the curve chosen. If the method were required to have at most a 10% false positive rate, then the sensitivity would be 40-55% depending on the curve chosen. Both of these methods are derived from the same panel of markers, however, in order to provide different clinical performance characteristics, the threshold (or predetermined total score) of the panel has been changed. By way of calculation, underlying each point on the ROC curve is a threshold (or predetermined total score) that moves from one end of the data range to the other end of the data range. When the threshold (or predetermined total score) is at the low end of the data range, then all samples are positive and this produces a point on the ROC curve with high sensitivity and high false positive rate. When the threshold (or predetermined total score) is at the high end of the data range, then all samples are negative and this produces a point on the ROC curve with low sensitivity and low false positive rate. Often a method is required to have a desired clinical characteristic, such as a minimum level of sensitivity (ie., 90%), a minimum level of specificity (ie., 90%), or both. Changing the threshold (or predetermined total score) of the markers can help achieve the desired clinical characteristics.

The above described steps of (a) comparing the amount of each biomarker in a panel to a predetermined cutoff (or a number of predetermined cutoffs if the Weighted Scoring Method is used), assigning a score (or a score from one of a number of possible scores if the Weighted Scoring Method is used) for each biomarker based on the comparison, combining the assigned score for each biometric parameter in a panel to obtain a total score for the subject, comparing the total score with a predetermined total score and determining whether a subject has a risk of lung cancer based on the comparison of the total score with the predetermined score; or (b) comparing the value of at least one biometric parameter against a predetermined cutoff (or a number of predetermined cutoffs if the Weighted Scoring Method is used) for each biometric parameter and assigning a score (or a score from one of a number of possible scores if the Weighted Scoring Method is used) for each biometric parameter based on said comparison, comparing the amount of each biomarker in a panel to a predetermined cutoff, assigning a score for each biomarker based on the comparison, combining the assigned score for each biometric parameter with the assigned score for each biomarker quantified to obtain a total score for the subject, comparing the total score with a predetermined total score and determine whether a subject has a risk of lung cancer based on the comparison of the total score with the predetermined score can be performed manually, such as by a human, or can completely or partially be performed by a computer program or algorithm, along with the necessary hardware, such as input, memory, processing, display and output devices.

For illustrative purposes only, an example of how the method of the present invention can be performed shall now be given. In this example, a patient is tested to determine the patient's likelihood of having lung cancer using a panel comprising 8 biomarkers and the Split and Score Method. The biomarkers in the panel are: cytokeratin 19, CEA, CA125, CA15-3, CA19-9, SCC, proGRP and cytokeratin 18. The predetermined total score (or threshold) for the panel is 3. After obtaining a test sample from the patient, the amount of each of the 8 biomarkers (cytokeratin 19, CEA, CA 125, CA15-3, CA19-9, SCC, proGRP and cytokeratin 18) in the patient's test sample is quantified. For the purposes of this example, the amount of each of the 8 biomarkers in the test sample is determined to be: cytokeratin 19: 1.95, CEA: 2.75, CA125: 15.26, CA15-3: 11.92, CA19-9: 9.24, SCC: 1.06, proGRP: 25.29 and cytokeratin 18: 61.13. The amount of each of these biomarkers is then compared to the corresponding predetermined cutoff (or split point). The predetermined cutoffs for each of the biomarkers is: cytokeratin 19: 1.89, CEA: 4.82, CA125: 13.65, CA15-3: 13.07, CA19-9: 10.81, SCC: 0.92, proGRP: 14.62 and cytokeratin 18: 57.37. For each biomarker having an amount that is higher than its corresponding predetermined cutoff (split point), a score of 1 may be given. For each biomarker having an amount that is less than or equal to its corresponding predetermined cutoff, a score of 0 may be given. Thereupon, based on said comparison, each biomarker would be assigned a score as follows: cytokeratin 19: 1, CEA: 0, CA125: 1, CA15-3: 0, CA19-9: 0, SCC: 1, proGRP: 1, and cytokeratin 18: 1. The score for each of the 8 biomarkers are then combined mathematically (i.e., by adding each of the scores of the biomarkers together) to arrive at the total score for the patient. The total score for the patient is 5 (The total score is calculated as follows: 1+0+1+0+0+1+1+1=5). The total score for the patient is compared to the predetermined total score, which is 3. A total score greater than the predetermined total score of 3 would indicate a positive result for the patient. A total score less than or equal to 3 would indicate a negative result for the patient. In this example, because the patient's total score is greater than 3, the patient would be considered to have a positive result and thus would be referred for further testing for an indication or suspicion of lung cancer. In contrast, had the patient's total score been 2, the patient would have been considered to have a negative result and would not be referred for any further testing.

In a further example, the 8 biomarker panel described above is again used, however, in this example, the Weighted Scoring Method is employed. In this example, the predetermined total score (or threshold) for the panel is 11.2 and the amounts of the biomarkers quantified in the test sample are the same as described above. The amount of each of the biomarkers is then compared to 3 different predetermined cutoffs for each of the biomarkers. For example, the predetermined cutoffs for each of the biomarkers are provided below in Table A.

TABLE A

|  | CEA | Cytokeratin 18 | ProGRP | CA15-3 | CA125 | SCC | Cytokeratin 19 | CA19-9 |
|---|---|---|---|---|---|---|---|---|
| Predetermined cutoff @ 50% specificity | 2.02 | 47.7 | 11.3 | 16.9 | 15.5 | 0.93 | 1.2 | 10.6 |
| Predetermined cutoff @ 75% specificity | 3.3 | 92.3 | 18.9 | 21.8 | 27 | 1.3 | 1.9 | 21.9 |
| Predetermined cutoff @ 90% specificity | 4.89 | 143.3 | 28.5 | 30.5 | 38.1 | 1.98 | 3.3 | 45.8 |
| score below 50% specificity | 0 | 0 | 0 | <u>0</u> | <u>0</u> | 0 | 0 | <u>0</u> |
| score above 50% specificity | <u>2.68</u> | <u>2.6</u> | 2.48 | 1.16 | 2.68 | <u>2.48</u> | 4.2 | 1.1 |
| score above 75% specificity | 5.36 | 5.2 | <u>4.96</u> | 2.32 | 5.36 | 4.96 | <u>8.4</u> | 2.2 |
| score above 90% specificity | 13.4 | 13 | 12.4 | 5.8 | 13.4 | 12.4 | 21 | 5.5 |

Therefore, 4 possible scores may be given for each biomarker. The amount of each biomarker quantified is compared to the predetermined cutoffs (split points) provided in Table A above. For example, for CEA, since the amount of CEA quantified in the test sample was 2.75, it falls between the predetermined cutoff of 2.02 for 50% specificity and 3.3 for 75% specificity in the Table A. Hence, CEA is assigned a score of 2.68. This is repeated for the remaining biomarkers which are similarly assessed and each assigned the following scores: cytokeratin 18: 2.6, proGRP: 4.96, CA15-3: 0, CA125: 0, SCC: 2.48, cytokeratin 19: 8.4 and CA19-9: 0. The score for each of the 8 biomarkers are then combined mathematically (i.e., by adding each of the scores of the biomarkers together) to arrive at the total score for the patient. The total score for the patient is 21.12 (The total score is calculated as follows: 2.68+2.6+4.96+0+0+2.48+8.4+0=21.12). The total score for the patient is compared to the predetermined total score, which is 11.2. A total score greater than the predetermined total score of 11.2 would indicate a positive result for the patient. A total score less than or equal to 11.2 would indicate a negative result for the patient. In this example, because the patient's total score was greater than 11.2, the patient would be considered to have a positive result and thus would be referred for further testing for an indication or suspicion of lung cancer.

Furthermore, in another embodiment, the Weighted Scoring Method described herein can also be used to score one or more markers obtained from a subject. Preferably, such markers, whether one or more biomarkers, one or more biometric parameters or a combination of biomarkers and biometric parameters can be used as an aid in diagnosing or assessing whether a subject is at risk for developing a medical condition, such a cancer or some other disease. The Weighted Scoring Method can be used broadly in connection with any medical condition in which markers are used or can be used to assess whether a subject is at risk for such a medical condition. Such a method can comprise the steps of:

a. quantifying in a test sample obtained from a subject, the amount of at least one marker;

b. comparing the amount of each marker quantified to a number of predetermined cutoffs for said marker and assigning a score for each marker based on said comparison; and c. combining the assigned score for each marker quantified in step b to obtain a total score for said subject.

Preferably, the method comprises the steps of:

a. quantifying in a test sample obtained from a subject, the amount of at least marker;

b. comparing the amount of each marker quantified to a number of predetermined cutoffs for said marker and assigning a score for each marker based on said comparison;

c. combining the assigned score for each marker quantified in step b to obtain a total score for said subject;

d. comparing the total score determined in step c with a predetermined total score; and e. determining whether said subject has a risk of developing a medical condition based on the comparison of the total score determined in step d.

DFI

As discussed previously herein, Applicants have found that the detection and quantification of one or more biomarkers or a combination of biomarkers and biometric parameters is useful as an aid in diagnosing lung cancer in a patient. In addition, Applicants have also found that the one or more biomarker and one or more biomarker and one or more biometric parameter combinations described herein have a DFI relative to lung cancer less than about 0.5, preferably less than about 0.4, more preferably, less than about 0.3 and even more preferably, less than about 0.2. Tables 25-29 provide examples of panels containing various biomarker or biomarker and biometric parameter combinations that exhibit a DFI that is less than about 0.5, less than about 0.4, less than about 0.3 and less than about 0.2.

Kits

One or more biomarkers, one or more of the immunoreactive Cyclin E2 polypeptides, biometric parameters and any combinations thereof are amenable to the formation of kits (such as panels) for use in performing the methods of the present invention. In one aspect, the kit can comprise a peptide selected from the group consisting of: SEQ ID NO:1, SEQ ID NO:3, SEQ ID NO:4, SEQ ID NO:5 or combinations thereof.

In another aspect, the kit can comprise anti-Cyclin E2 or any combinations thereof.

In a further aspect, the kit can comprise (a) reagents containing at least one antibody for quantifying one or more antigens in a test sample, wherein said antigens are: cytokeratin 8, cytokeratin 19, cytokeratin 18, CEA, CA125, CA15-3, SCC, CA19-9, proGRP, serum amyloid A, alpha-1-antitrypsin, apolipoprotein CIII and Tβ4; (b) reagents containing one or more antigens for quantifying at least one antibody in a test sample; wherein said antibodies are: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2; and optionally, (c) one or more algorithms or computer programs for performing the steps of combining and comparing the amount of each antigen and antibody quantified in the test sample against a predetermined cutoff (or against a number of predetermined cutoffs) and assigning a score for each antigen and antibody (or a score from one of a number of possible scores) quantified based on said comparison, combining the assigned score for each antigen and antibody quantified to obtain a total score, comparing the total score with a predetermined total score and using said comparison as an aid in determining whether a subject has lung cancer. Alternatively, in lieu of one or more algorithms or computer programs, one or more instructions for manually performing the above steps by a human can be provided.

In yet another aspect, the kit can contain: (a) reagents containing at least one antibody for quantifying one or more antigens in a test sample, wherein said antigens are: cytokeratin 8, cytokeratin 19, cytokeratin 18, CEA, CA125, CA15-3, SCC, CA19-9, proGRP, serum amyloid A, alpha-1-antitrypsin, apolipoprotein CIII and Tβ4; (b) reagents containing one or more antigens for quantifying at least one antibody in a test sample; wherein said antibodies are: anti-p53, anti-TMP21, anti-NY-ESO-1, anti-HDJ1, anti-NPC1L1C-domain, anti-TMOD1, anti-CAMK1, anti-RGS1, anti-PACSIN1, anti-RCV1, anti-MAPKAPK3 and anti-Cyclin E2; (c) reagents for quantifying one or more regions of interest selected from the group consisting of: ACN9459, Pub11597, Pub4789, TFA2759, TFA9133, Pub3743, Pub8606, Pub4487, Pub4861, Pub6798, Tfa6453 and Hic3959; and optionally, (d) one or more algorithms or computer programs for performing the steps of combining and comparing the amount of each antigen, antibody and region of interest quantified in the test sample against a predetermined cutoff (or against a number of predetermined cutoffs) and assigning a score for each antigen, antibody and region of interest (or a score from one of a number of possible scores) quantified based on said comparison, combining the assigned score for each antigen, antibody and region of interest quantified to obtain a total score, comparing the total score with a predetermined total score and using said comparison as an aid in determining whether a subject has lung cancer. Alternatively, in lieu of one or more algorithms or computer programs, one or more instructions for manually performing the above steps by a human can be provided. The reagents included in the kit for quantifying one or more regions of interest may include an adsorbent which binds and retains at least one region of interest contained in a panel, solid supports (such as beads) to be used in connection with said absorbents, one or more detectable labels, etc. The adsorbent can be any of many adsorbents used in analytical chemistry and immunochemistry, including metal chelates, cationic groups, anionic groups, hydrophobic groups, antigens and antibodies. In yet still another aspect, the kit can comprise: (a) reagents containing at least one antibody for quantifying one or more antigens in a test sample, wherein said antigens are cytokeratin 19, cytokeratin 18, CA 19-9, CEA, CA15-3, CA125, SCC and Pro-GRP; (b) reagents for quantifying one or more regions of interest selected from the group consisting of: ACN9459, Pub11597, Pub4789, TFA2759, TFA9133, Pub3743, Pub8606, Pub4487, Pub4861, Pub6798, Tfa6453 and Hic3959; and optionally, (c) one or more algorithms or computer programs for performing the steps of combining and comparing the amount of each antigen and region of interest quantified in the test sample against a predetermined cutoff (or against a number of predetermined cutoffs) and assigning a score for each antigen and region of interest (or a score from one of a number of possible scores) quantified based on said comparison, combining the assigned score for each antigen and region of interest quantified to obtain a total score, comparing the total score with a predetermined total score and using said comparison as an aid in determining whether a subject has lung cancer. Alternatively, in lieu of one or more algorithms or computer programs, one or more instructions for manually performing the above steps by a human can be provided. The reagents included in the kit for quantifying one or more regions of interest may include an adsorbent which binds and retains at least one region of interest contained in a panel, solid supports (such as beads) to be used in connection with said absorbents, one or more detectable labels, etc. Preferably, the kit contains the necessary reagents to quantify the following antigens and regions of interest: (a) cytokeratin 19 and CEA and Acn9459, Pub11597, Pub4789 and Tfa2759; (b) cytokeratin 19 and CEA and Acn9459, Pub11597, Pub4789, Tfa2759 and Tfa9133; and (c) cytokeratin 19, CEA, CA125, SCC, cytokeratin 18, and ProGRP and ACN9459, Pub11597, Pub4789 and Tfa2759.

In another aspect, a kit can comprise (a) reagents containing at least one antibody for quantifying one or more antigens in a test sample, wherein said antigens are cytokeratin 19, cytokeratin 18, CA 19-9, CEA, CA15-3, CA125, SCC and ProGRP; and optionally, (b) one or more algorithms or computer programs for performing the steps of combining and comparing the amount of each antigen quantified in the test sample against a predetermined cutoff (or against a number of predetermined cutoffs) and assigning a score for each antigen (or a score from one of a number of possible scores) quantified based on said comparison, combining the assigned score for each antigen quantified to obtain a total score, comparing the total score with a predetermined total score and using said comparison as an aid in determining whether a subject has lung cancer. Alternatively, in lieu of one or more algorithms or computer programs, one or more instructions for manually performing the above steps by a human can be provided. The kit can also contain one or more detectable labels. Preferably, the kit contains the necessary reagents to quantify the following antigens cytokeratin 19, cytokeratin 18, CA 19-9, CEA, CA-15-3, CA125, SCC and ProGRP.

In another aspect, a kit can comprise (a) reagents for quantifying one or more biomarkers, wherein said biomarkers are regions of interest selected from the group consisting of: ACN9459, Pub11597, Pub4789, TFA2759, TFA9133, Pub3743, Pub8606, Pub4487, Pub4861, Pub6798, Tfa6453 and Hic3959; and optionally, (b) one or more algorithms or computer programs for performing the steps of combining and comparing the amount of each biomarker quantified in the test sample against a predetermined cutoff (or against a number of predetermined cutoffs) and assigning a score for each biomarker (or a score from one of a number of possible scores) quantified based on said comparison, combining the assigned score for each biomarker quantified to obtain a total score, comparing the total score with a predetermined total score and using said comparison as an aid in determining whether a subject has lung cancer. Alternatively, in lieu of one or more algorithms or computer programs, one or more instructions for manually performing the above steps by a human can be provided. Preferably, the regions of interest to be quantified in the kit are selected from the group consisting of: Pub11597, Pub3743, Pub8606, Pub4487, Pub4861, Pub6798, Tfa6453 and Hic3959. The reagents included in the kit for quantifying one or more regions of interest may include an adsorbent which binds and retains at least one region of interest contained in a panel, solid supports (such as beads) to be used in connection with said absorbents, one or more detectable labels, etc.

In yet another aspect, a kit can comprise: (a) reagents containing one or more antibodies for quantifying one or more antigens in a test sample, wherein said antigens are: cytokeratin 19, CEA, CA 125 and proGRP; (b) reagents containing one or more antigens for quantifying at least one antibody in a test sample; wherein said antibodies are: anti-p53, anti-NY-ESO-1, anti-MAPKAPK3 and anti-Cyclin E2; and optionally, (c) one or more algorithms or computer programs for performing the steps of combining and comparing the amount of each antigen, antibody and region of interest quantified in the test sample against a predetermined cutoff (or against a number of predetermined cutoffs) and assigning a score for each antigen, antibody and region of interest (or a score from one of a number of possible scores) quantified based on said comparison, combining the assigned score for each antigen, antibody and region of interest quantified to obtain a total score, comparing the total score with a predetermined total score and using said comparison as an aid in determining whether a subject has lung cancer. Alternatively, in lieu of one or more algorithms or computer programs, one or more instructions for manually performing the above steps by a human can be provided. The kit can contain an antibody for quantifying each of cytokeratin 19, CEA, CA 125 and proGRP, an antigen for quantifying each of anti-p53, anti-NY-ESO-1, anti-MAPKAPK3 and anti-Cyclin E2 or an antibody for quantifying each of cytokeratin 19, CEA, CA 125 and proGRP and an antigen for quantifying each of anti-p53, anti-NY-ESO-1, anti-MAPKAPK3 and anti-Cyclin E2.

Identification of Biomarkers

The biomarkers of the invention can be isolated, purified and identified by techniques well known to those skilled in the art. These include chromatographic, electrophoretic and centrifugation techniques. These techniques are discussed in Current Protocols in Protein Science, J. Wiley and Sons, New York, N.Y., Coligan et al. (Eds) (2002) and Harris, E. L. V., S. Angal in *Protein Purification Applications: A Practical Approach*, Oxford University Press, New York, N.Y. (1990) and elsewhere.

By way of example, and not of limitation, examples of the present invention shall now be provided.

EXAMPLES

Clinical samples of patient blood sera were collected (Example 1) and were analyzed for immunoassay antigen markers (Example 2), for immunoassay antibody markers using beads (Example 3) or slides (Example 4), and for biomarkers identified by mass spectrometry (Example 5). The identified markers were sorted and prioritized using a variety of algorithms (Example 6). These prioritized markers were combined using a scoring method (Example 7) to identify predictive models (Example 8) to assess clinical utility. Examples of the use of the methods aiding in detecting lung cancer in patients suspected of having lung cancer are illustrated in Example 9. The biomarkers identified by Regions of Interest of mass spectrometry were analyzed to determine their composition and identity (Example 10). Example 11 is a prophetic example that describes how the biomarkers identified according to the present invention can be detected and measured using immunoassay techniques and immuno mass spectrometric techniques.

Example 1

Clinical Specimens

Clinical samples of patient serum were collected under an Institutional Review Board approved protocol. All subjects who contributed a specimen gave informed consent for the specimen to be collected and used in this project. Serum samples were drawn into a serum separator tube and allowed to clot for 15 minutes at room temperature. The clot was spun down and the sample poured off into 2 mL aliquots. Within 24 hours the samples were frozen at −80° C. and maintained at that temperature until further processing was undertaken. Upon receipt, the samples were thawed and realiquoted into smaller volumes for convenience and refrozen. The samples were then thawed a final time immediately before analysis. Therefore, every sample in the set was frozen and thawed twice before analysis.

A total of 751 specimens were collected and analyzed. The group was composed of 250 biopsy confirmed lung cancer patients, 274 biopsy confirmed benign lung disease patients, and 227 apparently normal subjects. The cancer and benign patients were all confirmed in their diagnosis by a definitive biopsy. The normal subjects underwent no such definitive diagnostic procedure and were judged "normal" by the lack of overt malignant disease. After this definitive diagnostic procedure, only patients aged ≥50 yrs were then selected. After this selection, there remained 231 cancers, 182 benigns, and 155 normals. This large cohort of cancer, benign lung disease, and apparently normal subjects will be collectively referred to hereinafter as the "large cohort". A subset of the large cohort was used to focus in on the differentiation between benign lung disease and lung cancer. This cohort, hereinafter referred to as the "small cohort", consisted of 138 cancers, 106 benigns, and 13 apparently normal subjects. After removing the "small cohort" from the "large cohort", there remained 107 cancers, 74 benigns, and 142 apparently normal subjects. This cohort, hereinafter referred to as the "validation cohort" is independent of the small cohort and was used to validate the predictive models generated. The clinical samples prepared as described were used in Examples 2-10.

Example 2

Immunoassay Detection of Biomarkers

A. Abbott Laboratories (Abbott Park, Ill., hereinafter "Abbott") Architect™ Assays Architect™ kits were acquired for the following antigens: CEA, CA125, SCC, CA19-9 and CA15-3. All assays were run according to the manufacturer's instructions. The concentrations of the analytes in the samples were provided by the Architect™ instrument. These concentrations were used to generate the AUC data shown below in Table 1.

TABLE 1

Clinical performance (AUC) of CA125, CEA, CA15-3, CA19-9, and SCC in the small and large cohorts. The #obs refers to the total number of individuals or clinical samples in each group.

| Marker | large cohort | | small cohort | |
|---|---|---|---|---|
| | #obs | AUC | #obs | AUC |
| Ca19-9 | 548 | 0.548 | 256 | 0.559 |
| CEA | 549 | 0.688 | 257 | 0.664 |
| Ca15-3 | 549 | 0.604 | 257 | 0.569 |
| Ca125 | 549 | 0.693 | 257 | 0.665 |
| SCC | 549 | 0.615 | 257 | 0.639 |

B. Roche Elecsys™ Assay

Cyfra 21-1 (Cytokeratin 19, CK-19) measurements were made on the Elecsys™ 2010 system (Roche Diagnostics GmbH, Mannheim, Germany) according to the manufacturer's instructions. The concentration of Cyfra 21-1 was provided by the Elecsys™ instrument. A ROC curve was generated with the data and the AUC for the large and small cohorts are reported below in Table 2.

TABLE 2

Clinical performance (AUC) of Cytokeratin 19.

| Marker | large cohort | | small cohort | |
|---|---|---|---|---|
| | #obs | AUC | #obs | AUC |
| CK-19 | 537 | 0.68 | 248 | 0.718 |

C. Microtiter Plate Assays

The following ELISA kits were purchased: ProGRP from Advanced Life Science Institute, Inc. (Japan), TPS (Cytokeratin 18, CK-18) from IDL Biotech AB (Bromma, Sweden) and Parainfluenza 1/2/3 IgG ELISA from IBL Immuno Biological Laboratories (Minneapolis, Minn., USA). The assays were run according to the manufacturer's instructions. The concentrations of the analytes were derived from calculations instructed and provided for in the manufacturer's protocol. The AUC obtained for the individual assays are shown below in Table 3.

TABLE 3

Clinical performance (AUC) of Cytokeratin 18, proGRP, and parainfluenza 1/2/3.

| Marker | large cohort | | small cohort | |
|---|---|---|---|---|
| | #obs | AUC | #obs | AUC |
| CK-18 | 548 | 0.656 | 257 | 0.657 |
| ProGRP | 548 | 0.698 | 257 | 0.533 |
| Parainfluenza 1/2/3 | 544 | 0.575 | 255 | 0.406 |

Example 3

Autoantibody Bead Array

A. Commercially available human proteins (See, Table 4, below) were attached to Luminex™ SeroMap™ beads (Austin, Tex.) and the individual beadsets were combined to prepare the reagent. Portions of the reagent were exposed to the human serum samples under conditions that allow any antibodies present to bind to the proteins. The unbound material was washed off and the beads were then exposed to a fluorescent conjugate of R-phycoerythrin linked to an antibody that specifically binds to human IgG. After washing, the beads were passed through a Luminex™ 100 instrument, which identified each bead according to its internal dyes, and measured the fluorescence bound to the bead, corresponding to the quantity of antibody bound to the bead. In this way, the immune responses of 772 samples (251 lung cancer, 244 normal, 277 benign) against 21 human proteins, as well as several non-human proteins for controls (bovine serum albumin (BSA) and tetanus toxin), were assessed.

The antigens MUC-1 (Fujirebio Diagnostics INC, Malvern, Pa.), Cytokeratin 19 (Biodesign, Saco, Me.), and CA-125 (Biodesign, Saco, Me.) were obtained as ion-exchange fractions of cell cultures (See Table 4, below). These relatively crude preparations were subjected to further fractionation by molecular weight using HPLC with a size exclusion column (BioRad SEC-250, Hercules, Calif.) with mobile phase=PBS at 0.4 mL/minute. Fractions were collected starting at 15 minutes with 1 minute for each fraction for a total of 23 fractions for each antigen. For MUC-1, 250 uL was injected; for Cytokeratin 19 and CA-125, 150 uL was injected. All three samples showed signals indicating various concentrations of higher MW proteins eluting from 15-24 minutes, with signals too high to measure at times longer than 24 minutes, indicating high concentrations of lower MW materials. For coating on beads the following fractions were combined: MUC-1-A fractions 6,7; MUC-1-B fractions 10,11; MUC-1-C fractions 12,13; Cytokeratin 19-A fractions 4,5; Cytokeratin 19-B fractions 8,9; Cytokeratin 19-C fractions 16,17; CA125-A fractions 5,6; CA125-B fractions 12,13.

TABLE 4

List of proteins.

| Bead ID | Antigen | Source |
|---|---|---|
| 1 | MUC-1-A | Fujirebio Diagnostics INC |
| 2 | MUC-1-B | Fujirebio Diagnostics INC |
| 3 | MUC-1-C | Fujirebio Diagnostics INC |
| 4 | Cytokeratin 19-A | Biodesign, Saco, ME |
| 5 | Cytokeratin 19-B | Biodesign, Saco, ME |
| 6 | Cytokeratin 19-C | Biodesign, Saco, ME |
| 7 | CA125-A | Biodesign, Saco, ME |
| 8 | CA125-B | Biodesign, Saco, ME |
| 9 | HSP27 | US Biological, Swampscott, MA |
| 10 | HSP70 | Alexis, San Diego, CA |
| 11 | HSP90 | Alexis, San Diego, CA |
| 12 | Tetanus | Sigma, St. Louis, MO |
| 13 | HCG | Diosynth API, Des Plaines, IL |
| 14 | VEGF | Biodesign, Saco, ME |
| 15 | CEA | Biodesign, Saco, ME |
| 16 | NY-ESO-1 | NeoMarkers, Fremont, CA |
| 17 | AFP | Cell Sciences, Canton, MA |
| 18 | ERB-B2 | Invitrogen, Grand Island, NY |
| 19 | PSA | Fitzgerald, Concord, MA |
| 20 | P53 | Lab Vision, Fremont, CA |
| 21 | JO-1 | Biodesign, Saco, ME |
| 22 | Lactoferrin | Sigma, St. Louis, MO |
| 23 | HDJ1 | Alexis, San Diego, CA |
| 24 | Keratin | Sigma, St. Louis, MO |
| 25 | RECAF62 | BioCurex, Vancouver, BC Canada |
| 26 | RECAF50 | BioCurex, Vancouver, BC Canada |
| 27 | RECAF milk | BioCurex, Vancouver, BC Canada |
| 28 | BSA | Sigma, St. Louis, MO |

B. Coating of Luminex SeroMap™ Beads with Antigens

To wells of an Omega10K ultrafiltration plate (Pall Corporation, Ann Arbor, Mich.) was added 50 uL of water. After 10 minutes the plate was placed on a vacuum. When wells were empty, 10 uL water was added to retain hydration. To each well was added 50-100 uL of 5 mM morpholinoethanesulfonic acid (MES) pH 5.6, 50 uL of the indicated Luminex™ SeroMAP™ bead and the appropriate volume corresponding to 10-20 ug of each antigen indicated in Table 4. The beads were suspended with the pipet. To the beads was added 10 uL EDAC (2.0 mg in 1.0 mL 5 mM MES pH 5.6). The plate was covered and placed on a shaker in the dark. After 14 hours, the plate was suctioned by vacuum, washed with water, and finally the beads were resuspended in 50 uL 20 mM triethanolamine (TEA) pH 5.6. The plate was agitated by shaker in the dark. A second 10 uL EDAC (2.0 mg in 1.0 mL 5 mM MES pH 5.6) was added to each well, and the plate was placed on a shaker in the dark for one hour. After washing, 200 uL PBS buffer containing 1% BSA and 0.08% sodium azide (PBN) was added to each well, followed by sonication with probe, and placed in dark.

C. Testing of Serum Samples with Coated Beads

Serum samples were prepared in microplates at a 1:20 dilution in PBN, with 80 samples per microplate. To 50 uL of the beadset described above was added 5 uL of rabbit serum (from a rabbit immunized with an antigen unrelated to those tested here). The beadset was vortexed and placed at 37° C. After 35 minutes, 1 mL of PBN containing 5% rabbit serum and 1% CHAPS (BRC) was added. The beadset was vortexed, spun down, and resuspended in 1.05 mL BRC. The wells of a Supor 1.2u filter plate (Pall Corporation) were washed with 100 uL PBN. To each well was added 50 uL BRC, 10 uL each 1:20 serum sample, and 10 uL of resuspended beads. The plate was shaken at room temp in the dark for 1 hour, filtered and then washed 3 times for 10 minutes with 100 uL BRC. Detection conjugate 50 uL of (20 uL RPE antihuman IgG in 5.0 mL BRC) was added and the plate was shaken in the dark for 30 minutes after beads were resuspended by pipet. 100 uL of BRC was then added, beads were agitated by pipet and the samples analyzed on a Luminex™ 100 instrument.

The results (median intensity of beads for each sample and antigen) were evaluated by ROC analysis with the following results for the large and small cohorts shown below in Table 5:

TABLE 5

Clinical performance of the autoantibody bead array containing proteins from Table 4 in the large and small cohorts.

| | large cohort | | small cohort | |
|---|---|---|---|---|
| Biomarker | # obs | AUC | # obs | AUC |
| MUC-1-A | 579 | 0.53 | 253 | 0.56 |
| MUC-1-B | 579 | 0.55 | 253 | 0.59 |
| MUC-1-C | 579 | 0.57 | 253 | 0.61 |
| Cytokeratin 19-A | 579 | 0.57 | 253 | 0.58 |
| Cytokeratin 19-B | 579 | 0.53 | 253 | 0.49 |
| Cytokeratin 19-C | 579 | 0.62 | 253 | 0.65 |
| CA125-A | 579 | 0.53 | 253 | 0.5 |
| CA125-B | 579 | 0.62 | 253 | 0.59 |
| HSP27 | 579 | 0.56 | 253 | 0.56 |
| HSP70 | 579 | 0.49 | 253 | 0.51 |
| HSP90 | 579 | 0.54 | 253 | 0.53 |
| Tetanus | 579 | 0.57 | 253 | 0.56 |
| HCG | 579 | 0.54 | 253 | 0.5 |
| VEGF | 579 | 0.53 | 253 | 0.51 |
| CEA | 579 | 0.57 | 253 | 0.55 |
| NY-ESO-1 | 579 | 0.58 | 253 | 0.58 |
| AFP | 579 | 0.51 | 253 | 0.55 |
| ERB-B2 | 579 | 0.61 | 253 | 0.57 |

TABLE 5-continued

Clinical performance of the autoantibody bead array containing proteins from Table 4 in the large and small cohorts.

| Biomarker | large cohort | | small cohort | |
|---|---|---|---|---|
| | # obs | AUC | # obs | AUC |
| PSA | 579 | 0.6 | 253 | 0.57 |
| P53 | 579 | 0.6 | 253 | 0.54 |
| JO-1 | 579 | 0.57 | 253 | 0.54 |
| Lactoferrin | 579 | 0.49 | 253 | 0.49 |
| HDJ1 | 579 | 0.62 | 253 | 0.63 |
| Keratin | 579 | 0.58 | 253 | 0.55 |
| RECAF62 | 579 | 0.54 | 253 | 0.53 |
| RECAF50 | 579 | 0.53 | 253 | 0.53 |
| RECAF milk | 579 | 0.54 | 253 | 0.62 |
| BSA | 579 | 0.57 | 253 | 0.59 |

Example 4

Autoantibody Slide Array

A. Antigen Preparation

Approximately 5000 proteins derived from Invitrogen's Ultimate ORF Collection™ (Invitrogen, Grand Island, N.Y.) were prepared as recombinant fusions of the glutathione-S-transferase (GST) sequence with a full-length human protein. The GST tag allowed assessment of the quantity of each protein bound to the array independent of other characteristics of the protein.

B. Antigen Coating of Slides

The ProtoArray consists of a glass surface (slide) coated with nitrocellulose spotted with the approximately 5000 proteins mentioned above, as well as numerous control features.

C. Testing of Serum Samples with Coated Slides

The array was first blocked with PBS/1% BSA/0.1% Tween 20 for 1 hour at 4° C. It was then exposed to the serum sample diluted 1:120 in Profiling Buffer (the "Profiling Buffer" discussed herein contained PBS, 5 mM $MgCl_2$, 0.5 mM dithiothreitol, 0.05% Triton X-100, 5% glycerol, 1% BSA) for 90 minutes at 4° C. The array was then washed three times with Profiling Buffer for 8 minutes per wash. The array was then exposed to AlexaFluor-conjugated anti-human IgG at 0.5 ug/mL in Profiling Buffer for 90 minutes at 44° C. The array was then washed three times with Profiling Buffer for 8 minutes per wash. After drying on a centrifuge it was scanned using an Axon GenePix 4000B fluorescent microarray scanner (Molecular Devices, Sunnyvale, Calif.).

D. Biomarker Selection

By comparing the distribution of positive signals of serum from cancer patients with that from normal patients the identities of those proteins eliciting autoantibodies characteristic of cancer patients was determined. To increase the probability of finding cancer-specific autoantibodies with a limited number of arrays, the following pools of samples were used: 10 pools each containing serum from 4 or 5 lung cancer patients, 10 pools each containing serum from 4 or 5 normal patients and 10 pools each containing serum from 4 or 5 patients with benign lung diseases. These pools were sent to Invitrogen for processing as described above. The fluorescence intensities corresponding to each protein for each pool were presented in a spreadsheet. Each protein was represented twice, corresponding to duplicate spots on the array.

In one algorithm for assessment of cancer specificity of immune response for a particular protein, a cutoff value was supplied by the manufacturer (Invitrogen) which best distinguished the signal intensities of the cancer samples from those of the non-cancer samples. The number of samples from each group with intensities above this cutoff (Cancer Count and non-Cancer Count respectively) were determined and placed in the spreadsheet as parameters. Additionally, a p-value was calculated, representing the probability that there was no signal increase in one group compared to the other. The data were then sorted to bring to the top those proteins with the fewest positives in the non-cancer group and most positives in the cancer group, and further sorted by p-value from low to high. Sorting by this formula provided the following information provided below in Table 7.

TABLE 7

Antigen ID list.

| Antigen Identification | Cancer Count | non-cancer Count | P-Value |
|---|---|---|---|
| acrosomal vesicle protein 1 (ACRV1) | 6 | 0 | 0.0021 |
| forkhead box A3 (FOXA3) | 6 | 0 | 0.0072 |
| general transcription factor IIA | 6 | 0 | 0.5539 |
| WW domain containing E3 ubiquitin protein ligase 2 | 5 | 0 | 0.0018 |
| PDZ domain containing 1 (PDZK1) | 5 | 0 | 0.0018 |
| cyclin E2 | 5 | 0 | 0.0018 |
| cyclin E2 | 5 | 0 | 0.0018 |
| Phosphatidic acid phosphatase type 2 domain containing 3 (PPAPDC3) | 5 | 0 | 0.0088 |
| ankyrin repeat and sterile alpha motif domain containing 3 | 5 | 0 | 0.0563 |
| zinc finger | 5 | 0 | 0.0563 |
| cysteinyl-tRNA synthetase | 4 | 0 | 0.0077 |
| cysteinyl-tRNA synthetase | 4 | 0 | 0.0077 |
| transcription factor binding to IGHM enhancer 3 (TFE3) | 4 | 0 | 0.0077 |
| WW domain containing E3 ubiquitin protein ligase 2 | 4 | 0 | 0.0077 |
| Chromosome 21 open reading frame 7 | 4 | 0 | 0.0077 |
| Chromosome 21 open reading frame 7 | 4 | 0 | 0.0077 |
| IQ motif containing F1 (IQCF1) | 4 | 0 | 0.0077 |
| lymphocyte cytosolic protein 1 (L-plastin) (LCP1) | 4 | 0 | 0.0077 |
| acrosomal vesicle protein 1 (ACRV1) | 4 | 0 | 0.0077 |
| DnaJ (Hsp40) homolog | 4 | 0 | 0.0077 |
| DnaJ (Hsp40) homolog | 4 | 0 | 0.0077 |
| nuclear receptor binding factor 2 | 4 | 0 | 0.0077 |
| nuclear receptor binding factor 2 | 4 | 0 | 0.0077 |
| PDZ domain containing 1 (PDZK1) | 4 | 0 | 0.0077 |

TABLE 7-continued

Antigen ID list.

| Antigen Identification | Cancer Count | non-cancer Count | P-Value |
|---|---|---|---|
| protein kinase C and casein kinase substrate in neurons 2 | 4 | 0 | 0.0077 |
| LIM domain kinase 2 | 4 | 0 | 0.0077 |
| polymerase (RNA) III (DNA directed) polypeptide D | 4 | 0 | 0.0077 |
| RNA binding motif protein | 4 | 0 | 0.0077 |
| cell division cycle associated 4 (CDCA4) | 4 | 0 | 0.0312 |
| Rho guanine nucleotide exchange factor (GEF) 1 | 4 | 0 | 0.076 |
| LUC7-like 2 (S. cerevisiae) | 4 | 0 | 0.2302 |
| similar to RIKEN cDNA 2310008M10 (LOC202459) | 4 | 0 | 0.2302 |
| ribulose-5-phosphate-3-epimerase | 3 | 0 | 0.0296 |
| ribulose-5-phosphate-3-epimerase | 3 | 0 | 0.0296 |
| heme binding protein 1 (HEBP1) | 3 | 0 | 0.0296 |
| heme binding protein 1 (HEBP1) | 3 | 0 | 0.0296 |
| killer cell lectin-like receptor subfamily C | 3 | 0 | 0.0296 |
| killer cell lectin-like receptor subfamily C | 3 | 0 | 0.0296 |
| LATS | 3 | 0 | 0.0296 |
| N-acylsphingosine amidohydrolase (acid ceramidase) 1 (ASAH1) | 3 | 0 | 0.0296 |
| N-acylsphingosine amidohydrolase (acid ceramidase) 1 (ASAH1) | 3 | 0 | 0.0296 |
| Paralemmin | 3 | 0 | 0.0296 |
| Paralemmin | 3 | 0 | 0.0296 |
| PIN2-interacting protein 1 | 3 | 0 | 0.0296 |
| ribosomal protein S6 kinase | 3 | 0 | 0.0296 |
| ribosomal protein S6 kinase | 3 | 0 | 0.0296 |
| SH3 and PX domain containing 3 (SH3PX3) | 3 | 0 | 0.0296 |
| SH3 and PX domain containing 3 (SH3PX3) | 3 | 0 | 0.0296 |
| TCF3 (E2A) fusion partner (in childhood Leukemia) (TFPT) | 3 | 0 | 0.0296 |
| TCF3 (E2A) fusion partner (in childhood Leukemia) (TFPT) | 3 | 0 | 0.0296 |
| transcription factor binding to IGHM enhancer 3 (TFE3) | 3 | 0 | 0.0296 |
| Chromosome 1 open reading frame 117 | 3 | 0 | 0.0296 |
| Chromosome 1 open reading frame 117 | 3 | 0 | 0.0296 |
| cisplatin resistance-associated overexpressed protein | 3 | 0 | 0.0296 |
| hsp70-interacting protein | 3 | 0 | 0.0296 |
| hypothetical protein FLJ22795 | 3 | 0 | 0.0296 |
| hypothetical protein FLJ22795 | 3 | 0 | 0.0296 |
| interferon induced transmembrane protein 1 (9-27) | 3 | 0 | 0.0296 |
| interferon induced transmembrane protein 1 (9-27) | 3 | 0 | 0.0296 |
| IQ motif containing F1 (IQCF1) | 3 | 0 | 0.0296 |
| leucine-rich repeats and IQ motif containing 2 (LRRIQ2) | 3 | 0 | 0.0296 |
| leucine-rich repeats and IQ motif containing 2 (LRRIQ2) | 3 | 0 | 0.0296 |
| paralemmin 2 | 3 | 0 | 0.0296 |
| paralemmin 2 | 3 | 0 | 0.0296 |
| RWD domain containing 1 | 3 | 0 | 0.0296 |
| solute carrier family 7 | 3 | 0 | 0.0296 |
| solute carrier family 7 | 3 | 0 | 0.0296 |
| tropomyosin 1 (alpha) | 3 | 0 | 0.0296 |
| tropomyosin 1 (alpha) | 3 | 0 | 0.0296 |
| tumor suppressing subtransferable candidate 4 | 3 | 0 | 0.0296 |
| ubiquitin-like 4A | 3 | 0 | 0.0296 |
| vestigial like 4 (*Drosophila*) (VGLL4) | 3 | 0 | 0.0296 |
| WD repeat domain 16 | 3 | 0 | 0.0296 |
| WD repeat domain 16 | 3 | 0 | 0.0296 |
| mitogen-activated protein kinase-activated protein kinase 3 | 3 | 0 | 0.0296 |
| mitogen-activated protein kinase-activated protein kinase 3 | 3 | 0 | 0.0296 |
| death-associated protein kinase 1 (DAPK1) | 3 | 0 | 0.0296 |
| dimethylarginine dimethylaminohydrolase 2 (DDAH2) | 3 | 0 | 0.0296 |
| dimethylarginine dimethylaminohydrolase 2 (DDAH2) | 3 | 0 | 0.0296 |
| heat shock 70 kDa protein 2 | 3 | 0 | 0.0296 |
| melanoma antigen family H | 3 | 0 | 0.0296 |
| mitogen-activated protein kinase-activated protein kinase 3 (MAPKAPK3) | 3 | 0 | 0.0296 |
| nei like 2 (*E. coli*) (NEIL2) | 3 | 0 | 0.0296 |
| protein kinase C and casein kinase substrate in neurons 2 | 3 | 0 | 0.0296 |
| SMAD | 3 | 0 | 0.0296 |
| SMAD | 3 | 0 | 0.0296 |
| TIA1 cytotoxic granule-associated RNA binding protein | 3 | 0 | 0.0296 |
| trefoil factor 2 (spasmolytic protein 1) (TFF2) | 3 | 0 | 0.0296 |
| uroporphyrinogen III synthase (congenital erythropoietic porphyria) (UROS) | 3 | 0 | 0.0296 |
| cytokine induced protein 29 kDa (CIP29) | 3 | 0 | 0.0296 |
| transmembrane protein 106C (TMEM106C) | 3 | 0 | 0.0296 |
| Chromosome 9 open reading frame 11 | 3 | 0 | 0.0296 |
| O-6-methylguanine-DNA methyltransferase (MGMT) | 3 | 0 | 0.0296 |
| PDGFA associated protein 1 (PDAP1) | 3 | 0 | 0.0296 |
| PDGFA associated protein 1 (PDAP1) | 3 | 0 | 0.0296 |
| polymerase (RNA) III (DNA directed) polypeptide D | 3 | 0 | 0.0296 |

TABLE 7-continued

Antigen ID list.

| Antigen Identification | Cancer Count | non-cancer Count | P-Value |
|---|---|---|---|
| Rho-associated | 3 | 0 | 0.0296 |
| Rho-associated | 3 | 0 | 0.0296 |
| RNA binding motif protein | 3 | 0 | 0.0296 |
| tetraspanin 17 | 3 | 0 | 0.0296 |

A second algorithm calculated the cancer specificity of the immune response for a protein as the difference between the mean signal for cancer and the mean signal for non-cancer samples divided by the standard deviation of signal intensities of the non-cancer samples. This has the advantage that strong immune responses affect the result more than weak ones. The data are then sorted to bring to the top those proteins with the highest values. The top 100 listings identified by this sort is shown below in Table 8:

TABLE 8

Antigen ID list sorted to bring on top those proteins with the highest S/N ratio. The S/N was calculated by dividing the difference of the mean signal intensity of the two groups (Cancer mean – nonCancer mean) by the standard deviation of the non-cancer group (SD non-cancer).

| Antigen Identification | Mean Diff/SD (non-cancer) |
|---|---|
| TCF3 (E2A) fusion partner (in childhood Leukemia) (TFPT) | 21.4 |
| ubiquitin specific protease 45 (USP45) | 16.1 |
| ubiquitin specific protease 45 (USP45) | 15.6 |
| ubiquitin-conjugating enzyme E2O | 15.1 |
| TCF3 (E2A) fusion partner (in childhood Leukemia) (TFPT) | 13.9 |
| ubiquitin-conjugating enzyme E2O | 12.3 |
| proline-rich coiled-coil 1 (PRRC1) | 11.5 |
| proline-rich coiled-coil 1 (PRRC1) | 10 |
| B-cell CLL/lymphoma 10 | 9.8 |
| solute carrier family 7 | 8.8 |
| B-cell CLL/lymphoma 10 | 8.7 |
| DnaJ (Hsp40) homolog | 8.2 |
| DnaJ (Hsp40) homolog | 8 |
| solute carrier family 7 | 7.9 |
| vestigial like 4 (*Drosophila*) (VGLL4) | 6.5 |
| SH3 and PX domain containing 3 (SH3PX3) | 6.3 |
| cyclin E2 | 6.1 |
| SH3 and PX domain containing 3 (SH3PX3) | 6.1 |
| cyclin E2 | 6 |
| cDNA clone IMAGE: 3941306 | 5.9 |
| Paralemmin | 5.8 |
| interferon induced transmembrane protein 1 (9-27) | 5.6 |
| Paralemmin | 5.4 |
| ribulose-5-phosphate-3-epimerase | 5.4 |
| leucine-rich repeats and IQ motif containing 2 (LRRIQ2) | 5.3 |
| ribulose-5-phosphate-3-epimerase | 5.3 |
| cell division cycle associated 4 (CDCA4) | 5.2 |
| interferon induced transmembrane protein 1 (9-27) | 4.8 |
| leucine-rich repeats and IQ motif containing 2 (LRRIQ2) | 4.7 |
| mitogen-activated protein kinase-activated protein kinase 3 | 4.5 |
| calcium/calmodulin-dependent protein kinase I (CAMK1) | 4.4 |
| RAB3A interacting protein (rabin3)-like 1 (RAB3IL1) | 4.3 |
| dimethylarginine dimethylaminohydrolase 2 (DDAH2) | 4.2 |
| hsp70-interacting protein | 4.1 |
| Chromosome 9 open reading frame 11 | 4.1 |
| mitogen-activated protein kinase-activated protein kinase 3 | 4.1 |
| acrosomal vesicle protein 1 (ACRV1) | 4.1 |
| triosephosphate isomerase 1 | 4 |
| triosephosphate isomerase 1 | 3.8 |
| uroporphyrinogen III synthase (congenital erythropoietic porphyria) (UROS) | 3.7 |
| killer cell lectin-like receptor subfamily C | 3.7 |
| estrogen-related receptor alpha (ESRRA) | 3.6 |
| acrosomal vesicle protein 1 (ACRV1) | 3.6 |
| cell division cycle associated 4 (CDCA4) | 3.6 |
| RAB3A interacting protein (rabin3)-like 1 (RAB3IL1) | 3.5 |
| death-associated protein kinase 1 (DAPK1) | 3.5 |
| protein kinase C and casein kinase substrate in neurons 2 | 3.5 |
| Tropomodulin 1 | 3.4 |
| Tropomodulin 1 | 3.4 |
| Chromosome 1 open reading frame 117 | 3.4 |
| dimethylarginine dimethylaminohydrolase 2 (DDAH2) | 3.4 |

TABLE 8-continued

Antigen ID list sorted to bring on top those proteins with the highest S/N ratio. The S/N was calculated by dividing the difference of the mean signal intensity of the two groups (Cancer mean − nonCancer mean) by the standard deviation of the non-cancer group (SD non-cancer).

| Antigen Identification | Mean Diff/SD (non-cancer) |
|---|---|
| estrogen-related receptor alpha (ESRRA) | 3.2 |
| pleckstrin homology domain containing | 3.1 |
| uroporphyrinogen III synthase (congenital erythropoietic porphyria) (UROS) | 3.1 |
| hypothetical protein FLJ22795 | 3.1 |
| FYN oncogene related to SRC | 3.1 |
| mitogen-activated protein kinase-activated protein kinase 3 (MAPKAPK3) | 3.1 |
| CDC37 cell division cycle 37 homolog (S. cerevisiae)-like 1 | 3 |
| tumor suppressing subtransferable candidate 4 | 3 |
| RWD domain containing 1 | 3 |
| hypothetical protein FLJ22795 | 3 |
| CDC37 cell division cycle 37 homolog (S. cerevisiae)-like 1 | 2.9 |
| WW domain containing E3 ubiquitin protein ligase 2 | 2.9 |
| PDZ domain containing 1 (PDZK1) | 2.9 |
| mitogen-activated protein kinase-activated protein kinase 3 (MAPKAPK3) | 2.9 |
| transcription factor binding to IGHM enhancer 3 (TFE3) | 2.9 |
| forkhead box A3 (FOXA3) | 2.8 |
| Chromosome 1 open reading frame 117 | 2.8 |
| ankyrin repeat and sterile alpha motif domain containing 3 | 2.8 |
| OCIA domain containing 1 (OCIAD1) | 2.8 |
| polymerase (DNA directed) | 2.8 |
| SMAD | 2.8 |
| KIAA0157 (KIAA0157) | 2.8 |
| B-cell CLL/lymphoma 7C (BCL7C) | 2.8 |
| ribosomal protein S6 kinase | 2.8 |
| Chromosome 9 open reading frame 11 | 2.7 |
| ribosomal protein S6 kinase | 2.7 |
| cytokine induced protein 29 kDa (CIP29) | 2.7 |
| nuclear receptor binding factor 2 | 2.7 |
| host cell factor C1 regulator 1 (XPO1 dependent) (HCFC1R1) | 2.7 |
| STE20-like kinase (yeast) (SLK) | 2.7 |
| OCIA domain containing 1 (OCIAD1) | 2.6 |
| protein kinase C and casein kinase substrate in neurons 2 | 2.6 |
| quaking homolog | 2.6 |
| sorting nexin 16 (SNX16) | 2.6 |
| lymphocyte cytosolic protein 1 (L-plastin) (LCP1) | 2.6 |
| Chromosome 21 open reading frame 7 | 2.5 |
| STE20-like kinase (yeast) (SLK) | 2.5 |
| host cell factor C1 regulator 1 (XPO1 dependent) (HCFC1R1) | 2.5 |
| hsp70-interacting protein | 2.5 |
| quaking homolog | 2.5 |
| transcription factor binding to IGHM enhancer 3 (TFE3) | 2.5 |
| SMAD | 2.4 |
| WW domain containing E3 ubiquitin protein ligase 2 | 2.4 |
| Chromosome 21 open reading frame 7 | 2.4 |
| PDZ domain containing 1 (PDZK1) | 2.4 |
| acetylserotonin O-methyltransferase-like | 2.4 |
| B-cell CLL/lymphoma 7C (BCL7C) | 2.3 |
| ribosomal protein S19 (RPS19) | 2.3 |
| O-6-methylguanine-DNA methyltransferase (MGMT) | 2.3 |

By comparing the sort results of Tables 7 and 8 and examining the signals generated by cancer and non-cancer samples for each protein the following 25 proteins shown below in Table 9 were selected for further investigation.

TABLE 9

Top 25 proteins selected for further investigation.

| Clone | Antigen identification |
|---|---|
| BC007015.1 | cyclin E2 |
| NM_002614.2 | PDZ domain containing 1 (PDZK1) |
| NM_001612.3 | acrosomal vesicle protein 1 (ACRV1) |
| NM_006145.1 | DnaJ (Hsp40) homolog |
| BC011707.1 | nuclear receptor binding factor 2 |
| BC008567.1 | chromosome 21 open reading frame 7 |
| BC000108.1 | WW domain containing E3 ubiquitin protein ligase 2 |
| BC001662.1 | mitogen-activated protein kinase-activated protein kinase 3 |
| BC008037.2 | protein kinase C and casein kinase substrate in neurons 2 |
| NM_005900.1 | SMAD |
| NM_013974.1 | dimethylarginine dimethylaminohydrolase 2 (DDAH2) |
| NM_000375.1 | uroporphyrinogen III synthase (congenital erythropoietic porphyria) (UROS) |
| NM_145701.1 | cell division cycle associated 4 (CDCA4) |
| BC016848.1 | chromosome 1 open reading frame 117 |
| BC014307.1 | chromosome 9 open reading frame 11 |
| BC000897.1 | interferon induced transmembrane protein 1 (9-27) |
| NM_024548.2 | leucine-rich repeats and IQ motif containing 2 (LRRIQ2) |
| BC013778.1 | solute carrier family 7 |

TABLE 9-continued

Top 25 proteins selected for further investigation.

| Clone | Antigen identification |
|---|---|
| BC032449.1 | Paralemmin |
| NM_153271.1 | SH3 and PX domain containing 3 (SH3PX3) |
| NM_013342.1 | TCF3 (E2A) fusion partner (in childhood Leukemia) (TFPT) |
| NM_006521.3 | transcription factor binding to IGHM enhancer 3 (TFE3) |
| BC016764.1 | ribulose-5-phosphate-3-epimerase |
| BC014133.1 | CDC37 cell division cycle 37 homolog (S. cerevisiae)-like 1 |
| BC053545.1 | tropomyosin 1 (alpha) |

E. Cyclin E2

Two forms of Cyclin E2 were found to be present on the ProtoArray™. The form identified as Genbank accession BC007015.1 (SEQ ID NO:1) showed strong immunoreactivity with several of the pools of cancer samples and much lower reactivity with the benign and normal (non-cancer) pools. In contrast, the form identified as Genbank accession BC020729.1 (SEQ ID NO:2) showed little reactivity with any of the cancer or non-cancer pooled samples. As shown below, a sequence alignment of the two forms showed identity over 259 amino acids, with differences in both N-terminal and C-terminal regions. BC020729.1 has 110 amino acids at the N-terminus and 7 amino acids at the C-terminus that are not present in BC007015.1. BC007015.1 has 37 amino acids at the C-terminus that are not present in BC020729.1. Because only form BC007015.1 shows immunoreactivity, this is attributed to the 37 amino acid portion at the C-terminus.

Two peptides from the C-terminus of BC007015.1 were synthesized: E2-1 (SEQ ID NO:3) contains the C-terminal 37 amino acids of BC007015.1. E2-2 (SEQ ID NO:5) contains the C-terminal 18 amino acids of BC007015.1. Both peptides were synthesized to include a cysteine at the N terminus to provide a reactive site for specific covalent linkage to a carrier protein or surface.

Peptides E2-1 and E2-2 were each linked to BSA by activating the BSA with maleimide followed by coupling of the peptide. The activated BSA was prepared pursuant to the following protocol: To 8.0 mg of BSA in 200 uL PBS was added 1 mg GMBS (N-(gamma-maleimido-butyryl-oxy) succinimide, Pierce, Rockford Ill.) in 20 uL DMF and 10 uL 1M triethanolamine pH 8.4. After 60 minutes, the mixture was passed through a Sephadex G50 column with PBS buffer collecting 400 uL fractions. To the activated BSA-Mal (100 uL) was added either 2.5 mg of peptide E2-1 or 3.2 mg of peptide E2-2. In both cases, the mixture was vortexed and placed on ice for 15 minutes, after which the mixture was moved to room temperature for 25 minutes. The coupled products, BSA-Mal-E2-1 (BM-E2-1) and BSA-Mal-E2-2 (BM-E2-2), were passed through a Sephadex G50 column for cleanup.

Proteins and peptides were coupled to Luminex™ microspheres using two methods. The first method is described in Example 10C and is referred to as the "direct method". The second method is referred to as the "pre-activate method" and uses the following protocol: To wells of an Omega 10 k ultrafiltration plate was added 100 uL water; after 10 minutes placed on vacuum. When wells were empty, 20 uL MES (100 mM) pH 5.6 and 50 uL each Luminex™ SeroMap™ beadset were added as shown in Table 10, below. To the wells in column 1 rows A, B, C, and D and to the wells in column 2 rows A, B, C, D, and E was added 10 uL of NHS (20 mg/mL) in MES and 10 uL EDAC (10 mg/mL) in MES. After 45 minutes of shaking in the dark, the plate was placed on vacuum to suction through the buffer and unreacted reagents. When the wells were empty 100 uL MES was added and allowed to pass through the membranes. The plate was removed from vacuum and 20 uL MES and 50 uL water added. To the wells indicated in Table 10 were added 4 uL each protein or peptide (except DNAJB1, added 2 uL) and agitated with pipets to disperse the beads. The plate was

```
Sequence alignment of BC007015.1 (SEQ ID NO: 1) and BC020729.1 (SEQ ID NO:
2)
BC007015.1    1M
BC020729.1    1MSRRSSRLQAKQQPQPSQTESPQEAQIIQAKKRKTTQDVKKRREEVTKKHQYEIRNCWPP
               *

BC007015.1
BC020729.1   61VLSGGISPCIIIETPHKEIGTSDFSRFTNYRFKNLFINPSPLPDLSWGC

BC007015.1    2SKEVWLNMLKKESRYVHDKHFEVLHSDLEPQMRSILLDWLLEVCEVYTLHRETFYLAQDF
BC020729.1  110SKEVWLNMLKKESRYVHDKHFEVLHSDLEPQMRSILLDWLLEVCEVYTLHRETFYLAQDF
                ************************************************************

BC007015.1   62FDRFMLTQKDTNKNMLQLTGTTSLFTASKLEETYAPKLQEFAYVTDGACSEEDILRMELT
BC020729.1  170FDRFMLTQKDTNKNMLQLTGTTSLFTASKLEETYAPKLQEFAYVTDGACSEEDILRMELT
                ************************************************************

BC007015.1  122ILKALKWELCPVTIISWLNLFLQVDALKDAPKVLLPQYSQETFIQIAQLLDLCILAIDSL
BC020729.1  230ILKALKWELCPVTIISWLNLFLQVDALKDAPKVLLPQYSQETFIQIAQLLDLCILAIDSL
                ************************************************************

BC007015.1  182EFQYRILTAAALCHFTSIEVVKKASGLEWDSISECVDWMVPFVNVVKSTSPVKLKTFKKI
BC020729.1  290EFQYRILTAAALCHFTSIEVVKKASGLEWDSISECVDWMVPFVNVVKSTSPVKLKTFKKI
                ************************************************************

BC007015.1  242PMEDRHNIQTHTNYLAMLEEVNYINTFRKGGQLSPVCNGGIMTPPKSTEKPPGKH
BC020729.1  350PMEDRHNIQTHTNYLAMLCMISSHV
                ******************

Peptides derived from BC007015.1
E2-1            CEEVNYINTFRKGGQLSPVCNGGIMTPPKSTEKPPGKH    (SEQ ID NO: 3)

E2-2                               CNGGIMTPPKSTEKPPGKH    (SEQ ID NO: 5)
``` agitated for 30 minutes on a shaker, then 5 uL 10 mg/mL EDAC in MES was added to column 1, rows EFGH (for direct coupling), and the plate agitated on shaker for 30 minutes, then placed on vacuum to remove buffer and unreacted reagents. When the wells were empty 50 uL PBS was added and the mixtures agitated and the plate placed on vacuum. When the wells were empty 50 uL PBS was added and the mixtures agitated with pipets to disperse the beads, and incubated for 60 minutes on the shaker. To stop the reaction 200 uL PBN was added and the mixtures sonicated.

Table 10 below summarizes the different presentations of cyclin E2 peptides and proteins on the different beadsets. The peptides, E2-1 and E2-2, were coupled to BSA which was then coupled to the beads using the preactivate method (bead IDs 25 and 26) or the direct method (bead IDs 30 and 31). The peptides, E2-1 and E2-2, were also coupled to the beads without BSA using the preactivate method (bead IDs 28 and 29) or the direct method (bead IDs 33 and 34). Beads 35, 37, 38, 39, and 40 were coated with protein using the preactivate method.

TABLE 10

Summary of the different presentations of cyclin E2 peptides and proteins on different beads.

| Column | Row | Bead ID | antigen | Source | Coupling Method |
|---|---|---|---|---|---|
| 1 | A | 25 | BM-E2-1 | 3.9 mg/mL | Preactivate |
| 1 | B | 26 | BM-E2-2 | 2.4 mg/mL | Preactivate |
| 1 | C | 28 | E2-1 | 21 mg/mL | Preactivate |
| 1 | D | 29 | E2-2 | 40 mg/mL | Preactivate |
| 1 | E | 30 | BM-E2-1 | 3.9 mg/mL | Direct |
| 1 | F | 31 | BM-E2-2 | 2.4 mg/mL | Direct |
| 1 | G | 33 | E2-1 | 21 mg/mL | Direct |
| 1 | H | 34 | E2-2 | 40 mg/mL | Direct |
| 2 | A | 35 | CCNE2 | (GenWay, San Diego, CA) 0.6 mg/mL | Preactivate |
| 2 | B | 37 | MAPKAPK3 | (GenWay, San Diego, CA) 0.5 mg/mL | Preactivate |
| 2 | C | 38 | p53 | (Biomol, Plymouth Meeting, PA) 0.25 mg/mL | Preactivate |
| 2 | D | 39 | TMOD1 | (GenWay, San Diego, CA) 0.8 mg/mL | Preactivate |
| 2 | E | 40 | DNAJB1 | (Axxora, San Diego, CA) 1 mg/mL | Preactivate |

Beads were tested with patient sera in the following manner: to 1 mL PBN was added 5 uL of each bead preparation. The mixture was sonicated and centrifuged, and the pelleted beads were washed with 1 mL of BSA 1% in PBS, and resuspended in 1 mL of the same buffer. To a 1.2u Supor filter plate (Pall Corporation, East Hills, N.Y.) was added 100 uL PBN/Tween (1% BSA in PBS containing 0.2% Tween 20). After 10 minutes the plate was filtered, and 50 uL PBN 0.2% Tween (1% BSA in PBS containing 0.2% Tween 20) was added. To each well was added 20 uL bead mix and 20 uL of serum (1:50) as shown in Table 11. The serum was either human patient serum or rabbit anti-GST serum. The plate was placed on a shaker in the dark. After 1 hour, the plate was filtered and washed with 100 uL PBN/Tween three times. 50 uL of RPE-antiHuman-IgG (1:400) (Sigma, St. Louis, Mo.) was added to detect human antibodies whereas 50 uL RPE-antiRabbit-IgG (1:200) was added to detect the rabbit anti-GST antibodies. The plate was placed on a shaker in the dark for 30 minutes after which the beads were filtered, washed and run on Luminex™.

The results of six serum samples and rabbit anti-GST are shown in Table 11 below.

TABLE 11

Luminex results for beads coated with Cyclin E2 peptides and protein, exposed to patient sera.

| | Bead ID | | | | | | | | |
|---|---|---|---|---|---|---|---|---|---|
| | 25 | 26 | 28 | 29 | 35 | 30 | 31 | 33 | 34 |
| | Preactivate | | | | | Direct | | | |
| Serum ID | BM-E2-1 | BM-E2-2 | E2-1 | E2-2 | CCNE2 | BM-E2-1 | BM-E2-2 | E2-1 | E2-2 |
| A2 | 18 | 12 | 7 | 4 | 17 | 16 | 13 | 9 | 5 |
| A4 | 4 | 4 | 3 | 3 | 4 | 2 | 5 | 4 | 3 |
| B2 | 9 | 16 | 5 | 4 | 12 | 8 | 10 | 9 | 5 |
| B4 | 4380 | 172 | 1985 | 11 | 358 | 4833 | 132 | 2298 | 18 |

TABLE 11-continued

Luminex results for beads coated with Cyclin E2 peptides and protein, exposed to patient sera.

| | Bead ID | | | | | | | | |
|---|---|---|---|---|---|---|---|---|---|
| | 25 | 26 | 28 | 29 | 35 | 30 | 31 | 33 | 34 |
| | Preactivate | | | | | Direct | | | |
| Serum ID | BM-E2-1 | BM-E2-2 | E2-1 | E2-2 | CCNE2 | BM-E2-1 | BM-E2-2 | E2-1 | E2-2 |
| C4 | 227 | 44 | 66 | 9 | 50 | 243 | 40 | 87 | 7 |
| D4 | 406 | 15 | 64 | 7 | 19 | 440 | 13 | 107 | 8 |
| F4 | 3721 | 156 | 1592 | 8 | 299 | 4034 | 140 | 1997 | 19 |
| rab-antiGST | 13 | 14 | 40 | 21 | 1358 | 10 | 13 | 56 | 22 |

It is apparent from Table 11 that beads 25 and 30, containing peptide E2-1 linked to BSA and coupled directly (using the direct method) or via preactivation (or the preactivate method) of beads, respectively, gave the strongest signals. Peptide E2-1 coupled without the BSA carrier also gave strong signals, though only about one half that given with the BSA carrier. Peptide E2-2 gave much lower signals when coupled through the BSA carrier, and nearly undetectable signals without the BSA carrier. The full-length protein CCNE2 (containing an N-terminal GST fusion tag) showed signals well above those of any form of peptide E2-2, but still much below that of peptide E2-1, suggesting that it contains the immunoreactive portion of the sequence, but at lower density on the bead. Its signal with rabbit anti-GST shows that this GST fusion protein was successfully coupled to the microsphere.

The proteins shown in Table 12, below, were coated onto Luminex SeroMap™ beads by preactivation and direct methods as described above, and by passive coating. For passive coating, 5 ug of the protein, in solution as received from the vendor, was added to 200 uL of SeroMap™ beads, the mixture vortexed, and incubated 5 hours at room temperature, then 18 hours at 4° C., then centrifuged to sediment, and the pellet washed and resuspended in PBN.

TABLE 12

Proteins coated onto Luminex SeroMap™ beads by preactivation and direct methods.

| Coating | Protein | Bead | Source |
|---|---|---|---|
| Preactivate | TMP21-ECD | 1 | Abbott, North Chicago, IL |
| Preactivate | NPC1L1C-domain | 5 | Abbott, North Chicago, IL |
| Preactivate | PSEN2(1-86aa) | 14 | Abbott, North Chicago, IL |
| Preactivate | IgG human | 22 | Abbott, North Chicago, IL |
| Preactivate | BM-E2-2 | 26 | Abbott, North Chicago, IL |
| Direct | BM-E2-1 | 30 | Abbott, North Chicago, IL |
| Preactivate | TMOD1 | 39 | Genway, San Diego, CA |
| Preactivate | DNAJB1 | 40 | Axxora, San Diego, CA |
| Preactivate | PSMA4 | 41 | Abnova, Taipei City, Taiwan |
| Preactivate | RPE | 42 | Abnova, Taipei City, Taiwan |
| Preactivate | CCNE2 | 43 | Abnova, Taipei City, Taiwan |
| Preactivate | PDZK1 | 46 | Abnova, Taipei City, Taiwan |
| Direct | CCNE2 | 49 | Genway, San Diego, CA |
| Preactivate | Paxilin | 53 | BioLegend, San Diego, CA |
| Direct | AMPHIPHYSIN | 54 | LabVision, Fremont, CA |
| Preactivate | CAMK1 | 55 | Upstate, Charlottesville, VA |
| Passive | DNAJB11 | 67 | Abnova, Taipei City, Taiwan |
| Passive | RGS1 | 68 | Abnova, Taipei City, Taiwan |
| Passive | PACSIN1 | 70 | Abnova, Taipei City, Taiwan |
| Passive | SMAD1 | 71 | Abnova, Taipei City, Taiwan |
| Passive | p53 | 72 | Biomol, Plymouth Meeting, PA |
| Passive | RCV1 | 75 | Genway, San Diego, CA |
| Passive | MAPKAPK3 | 79 | Genway, San Diego, CA |

Serum samples from 234 patients (87 cancers, 70 benigns, and 77 normals) were tested. Results from this testing were analyzed by ROC curves. The calculated AUC for each antigen is shown in Table 13 below.

TABLE 13

Calculated AUC for antigens derived from serum samples.

| Protein | AUC |
|---|---|
| cyclin E2 peptide 1 | 0.81 |
| cyclin E2 protein (Genway) | 0.74 |
| cyclin E2 peptide2 | 0.71 |
| TMP21-ECD | 0.66 |
| NPC1L1C-domain | 0.65 |
| PACSIN1 | 0.65 |
| p53 | 0.63 |
| mitogen activated protein kinase activated protein kinase (MAPKAPK3) | 0.62 |
| Tropomodulin 1 (TMOD1) | 0.61 |
| PSEN2(1-86aa) | 0.60 |
| DNA J binding protein 1(DNAJB1) | 0.60 |
| DNA J binding protein 11(DNAJB11) | 0.58 |
| RCV1 | 0.58 |
| (calcium/calmodulin - dependent protein kinase 1 CAMK1) | 0.57 |
| SMAD1 | 0.57 |
| AMPHIPHYSIN Lab Vision | 0.55 |
| RGS1 | 0.55 |
| PSMA4 | 0.51 |
| ribulose-5-phosphate-3-epimerase (RPE) | 0.51 |
| Paxilin | 0.51 |
| cyclin E2 protein (Abnova) | 0.49 |
| PDZ domain containing protein 1(PDZK1) | 0.47 |

Example 5

Mass Spectrometry

A. Sample Preparation by Sequential Elution of a Mixed Magnetic Bead (MMB)

The sera samples were thawed and mixed with equal volume of Invitrogen's Sol B buffer. The mixture was vortexed and filtered through a 0.8 μm filter (Sartorius, Goettingen, Germany) to clarify and remove debris before further processing. Automated Sample preparation was performed on a 96-well plate KingFisher® (Thermo Fisher, Scientific, Inc., Waltham, Mass.) using a mixture of Dynal® (Invitrogen) strong anion exchange and Abbott Laboratories (Abbott, Abbott Park, Ill.) weak cation exchange magnetic beads. Typically anion exchange beads have amine based hydrocarbons—quaternary amines or diethyl amine groups—as the functional end groups and the weak cation exchange beads typically have sulphonic acid (carboxylic acid) based functional groups. Abbott's cation exchange beads (CX beads) were at concentration of 2.5% (mass/volume) and the Dynal® strong anion exchange beads (AX beads) were at 10 mg/ml concentration. Just prior to sample preparation, cation exchange beads were washed once with 20 mM Tris.HCl, pH 7.5, 0.1% reduced Triton X100 (Tris-Triton buffer). Other reagents, 20 mM Tris.HCl, pH 7.5 (Tris buffer), 0.5% Trifluoroacetic acid (hereinafter "TFA solution") and 50% Acetonitrile (hereinafter "Acetonitrile solution"), used in this sample preparation and were prepared in-house. The reagents and samples were setup in the 96-well plate as follows:

Row A contained a mixture of 30 ul of AX beads, 20 ul of CX beads and 50 uL of Tris buffer.

Row B contained 100 uL of Tris buffer.

Row C contained 120 uL of Tris buffer and 30 uL of sample.

Row D contained 100 uL of Tris buffer.

Row E contained 100 uL of deionized water.

Row F contained 50 uL of TFA solution.

Row G contained 50 uL of Acetonitrile solution.

Row H was empty.

The beads and buffer in row A are premixed and the beads collected with Collect count of 3 (instrument parameter that indicates how many times the magnetic probe goes into solution to collect the magnetic beads) and transferred over to row B for wash in Tris buffer—with release setting "fast", wash setting—medium, and wash time of 20 seconds. At the end of bead wash step, the beads are collected with Collect count of 3 and transferred over to row C to bind the sample. The bead release setting is fast. The sample binding is performed with "slow" setting, with binding time of 5 minutes. At the end of binding step, the beads are collected with Collect count of 3. The collected beads are transferred over to row D for the first wash step—release setting "fast", wash setting—medium, with wash time of 20 seconds. At the end of first wash step, the beads are collected with Collect count of 3. The collected beads are transferred over to row E for the second wash step—release setting "fast", wash setting—medium, with wash time of 20 seconds. At the end of second wash step, the beads are collected with Collect count of 3. The collected beads are transferred over to row F for elution in TFA solution—with release setting "fast", elution setting—fast and elution time of 2 minutes. At the end of TFA elution step, the beads are collected with Collect count of 3. This TFA eluent was collected and analysed by mass spectrometry. The collected beads are transferred over to row G for elution in Acetonitrile solution—with release setting "fast", elution setting—fast and elution time of 2 minutes. After elution, the beads are removed with Collect count of 3 and disposed of in row A. The Acetonitrile (AcN) eluent was collected and analysed by mass spectrometry.

All the samples were run in duplicate, but not on the same plate to avoid systematic errors. The eluted samples were manually aspirated and placed in 96-well plates for automated MALDI target sample preparation. Thus, each sample provided two eluents for mass spectrometry analysis.

A CLINPROT robot (Bruker Daltonics Inc., Billerica, Mass.) was used for preparing the MALDI targets prior to MS interrogation. Briefly, the process involved loading the sample plate containing the eluted serum samples and the vials containing the MALDI matrix solution (10 mg/mL Sinapinic acid in 70% Acetonitrile) in the designated positions on the robot. A file containing the spotting procedure was loaded and initiated from the computer that controls the robot. In this case, the spotting procedure involved aspirating 5 uL of matrix solution and dispensing it in the matrix plate followed by 5 uL of sample. Premixing of sample and matrix was accomplished by aspirating 5 uL of the mixture and dispensing it several times in the matrix plate. After premixing, 5 uL of the mixture was aspirated and 0.5 uL was deposited on four contiguous spots on the anchor chip target (Bruker Daltonics Inc., Billerica, Mass.). The remaining 3 uL of solution was disposed of in the waste container. Aspirating more sample than was needed minimized the formation of air bubbles in the disposable tips that may lead to missed spots during sample deposition on the anchor chip target.

B. Sample Preparation by C8 Magnetic Bead Hydrophobic Interaction Chromatography (C8 MB-HIC)

The sera samples were mixed with SOLB buffer and clarified with filters as described in Example 5A. Automated Sample preparation was performed on a 96-well plate KingFisher® using CLINPROT Purification Kits known as 100 MB-HIC 8 (Bruker Daltonics Inc., Billerica, Mass.). The kit includes C8 magnetic beads, binding solution, and wash solution. All other reagents were purchased from Sigma Chem. Co., if not stated otherwise. The reagents and samples were setup in the 96-well plate as follows:

Row A contained a mixture of 20 uL of Bruker's C8 magnetic beads and 80 uL of DI water.

Row B contained a mixture of 10 uL of serum sample and 40 uL of binding solution. Rows C-E contained 100 uL of wash solution.

Row F contained 50 uL of 70% acetonitrile (added just prior to the elution step to minimize evaporation of the organic solvent).

Row G contained 100 uL of DI water.

Row H was empty.

The beads in row A were premixed and collected with a "Collect count" of 3 and transferred over to row B to bind the sample. The bead release setting was set to "fast" with a release time of 10 seconds. The sample binding was performed with the "slow" setting for 5 minutes. At the end of binding step, the beads were collected with a "Collect count" of 3 and transferred over to row C for the first wash step (release setting=fast with time=10 seconds, wash setting=medium with time=20 seconds). At the end of first wash step, the beads were collected with a "Collect count" of 3 and transferred over to row D for a second washing step with the same parameters as in the first washing step. At the end of second wash step, the beads were collected once more and transferred over to row E for a third and final wash step as previously described. At the end of the third wash step, the KingFisher™ was paused during the transfer step from Row E to Row F and 50 uL of 70% acetonitrile was added to Row F. After the acetonitrile addition, the process was resumed. The collected beads from Row E were transferred to Row F for the elution step (release setting=fast with time=10 seconds, elution setting=fast with time=2 minutes). After the elution step, the beads were removed and disposed of in row G. All the samples were run in duplicate, as described above in Example 5a.

A CLINPROT robot (Bruker Daltonics Inc., Billerica, Mass.) was used for preparing the MALDI targets prior to MS interrogation as described in the previous section with only minor modifications in the MALDI matrix used. In this case, instead of SA, HCCA was used (1 mg/mL HCCA in 40% ACN/50% MeOH/10% water, v/v/v). All other parameters remained the same.

C. Sample Preparation Using SELDI Chip

The following reagents were used:
1. 100 mM phosphate buffer, pH 7.0, prepared by mixing 250 mL deionized water with 152.5 mL of 200 mM disodium phosphate solution and 97.5 mL of 200 mM monosodium phosphate solution.
2. 10 mg/mL sinapinic acid solution, prepared by dissolving a weighed amount of sinapinic acid in a sufficient quantity of a solution prepared by mixing equal volumes of acetonitrile and 0.4% aqueous trifluoroacetic acid (v/v) to give a final concentration of 10 mg sinapinic acid per mL solution.
3. Deionized water, Sinapinic acid and trifluoroacetic acid were from Fluka Chemicals. Acetonitrile was from Burdick and Jackson.

Q10 ProteinChip arrays in the eight spot configuration and Bioprocessors used to hold the arrays in a 12×8 array with a footprint identical with a standard microplate were obtained from Ciphergen. The Q10 active surface is a quaternary amine strong anion exchanger. A Ciphergen ProteinChip System, Series 4000 Matrix Assisted Laser Desorption Ionization (MALDI) time of flight mass spectrometer was used to analyze the peptides bound to the chip surface. All Ciphergen products were obtained from Ciphergen Biosystems, Dumbarton, Calif.

All liquid transfers, dilutions, and washes were performed by a Hamilton Microlab STAR robotic pipettor from the Hamilton Company, Reno, Nev.

Serum samples were thawed at room temperature and mixed by gentle vortexing. The vials containing the sample were loaded into 24 position sample holders on the Hamilton pipettor; four sample holders with a total of 96 samples were loaded. Two Bioprocessors holding Q10 chips (192 total spots) were placed on the deck of the Hamilton pipettor. Containers with 100 mM phosphate buffer and deionized water were loaded onto the Hamilton pipettor. Disposable pipette tips were also placed on the deck of the instrument.

All sample processing was totally automated. Each sample was diluted 1 to 10 into two separate aliquots by mixing 5 microliters of serum with 45 microliters of phosphate buffer in two separate wells of a microplate on the deck of the Hamilton pipettor. Q10 chips were activated by exposing each spot to two 150 microliter aliquots of phosphate buffer. The buffer was allowed to activate the surface for 5 minutes following each addition. After the second aliquot was aspirated from each spot, 25 microliters of diluted serum was added to each spot and incubated for 30 minutes at room temperature. Each sample was diluted twice with a single aliquot from each dilution placed on a spot of a Q10 chip. Following aspiration of the diluted serum, each spot was washed four times with 150 microliters of phosphate buffer and finally with 150 microliters of deionized water. The processed chips were air dried and treated with sinapinic acid, the matrix used to enable the MALDI process in the Ciphergen 4000. The sinapinic acid matrix solution was loaded onto the Hamilton pipettor by placing a 96 well microplate, each well filled with sinapinic acid solution, onto the deck of the instrument. A 96 head pipettor was used to add 1 microliter of sinapinic acid matrix to each spot on a Bioprocessor simultaneously. After a 15 minute drying period, a second 1 microliter aliquot was added to each spot and allowed to dry.

D. AutoFlex MALDI-TOF Data Acquisition of Mixed Bead Sample Prep

The instrument's acquisition range was set from m/z 400 to 100,000. The instrument was externally calibrated in linear mode using Bruker's calibration standards covering a mass range from 2-17 kDa. In order to collect high quality spectra, the acquisitions were fully automated with the fuzzy control on, except for the laser. The laser's fuzzy control was turned off so that the laser power remained constant for the duration of the experiment. Since the instrument is generally calibrated at a fixed laser power, accuracy benefits from maintaining a constant laser power. The other fuzzy control settings controlled the resolution and S/N of peaks in the mass range of 2-10 kDa. These values were optimized prior to each acquisition and chosen to maximize the quality of the spectra while minimizing the number of failed acquisitions from sample to sample or spot to spot. The deflector was also turned on to deflect low molecular mass ions (<400 m/z) to prevent saturating the detector with matrix ions and maximizing the signal coming from the sample. In addition, prior to each acquisition, 5 warming shots (LP ca. 5-10% above the threshold) were fired to remove any excess matrix as the laser beam is rastered across the sample surface. For each mass spectrum, 600 laser shots were co-added together only if they met the resolution and S/N criteria set above. All other spectra of inferior quality were ignored and discarded and no baseline correction or smoothing algorithms were used during the acquisition of the raw spectra.

The data were archived, transformed into a common m/z axis to facilitate comparison and exported in a portable ASCII format that could be analyzed by various statistical software packages. The transformation into a common m/z axis was accomplished by using an interpolating algorithm developed in-house.

E. AutoFlex MALDI-TOF Data Acquisition of C8 MB-HIC

The instrument's acquisition range was set from m/z 1000 to 20,000 and optimized for sensitivity and resolution. All other acquisition parameters and calibration methods were set as described above in Example 5d, with the exception that 400 laser shots were co-added for each mass spectrum.

F. Ciphergen 4000 SELDI-TOF Data Acquisition of Q-10 Chip.

The Bioprocessors were loaded onto a Ciphergen 4000 MALDI time of flight mass spectrometer using the optimized parameters for the mass range between 0-50,000 Da. The data were digitized and averaged over the 530 acquisitions per spot to obtain a single spectrum of ion current vs. mass/charge (m/z). Each spectrum was exported to a server and subsequently retrieved as an ASCII file for post acquisition analysis.

G. Region of Interest Analysis of Mass Spectrometry Data

The mass spectrometric data consists of mass/charge values from 0-50,000 and their corresponding intensity values. Cancer and Non-Cancer data sets were constructed. The Cancer data set consists of the mass spectra from all cancer samples, whereas Non-Cancer data set consists of mass spectra from every non-cancer sample, including normal subjects and patients with benign lung disease. The Cancer and Non-Cancer data sets were separately uploaded in a software program that performs the following:

a) Student's t-test is determined at every recorded mass/charge value to give a p-value.
b) The Cancer and Non-Cancer spectra are averaged to one representative for each group.

c) The logarithmic ratio (Log Ratio) of intensity of average cancer spectra and average non-cancer spectra is determined.

ROIs were specified to have ten or more consecutive mass values with a p-value of less than 0.01 and an absolute Log Ratio of greater than 0.1. 18, 36, and 26 ROIs were found in the MMB-TFA, MMB-AcN, and MB-HIC datasets respectively (Tables 14a-14c). Further, 124 ROIs (<20 kDa) were found in the SELDI data as shown in Table 14d. Tables 14a to 14d list the ROIs of the present invention, sorted by increasing average mass value. The ROI provided in the table is the average mass value for the calculated interval (average of the start and ending mass value for the given interval). The average ROI mass will be referred to as simply the ROI from here on. The intensities of each ROI for each sample were subjected to ROC analysis. The AUC for each marker is also reported in the Tables 14a-14d below. In Tables 14a-14c below, the calculated ROI obtained from the analysis of MS profiles of diseased and non-diseased groups. Individual samples were processed using three different methods: mixed magnetic bead anion/cation exchange chromatography eluted with a) TFA (tfa) and eluted sequentially with b) acetonitrile (acn), c) using hydrophobic interaction chromatography (hic). Each sample preparation method was analyzed independently for the purpose of obtaining ROI. All the spectra were collected with a Bruker AutoFlex MALDI-TOF mass spectrometer. In Table 14d below, the calculated ROI obtained from the analysis of MS profiles of diseased and non-diseased groups. All the samples were processed using a Q-10 chip. All spectra were collected using a Ciphergen 4000 SELDI-TOF Mass Spectrometer.

TABLE 14a

| ROI start m/z | ROI end m/z | Average ROI | ROI name | large cohort # obs | large cohort AUC | small cohort # obs | small cohort AUC |
|---|---|---|---|---|---|---|---|
| 2322.911 | 2339.104 | 2331 | tfa2331 | 538 | 0.66 | 236 | 0.52 |
| 2394.584 | 2401.701 | 2398 | tfa2398 | 538 | 0.68 | 236 | 0.55 |
| 2756.748 | 2761.25 | 2759 | tfa2759 | 538 | 0.65 | 236 | 0.60 |
| 2977.207 | 2990.847 | 2984 | tfa2984 | 538 | 0.69 | 236 | 0.52 |
| 3010.649 | 3021.701 | 3016 | tfa3016 | 538 | 0.63 | 236 | 0.48 |
| 3631.513 | 3639.602 | 3636 | tfa3635 | 538 | 0.61 | 236 | 0.54 |
| 4188.583 | 4198.961 | 4194 | tfa4193 | 538 | 0.60 | 236 | 0.56 |
| 4317.636 | 4324.986 | 4321 | tfa4321 | 538 | 0.61 | 236 | 0.51 |
| 5000.703 | 5015.736 | 5008 | tfa5008 | 538 | 0.70 | 236 | 0.57 |
| 5984.935 | 5990.126 | 5988 | tfa5987 | 538 | 0.70 | 236 | 0.49 |
| 6446.144 | 6459.616 | 6453 | tfa6453 | 538 | 0.74 | 236 | 0.65 |
| 6646.05 | 6658.513 | 6652 | tfa6652 | 538 | 0.72 | 236 | 0.71 |
| 6787.156 | 6837.294 | 6812 | tfa6815 | 538 | 0.71 | 236 | 0.53 |
| 8141.621 | 8155.751 | 8149 | tfa8148 | 538 | 0.62 | 236 | 0.64 |
| 8533.613 | 8626.127 | 8580 | tfa8579 | 538 | 0.71 | 236 | 0.58 |
| 8797.964 | 8953.501 | 8876 | tfa8872 | 538 | 0.68 | 236 | 0.52 |
| 9129.621 | 9143.87 | 9137 | tfa9133 | 538 | 0.63 | 236 | 0.60 |
| 12066.33 | 12093.36 | 12080 | tfa12079 | 538 | 0.66 | 236 | 0.63 |

TABLE 14b

| ROI start m/z | ROI end m/z | Average ROI | ROI name | large cohort # obs | large cohort AUC | small cohort # obs | small cohort AUC |
|---|---|---|---|---|---|---|---|
| 3022.726 | 3026.825 | 3025 | acn3024 | 519 | 0.63 | 244 | 0.51 |
| 3144.614 | 3182.554 | 3164 | acn3163 | 519 | 0.70 | 244 | 0.60 |
| 3183.395 | 3188.023 | 3186 | acn3186 | 519 | 0.63 | 244 | 0.54 |
| 4128.262 | 4135.209 | 4132 | acn4132 | 519 | 0.61 | 244 | 0.59 |
| 4152.962 | 4161.372 | 4157 | acn4157 | 519 | 0.65 | 244 | 0.65 |
| 4183.519 | 4194.373 | 4189 | acn4189 | 519 | 0.52 | 244 | 0.55 |
| 4627.389 | 4635.759 | 4632 | acn4631 | 519 | 0.74 | 244 | 0.68 |
| 5049.048 | 5114.402 | 5082 | acn5082 | 519 | 0.68 | 244 | 0.62 |
| 5229.648 | 5296.428 | 5263 | acn5262 | 519 | 0.68 | 244 | 0.61 |
| 5338.006 | 5374.554 | 5356 | acn5355 | 519 | 0.64 | 244 | 0.52 |
| 5375.101 | 5383.848 | 5379 | acn5378 | 519 | 0.67 | 244 | 0.62 |
| 5446.925 | 5457.382 | 5452 | acn5455 | 519 | 0.68 | 244 | 0.54 |
| 5971.68 | 5981.476 | 5977 | acn5976 | 519 | 0.64 | 244 | 0.58 |
| 6150.986 | 6166.194 | 6159 | acn6158 | 519 | 0.63 | 244 | 0.54 |
| 6314.273 | 6338.877 | 6327 | acn6326 | 519 | 0.62 | 244 | 0.58 |
| 6391.206 | 6406.112 | 6399 | acn6399 | 519 | 0.67 | 244 | 0.60 |
| 6455.723 | 6461.713 | 6459 | acn6458 | 519 | 0.56 | 244 | 0.65 |
| 6574.845 | 6607.218 | 6591 | acn6592 | 519 | 0.68 | 244 | 0.58 |
| 6672.509 | 6689.568 | 6681 | acn6681 | 519 | 0.53 | 244 | 0.70 |
| 8759.205 | 8791.323 | 8775 | acn8775 | 519 | 0.64 | 244 | 0.58 |
| 8850.827 | 8888.382 | 8870 | acn8871 | 519 | 0.69 | 244 | 0.55 |
| 9067.056 | 9095.468 | 9081 | acn9080 | 519 | 0.65 | 244 | 0.57 |
| 9224.586 | 9277.996 | 9251 | acn9251 | 519 | 0.64 | 244 | 0.59 |
| 9358.22 | 9384.195 | 9371 | acn9371 | 519 | 0.65 | 244 | 0.55 |
| 9453.639 | 9467.414 | 9461 | acn9459 | 519 | 0.66 | 244 | 0.76 |
| 9470.315 | 9473.579 | 9472 | acn9471 | 519 | 0.70 | 244 | 0.71 |
| 9651.055 | 9674.867 | 9663 | acn9662 | 519 | 0.66 | 244 | 0.52 |
| 10008.34 | 10022.51 | 10015 | acn10015 | 519 | 0.63 | 244 | 0.56 |
| 10217.84 | 10221.98 | 10220 | acn10216 | 519 | 0.64 | 244 | 0.55 |
| 10669.51 | 10689.53 | 10680 | acn10679 | 519 | 0.61 | 244 | 0.52 |
| 10866.73 | 10886.56 | 10877 | acn10877 | 519 | 0.63 | 244 | 0.50 |
| 11371.68 | 11745.49 | 11559 | acn11559 | 519 | 0.63 | 244 | 0.68 |
| 14293.87 | 14346.94 | 14320 | acn14319 | 519 | 0.62 | 244 | 0.58 |
| 22764.38 | 22771.69 | 22768 | acn22768 | 519 | 0.68 | 244 | 0.62 |
| 22778.44 | 22788 | 22783 | acn22783 | 519 | 0.68 | 244 | 0.63 |
| 22791.38 | 23147.21 | 22969 | acn22969 | 519 | 0.70 | 244 | 0.63 |

TABLE 14c

| ROI start m/z | ROI end m/z | Average ROI | ROI name | large cohort # obs | large cohort AUC | small cohort # obs | small cohort AUC |
|---|---|---|---|---|---|---|---|
| 2016.283 | 2033.22 | 2025 | hic2025 | 529 | 0.65 | 245 | 0.53 |
| 2304.447 | 2308.026 | 2306 | hic2306 | 529 | 0.64 | 245 | 0.66 |
| 2444.629 | 2457.914 | 2451 | hic2451 | 529 | 0.60 | 245 | 0.50 |
| 2504.042 | 2507.867 | 2506 | hic2506 | 529 | 0.65 | 245 | 0.53 |
| 2642.509 | 2650.082 | 2646 | hic2646 | 529 | 0.54 | 245 | 0.45 |
| 2722.417 | 2733.317 | 2728 | hic2728 | 529 | 0.61 | 245 | 0.56 |
| 2971.414 | 2989.522 | 2980 | hic2980 | 529 | 0.64 | 245 | 0.53 |
| 3031.235 | 3037.804 | 3035 | hic3035 | 529 | 0.54 | 245 | 0.45 |
| 3161.146 | 3191.075 | 3176 | hic3176 | 529 | 0.70 | 245 | 0.61 |
| 3270.723 | 3280.641 | 3276 | hic3276 | 529 | 0.64 | 245 | 0.57 |
| 3789.504 | 3797.883 | 3794 | hic3794 | 529 | 0.64 | 245 | 0.57 |
| 3942.315 | 3975.73 | 3959 | hic3959 | 529 | 0.74 | 245 | 0.59 |
| 4999.913 | 5006.107 | 5003 | hic5003 | 529 | 0.66 | 245 | 0.56 |
| 5367.59 | 5384.395 | 5376 | hic5376 | 529 | 0.68 | 245 | 0.48 |
| 6002.824 | 6006.289 | 6005 | hic6005 | 529 | 0.69 | 245 | 0.51 |
| 6181.86 | 6195.934 | 6189 | hic6189 | 529 | 0.72 | 245 | 0.51 |
| 6380.634 | 6382.272 | 6381 | hic6381 | 529 | 0.70 | 245 | 0.55 |
| 6382.569 | 6392.1 | 6387 | hic6387 | 529 | 0.71 | 245 | 0.54 |
| 6438.218 | 6461.563 | 6450 | hic6450 | 529 | 0.66 | 245 | 0.57 |
| 6640.279 | 6658.057 | 6649 | hic6649 | 529 | 0.62 | 245 | 0.59 |
| 6815.125 | 6816.816 | 6816 | hic6816 | 529 | 0.72 | 245 | 0.56 |
| 6821.279 | 6823.896 | 6823 | hic6823 | 529 | 0.71 | 245 | 0.58 |
| 8788.878 | 8793.595 | 8791 | hic8791 | 529 | 0.58 | 245 | 0.47 |
| 8892.247 | 8901.211 | 8897 | hic8897 | 529 | 0.61 | 245 | 0.52 |
| 8908.948 | 8921.088 | 8915 | hic8915 | 529 | 0.64 | 245 | 0.55 |
| 9298.469 | 9318.065 | 9308 | hic9308 | 529 | 0.68 | 245 | 0.59 |

TABLE 14d

| ROI start m/z | ROI end m/z | Average ROI | ROI name | large cohort # obs | AUC | small cohort # obs | AUC |
|---|---|---|---|---|---|---|---|
| 2327 | 2336 | 2331 | Pub2331 | 513 | 0.65 | 250 | 0.62 |
| 2368 | 2371 | 2369 | Pub2369 | 513 | 0.64 | 250 | 0.60 |
| 2384 | 2389 | 2387 | Pub2386 | 513 | 0.67 | 250 | 0.62 |
| 2410 | 2415 | 2413 | Pub2412 | 513 | 0.67 | 250 | 0.63 |
| 2431 | 2435 | 2433 | Pub2433 | 513 | 0.72 | 250 | 0.72 |
| 2453 | 2464 | 2459 | Pub2458 | 513 | 0.70 | 250 | 0.62 |
| 2672 | 2682 | 2677 | Pub2676 | 513 | 0.73 | 250 | 0.68 |
| 2947 | 2955 | 2951 | Pub2951 | 513 | 0.72 | 250 | 0.64 |
| 2973 | 2979 | 2976 | Pub2976 | 513 | 0.63 | 250 | 0.58 |
| 3016 | 3020 | 3018 | Pub3018 | 513 | 0.50 | 250 | 0.51 |
| 3168 | 3209 | 3189 | Pub3188 | 513 | 0.69 | 250 | 0.59 |
| 3347 | 3355 | 3351 | Pub3351 | 513 | 0.70 | 250 | 0.67 |
| 3409 | 3414 | 3412 | Pub3411 | 513 | 0.60 | 250 | 0.57 |
| 3441 | 3456 | 3449 | Pub3448 | 513 | 0.72 | 250 | 0.58 |
| 3484 | 3503 | 3494 | Pub3493 | 513 | 0.72 | 250 | 0.67 |
| 3525 | 3531 | 3528 | Pub3527 | 513 | 0.62 | 250 | 0.55 |
| 3548 | 3552 | 3550 | Pub3550 | 513 | 0.62 | 250 | 0.62 |
| 3632 | 3650 | 3641 | Pub3640 | 513 | 0.63 | 250 | 0.57 |
| 3656 | 3662 | 3659 | Pub3658 | 513 | 0.51 | 250 | 0.49 |
| 3678 | 3688 | 3683 | Pub3682 | 513 | 0.72 | 250 | 0.69 |
| 3702 | 3709 | 3706 | Pub3705 | 513 | 0.57 | 250 | 0.55 |
| 3737 | 3750 | 3744 | Pub3743 | 513 | 0.69 | 250 | 0.67 |
| 3833 | 3845 | 3839 | Pub3839 | 513 | 0.62 | 250 | 0.59 |
| 3934 | 3955 | 3944 | Pub3944 | 513 | 0.65 | 250 | 0.57 |
| 4210 | 4217 | 4214 | Pub4213 | 513 | 0.62 | 250 | 0.56 |
| 4299 | 4353 | 4326 | Pub4326 | 513 | 0.69 | 250 | 0.59 |
| 4442 | 4448 | 4445 | Pub4444 | 513 | 0.61 | 250 | 0.52 |
| 4458 | 4518 | 4488 | Pub4487 | 513 | 0.75 | 250 | 0.69 |
| 4535 | 4579 | 4557 | Pub4557 | 513 | 0.73 | 250 | 0.68 |
| 4590 | 4595 | 4592 | Pub4592 | 513 | 0.70 | 250 | 0.66 |
| 4611 | 4647 | 4629 | Pub4628 | 513 | 0.77 | 250 | 0.66 |
| 4677 | 4687 | 4682 | Pub4682 | 513 | 0.72 | 250 | 0.69 |
| 4698 | 4730 | 4714 | Pub4713 | 513 | 0.73 | 250 | 0.70 |
| 4742 | 4759 | 4751 | Pub4750 | 513 | 0.76 | 250 | 0.73 |
| 4779 | 4801 | 4790 | Pub4789 | 513 | 0.70 | 250 | 0.72 |
| 4857 | 4865 | 4861 | Pub4861 | 513 | 0.72 | 250 | 0.75 |
| 4987 | 4996 | 4992 | Pub4991 | 513 | 0.67 | 250 | 0.57 |
| 5016 | 5056 | 5036 | Pub5036 | 513 | 0.65 | 250 | 0.54 |
| 5084 | 5194 | 5139 | Pub5139 | 513 | 0.61 | 250 | 0.51 |
| 5208 | 5220 | 5214 | Pub5213 | 513 | 0.57 | 250 | 0.52 |
| 5246 | 5283 | 5265 | Pub5264 | 513 | 0.59 | 250 | 0.56 |
| 5295 | 5420 | 5357 | Pub5357 | 513 | 0.64 | 250 | 0.54 |
| 5430 | 5537 | 5484 | Pub5483 | 513 | 0.62 | 250 | 0.54 |
| 5570 | 5576 | 5573 | Pub5573 | 513 | 0.59 | 250 | 0.57 |
| 5590 | 5595 | 5593 | Pub5592 | 513 | 0.60 | 250 | 0.54 |
| 5612 | 5619 | 5615 | Pub5615 | 513 | 0.55 | 250 | 0.53 |
| 5639 | 5648 | 5644 | Pub5643 | 513 | 0.68 | 250 | 0.63 |
| 5679 | 5690 | 5685 | Pub5684 | 513 | 0.66 | 250 | 0.59 |
| 5752 | 5804 | 5778 | Pub5777 | 513 | 0.71 | 250 | 0.63 |
| 5839 | 5886 | 5862 | Pub5862 | 513 | 0.73 | 250 | 0.67 |
| 5888 | 5909 | 5898 | Pub5898 | 513 | 0.63 | 250 | 0.56 |
| 6008 | 6018 | 6013 | Pub6013 | 513 | 0.61 | 250 | 0.57 |
| 6047 | 6058 | 6053 | Pub6052 | 513 | 0.64 | 250 | 0.63 |
| 6087 | 6103 | 6095 | Pub6094 | 513 | 0.59 | 250 | 0.54 |
| 6111 | 6124 | 6118 | Pub6117 | 513 | 0.70 | 250 | 0.67 |
| 6153 | 6160 | 6156 | Pub6156 | 513 | 0.57 | 250 | 0.51 |
| 6179 | 6188 | 6183 | Pub6183 | 513 | 0.65 | 250 | 0.60 |
| 6192 | 6198 | 6195 | Pub6194 | 513 | 0.57 | 250 | 0.49 |
| 6226 | 6272 | 6249 | Pub6249 | 513 | 0.66 | 250 | 0.63 |
| 6277 | 6286 | 6281 | Pub6281 | 513 | 0.62 | 250 | 0.65 |
| 6297 | 6307 | 6302 | Pub6302 | 513 | 0.71 | 250 | 0.67 |
| 6352 | 6432 | 6392 | Pub6391 | 513 | 0.65 | 250 | 0.56 |
| 6497 | 6570 | 6534 | Pub6533 | 513 | 0.63 | 250 | 0.59 |
| 6572 | 6603 | 6587 | Pub6587 | 513 | 0.60 | 250 | 0.55 |
| 6698 | 6707 | 6702 | Pub6702 | 513 | 0.57 | 250 | 0.52 |
| 6715 | 6723 | 6719 | Pub6718 | 513 | 0.64 | 250 | 0.57 |
| 6748 | 6849 | 6799 | Pub6798 | 513 | 0.77 | 250 | 0.69 |
| 7197 | 7240 | 7219 | Pub7218 | 513 | 0.73 | 250 | 0.65 |
| 7250 | 7262 | 7256 | Pub7255 | 513 | 0.72 | 250 | 0.65 |
| 7310 | 7326 | 7318 | Pub7317 | 513 | 0.71 | 250 | 0.65 |
| 7401 | 7427 | 7414 | Pub7413 | 513 | 0.73 | 250 | 0.69 |
| 7435 | 7564 | 7499 | Pub7499 | 513 | 0.76 | 250 | 0.73 |
| 7611 | 7616 | 7614 | Pub7613 | 513 | 0.67 | 250 | 0.60 |
| 7634 | 7668 | 7651 | Pub7651 | 513 | 0.70 | 250 | 0.63 |
| 7699 | 7723 | 7711 | Pub7711 | 513 | 0.72 | 250 | 0.66 |
| 7736 | 7748 | 7742 | Pub7742 | 513 | 0.69 | 250 | 0.65 |
| 7768 | 7782 | 7775 | Pub7775 | 513 | 0.63 | 250 | 0.57 |
| 7935 | 7954 | 7945 | Pub7944 | 513 | 0.64 | 250 | 0.61 |
| 7976 | 7985 | 7981 | Pub7980 | 513 | 0.62 | 250 | 0.59 |
| 7999 | 8006 | 8003 | Pub8002 | 513 | 0.58 | 250 | 0.60 |
| 8134 | 8239 | 8186 | Pub8186 | 513 | 0.73 | 250 | 0.62 |
| 8286 | 8308 | 8297 | Pub8297 | 513 | 0.69 | 250 | 0.62 |
| 8448 | 8461 | 8455 | Pub8454 | 513 | 0.61 | 250 | 0.59 |
| 8476 | 8516 | 8496 | Pub8496 | 513 | 0.69 | 250 | 0.64 |
| 8526 | 8567 | 8547 | Pub8546 | 513 | 0.73 | 250 | 0.66 |
| 8579 | 8634 | 8606 | Pub8606 | 513 | 0.80 | 250 | 0.70 |
| 8640 | 8684 | 8662 | Pub8662 | 513 | 0.80 | 250 | 0.71 |
| 8710 | 8758 | 8734 | Pub8734 | 513 | 0.74 | 250 | 0.67 |
| 8771 | 8781 | 8776 | Pub8776 | 513 | 0.56 | 250 | 0.59 |
| 8913 | 8947 | 8930 | Pub8930 | 513 | 0.68 | 250 | 0.64 |
| 8961 | 8977 | 8969 | Pub8969 | 513 | 0.65 | 250 | 0.57 |
| 9122 | 9162 | 9142 | Pub9142 | 513 | 0.66 | 250 | 0.66 |
| 9199 | 9233 | 9216 | Pub9216 | 513 | 0.59 | 250 | 0.62 |
| 9311 | 9323 | 9317 | Pub9317 | 513 | 0.57 | 250 | 0.60 |
| 9357 | 9370 | 9364 | Pub9363 | 513 | 0.58 | 250 | 0.63 |
| 9409 | 9458 | 9434 | Pub9433 | 513 | 0.67 | 250 | 0.65 |
| 9478 | 9512 | 9495 | Pub9495 | 513 | 0.61 | 250 | 0.63 |
| 9629 | 9667 | 9648 | Pub9648 | 513 | 0.62 | 250 | 0.64 |
| 9696 | 9749 | 9722 | Pub9722 | 513 | 0.70 | 250 | 0.67 |
| 9977 | 10281 | 10129 | pub10128 | 513 | 0.66 | 236 | 0.48 |
| 10291 | 10346 | 10318 | pub10318 | 513 | 0.66 | 236 | 0.56 |
| 10692 | 10826 | 10759 | pub10759 | 513 | 0.62 | 236 | 0.51 |
| 10867 | 11265 | 11066 | pub11066 | 513 | 0.61 | 236 | 0.55 |
| 11339 | 11856 | 11597 | pub11597 | 513 | 0.75 | 236 | 0.77 |
| 12080 | 12121 | 12100 | pub12100 | 513 | 0.63 | 236 | 0.54 |
| 12159 | 12228 | 12194 | pub12193 | 513 | 0.59 | 236 | 0.49 |
| 12422 | 12582 | 12502 | pub12501 | 513 | 0.66 | 236 | 0.64 |
| 12620 | 12814 | 12717 | pub12717 | 513 | 0.73 | 236 | 0.60 |
| 12839 | 12854 | 12846 | pub12846 | 513 | 0.72 | 236 | 0.56 |
| 13135 | 13230 | 13182 | pub13182 | 513 | 0.69 | 250 | 0.53 |
| 13386 | 13438 | 13412 | pub13412 | 513 | 0.54 | 250 | 0.56 |
| 13539 | 13604 | 13572 | pub13571 | 513 | 0.71 | 250 | 0.64 |
| 14402 | 14459 | 14430 | pub14430 | 513 | 0.74 | 250 | 0.67 |
| 15247 | 15321 | 15284 | pub15284 | 513 | 0.69 | 250 | 0.60 |
| 15414 | 15785 | 15600 | pub15599 | 513 | 0.76 | 250 | 0.71 |
| 15872 | 15919 | 15896 | pub15895 | 513 | 0.58 | 250 | 0.57 |
| 16366 | 16487 | 16427 | pub16426 | 513 | 0.66 | 250 | 0.60 |
| 16682 | 16862 | 16772 | pub16771 | 513 | 0.69 | 250 | 0.61 |
| 16984 | 17260 | 17122 | pub17121 | 513 | 0.68 | 250 | 0.60 |
| 17288 | 17389 | 17339 | pub17338 | 513 | 0.81 | 250 | 0.72 |
| 17431 | 18285 | 17858 | pub17858 | 513 | 0.81 | 250 | 0.68 |
| 18321 | 18523 | 18422 | pub18422 | 513 | 0.73 | 250 | 0.59 |
| 18728 | 18804 | 18766 | pub18766 | 513 | 0.65 | 250 | 0.52 |
| 18921 | 19052 | 18987 | pub18986 | 513 | 0.69 | 250 | 0.55 |

H. Identification of families of ROIs: JMP™ statistical package (SAS Institute Inc., Cary, N.C.) program's multivariate analysis function was used to identify ROIs that were highly correlated. A two-dimensional correlation coefficient matrix was extracted from JMP program and further analyzed by Microsoft Excel. For every ROI, a set of ROIs for which the correlation coefficient exceeded 0.8 was identified. These ROIs together become a family of correlated ROIs. Table 15 shows the correlating families, their corresponding member ROIs, the AUC value for the member ROIs in the large cohort, and the average of the correlation coefficients to the other members of the family. Thus, it can be seen that the ROIs having masses of 3449 and 3494 are highly correlated and can be substituted for each other within the context of the present invention.

TABLE 15

Families of correlated Regions of Interest.

| ROI name | Members | AUCs | Corr Coeff |
|---|---|---|---|
| Group A (n = 2) | | | |
| Pub3448 | 3449 | 0.72 | 0.81 |
| Pub3493 | 3494 | 0.72 | 0.81 |
| Group B (n = 2) | | | |
| Pub4487 | 4488 | 0.75 | 0.8 |
| Pub4682 | 4682 | 0.72 | 0.8 |
| Group C (n = 9) | | | |
| Pub8776 | 8776 | 0.56 | 0.8 |
| Pub8930 | 8930 | 0.68 | 0.83 |
| Pub9142 | 9142 | 0.66 | 0.92 |
| Pub9216 | 9216 | 0.59 | 0.91 |
| Pub9363 | 9363 | 0.58 | 0.88 |
| Pub9433 | 9434 | 0.67 | 0.94 |
| Pub9495 | 9495 | 0.61 | 0.94 |
| Pub9648 | 9648 | 0.62 | 0.93 |
| Pub9722 | 9722 | 0.7 | 0.89 |
| Group D (n = 15) | | | |
| Pub5036 | 5036 | 0.65 | 0.71 |
| Pub5139 | 5139 | 0.61 | 0.81 |
| Pub5264 | 5265 | 0.59 | 0.79 |
| Pub5357 | 5357 | 0.64 | 0.85 |
| Pub5483 | 5484 | 0.62 | 0.87 |
| Pub5573 | 5573 | 0.59 | 0.8 |
| Pub5593 | 5593 | 0.6 | 0.78 |
| Pub5615 | 5615 | 0.55 | 0.77 |
| Pub6702 | 6702 | 0.57 | 0.79 |
| Pub6718 | 6718 | 0.64 | 0.73 |
| Pub10759 | 10759 | 0.62 | 0.77 |
| Pub11066 | 11066 | 0.61 | 0.84 |
| Pub12193 | 12194 | 0.59 | 0.79 |
| Pub13412 | 13412 | 0.54 | 0.78 |
| acn10679 | acn10679 | 0.61 | 0.73 |
| acn10877 | acn10877 | 0.62 | 0.77 |
| Group E (n = 6) | | | |
| Pub6391 | 6392 | 0.65 | 0.9 |
| Pub6533 | 6534 | 0.63 | 0.9 |
| Pub6587 | 6587 | 0.6 | 0.87 |
| Pub6798 | 6799 | 0.76 | 0.85 |
| Pub9317 | 9317 | 0.57 | 0.7 |
| Pub13571 | 13571 | 0.71 | 0.67 |
| Group F (n = 8) | | | |
| Pub7218 | 7219 | 0.73 | 0.82 |
| Pub7255 | 7255 | 0.72 | 0.73 |
| Pub7317 | 7318 | 0.71 | 0.88 |
| Pub7413 | 7414 | 0.73 | 0.81 |
| Pub7499 | 7499 | 0.76 | 0.84 |
| Pub7711 | 7711 | 0.72 | 0.76 |
| Pub14430 | 14430 | 0.74 | 0.77 |
| Pub15599 | 15600 | 0.76 | 0.82 |
| Group G (n = 7) | | | |
| Pub8496 | 8496 | 0.69 | 0.78 |
| Pub8546 | 8547 | 0.73 | 0.88 |
| Pub8606 | 8606 | 0.8 | 0.84 |
| Pub8662 | 8662 | 0.79 | 0.77 |
| Pub8734 | 8734 | 0.74 | 0.45 |
| Pub17121 | 17122 | 0.68 | 0.78 |
| Pub17338 | 17339 | 0.81 | 0.54 |
| Group H (n = 3) | | | |
| Pub6249 | 6249 | 0.66 | 0.82 |
| Pub12501 | 12502 | 0.66 | 0.87 |
| Pub12717 | 12717 | 0.73 | 0.87 |
| Group I (n = 5) | | | |
| Pub5662 | 5662 | 0.73 | 0.93 |
| Pub5777 | 5777 | 0.71 | 0.92 |
| Pub5898 | 5898 | 0.63 | 0.89 |
| Pub11597 | 11597 | 0.75 | 0.93 |
| acn11559 | acn11559 | 0.63 | 0.84 |
| Group J (n = 5) | | | |
| Pub7775 | 7775 | 0.63 | 0.39 |
| Pub7944 | 7944 | 0.64 | 0.83 |
| Pub7980 | 7980 | 0.62 | 0.72 |
| Pub8002 | 8002 | 0.58 | 0.77 |
| Pub15895 | 15895 | 0.58 | 0.75 |
| Group K (n = 4) | | | |
| Pub17858 | 17858 | 0.81 | 0.84 |
| Pub18422 | 18422 | 0.73 | 0.92 |
| Pub18766 | 18766 | 0.69 | 0.89 |
| Pub18986 | 18986 | 0.65 | 0.91 |
| Group L (n = 12) | | | |
| Pub3018 | 3018 | 0.5 | 0.78 |
| Pub3640 | 3640 | 0.62 | 0.82 |
| Pub3658 | 3658 | 0.51 | 0.81 |
| Pub3682 | 3682 | 0.72 | 0.77 |
| Pub3705 | 3705 | 0.57 | 0.79 |
| Pub3839 | 3839 | 0.62 | 0.75 |
| hic2451 | hic2451 | 0.6 | 0.78 |
| hic2646 | hic2646 | 0.54 | 0.7 |
| hic3035 | hic3035 | 0.54 | 0.72 |
| tfa3016 | tfa3016 | 0.63 | 0.78 |
| tfa3635 | tfa3635 | 0.61 | 0.78 |
| tfa4321 | tfa4321 | 0.61 | 0.74 |
| Group M (n = 2) | | | |
| Pub2331 | 2331 | 0.65 | 0.9 |
| tfa2331 | tfa2331 | 0.66 | 0.9 |
| Group N (n = 2) | | | |
| Pub4557 | 4557 | 0.73 | 0.81 |
| Pub4592 | 4592 | 0.71 | 0.81 |
| Group O (n = 6) | | | |
| acn4631 | acn4631 | 0.74 | 0.81 |
| acn5082 | acn5082 | 0.68 | 0.85 |
| acn5262 | acn5262 | 0.68 | 0.9 |
| acn5355 | acn5355 | 0.64 | 0.87 |
| acn5449 | acn5449 | 0.7 | 0.88 |
| acn5455 | acn5455 | 0.68 | 0.88 |
| Group P (n = 6) | | | |
| acn6399 | acn6399 | 0.67 | 0.78 |
| acn6592 | acn6592 | 0.68 | 0.8 |
| acn8871 | acn8871 | 0.69 | 0.79 |
| acn9080 | acn9080 | 0.65 | 0.84 |
| acn9371 | acn9371 | 0.65 | 0.83 |
| acn9662 | acn9662 | 0.66 | 0.79 |
| Group Q (n = 2) | | | |
| acn9459 | acn9459 | 0.66 | 0.91 |
| acn9471 | acn9471 | 0.7 | 0.91 |
| Group R (n = 4) | | | |
| hic2506 | hic2506 | 0.65 | 0.82 |
| hic2980 | hic2980 | 0.64 | 0.87 |
| hic3176 | hic3176 | 0.69 | 0.8 |
| tfa2984 | tfa2984 | 0.69 | 0.78 |
| Group S (n = 2) | | | |
| hic2728 | hic2728 | 0.61 | 0.81 |
| hic3276 | hic3276 | 0.64 | 0.81 |
| Group T (n = 6) | | | |
| hic6381 | hic6381 | 0.7 | 0.83 |
| hic6387 | hic6387 | 0.71 | 0.84 |
| hic6450 | hic6450 | 0.66 | 0.81 |
| hic6649 | hic6649 | 0.62 | 0.73 |
| hic6816 | hic6816 | 0.72 | 0.81 |
| hic6823 | hic6823 | 0.71 | 0.79 |

TABLE 15-continued

Families of correlated Regions of Interest.

| ROI name | Members | AUCs | Corr Coeff |
|---|---|---|---|
| Group U (n = 2) | | | |
| hic8791 | hic8791 | 0.58 | 0.8 |
| hic8897 | hic8897 | 0.61 | 0.8 |
| Group V (n = 2) | | | |
| tfa6453 | tfa6453 | 0.74 | 0.84 |
| tfa6652 | tfa6652 | 0.72 | 0.84 |
| Group W (n = 2) | | | |
| hic6005 | hic6005 | 0.69 | 0.74 |
| hic5376 | hic5376 | 0.68 | 0.74 |
| Group X (n = 3) | | | |
| Pub4713 | 4714 | 0.73 | 0.83 |
| Pub4750 | 4751 | 0.76 | 0.66 |
| Pub4861 | 4861 | 0.72 | 0.65 |

Example 6

Multivariate Analysis of Biomarkers Using Discriminant Analysis, Decision Tree Analysis and Principal Component Analysis Multivariate analyses were carried out on the immunoassay biomarkers and the Regions of Interest. All the different analyses were carried out using the JMP statistical package.

For simplicity purposes, discriminant analysis (DA), principal component analysis (PCA) and decision tree (DT) are generally referred to herein as multivariate methods (MVM). It is noteworthy to mention that in PCA, only the first 15 principal components, which account for more than 90% of the total variability in the data, were extracted. Factor loadings and/or communalities were used to extract only the one factor (biomarker) that contributed the most to each principal component. Since the square of the factor loadings reflect the relative contribution of each factor in each principal component, these values were used as a basis for selecting the marker that contributed the most to each principal component. Thus, 15 factors (biomarkers) contributing the most to the first 15 principal components were extracted. In DA, the process of selecting markers was carried out until the addition of more markers had no effect on the classification outcome. In general, DA used between 5 and 8 biomarkers. In the case of DTs, 6-node trees with about 5 biomarkers were constructed and evaluated.

The biomarkers were evaluated by using the well-established bootstrapping and leave-one-out validation methods (Richard O. Duda et al. *In Pattern Classification, 2$^{nd}$ Edition*, pp. 485, Wiley-Interscience (2000)). A ten-fold training process was used to identify the robust biomarkers that show up regularly. Robust biomarkers were defined as those markers that emerged in at least 50% of the training sets. Thus, biomarkers with a frequency greater than or equal to 5 in our ten-fold training process were selected for further evaluation. Table 16 below summarizes the biomarkers that showed up regularly in each method in each cohort.

The approach to biomarker discovery using various statistical methods offers a distinct advantage by providing a wider repertoire of candidate biomarkers (FIG. 1). While some methods such as DA and PCA work well with normally distributed data, other non-parametric methods such as logistic regression and decision trees perform better with data that are discrete, not uniformly distributed or have extreme variations. Such an approach is ideal when markers (such as biomarkers and biometric parameters) from diverse sources (mass spectrometry, immunoassay, clinical history, etc.) are to be combined in a single panel since the markers may or may not be normally distributed in the population.

TABLE 16

Markers identified using multivariate analysis (MVM). Only the markers that show up at least 50% of the time were selected for further consideration.

| | | | small cohort | | | | | large cohort | | |
|---|---|---|---|---|---|---|---|---|---|---|
| | AUC | Top Markers | DA | PCA | DT | | AUC | Top Markers | DA | PCA | DT |
| 1 | 0.76 | acn9459 | x | | | 1 | 0.81 | pub17858 | x | | x |
| 2 | 0.75 | pub4861 | x | | x | 2 | 0.81 | pub17338 | | | x |
| 3 | 0.66 | CEA | | | x | 3 | 0.8 | pub8606 | x | | |
| 4 | 0.65 | pub9433 | | x | | 4 | 0.72 | pub4861 | x | | x |
| 5 | 0.64 | pub9648 | | | x | 5 | 0.69 | pub3743 | x | | x |
| 6 | 0.64 | pub2951 | x | | | 6 | 0.67 | acn6399 | | x | |
| 7 | 0.63 | pub6052 | x | | | 7 | 0.66 | tfa2331 | | x | |
| 8 | 0.6 | tfa2759 | x | | | 8 | 0.65 | pub9433 | | x | |
| 9 | 0.6 | tfa9133 | x | | | 9 | 0.58 | acn6592 | | x | |
| 10 | 0.59 | acn4132 | | x | | 10 | 0.56 | pub4213 | | x | |
| 11 | 0.58 | acn6592 | | x | | 11 | 0.55 | acn9371 | | x | |
| 12 | 0.57 | pub7775 | | x | | | | Total | 4 | 6 | 4 |
| 13 | 0.56 | pub4213 | | x | | | | | | | |
| 14 | 0.55 | acn9371 | | x | | | | | | | |
| | | Total | 6 | 6 | 3 | | | | | | |

In the above Table, there is no difference between "x" and "X".

Example 7

Split and Score Method (Hereinafter "SSM")

A. Improved Split and Score Method (SSM)

Interactive software implementing the split point (cutoff) scoring method described by Mor et al. (See, *PNAS,* 102(21): 7677 (2005)) has been written to run under Microsoft® Windows. This software reads Microsoft® Excel spreadsheets that are natural vehicles for storing the results of marker (biomarkers and biometric parameters) analysis for a set of samples. The data can be stored on a single worksheet with a field to designate the disease of the sample, stored on two worksheets, one for diseased samples and the other for non-diseased samples, or on four worksheets, one pair for training samples, diseased and non-diseased, and the other pair for testing samples, diseased and non-diseased. In the first two cases, the user may use the software to automatically generate randomly selected training and testing pairs from the input. In the final case, multiple Excel files may be read at once and analyzed in a single execution.

The software presents a list of all the markers collected on the data. The user selects a set of markers from this list to be used in the analysis. The software automatically calculates split points (cutoffs) for each marker from the diseased and non-diseased training datasets as well as determining whether the diseased group is elevated or decreased relative to non-diseased. The split point (cutoff) is chosen to maximize the accuracy of each single marker. Cutoffs (or split points) may also be set and adjusted manually.

In all analyses, the accuracy, specificity, and sensitivity at each possible threshold value using the selected set of markers are calculated for both the training and test sets. In analyses that produce multiple results these results are ordered by the training set accuracies.

Three modes of analyses are available. The simplest mode calculates the standard results using only the selected markers. A second mode determines the least valuable marker in the selected list. Multiple calculations are performed, one for each possible subset of markers formed by removing a single marker. The subset with the greatest accuracy suggests that the marker removed to create the subset makes the least contribution in the entire set. Results for these first two modes are essentially immediate. The most involved calculation explores all possible combination of selected markers. The twenty best outcomes are reported. This final option can involve a large number of candidates. Thus, it is quite computationally intensive and may take sometime to complete. Each additional marker used doubles the run time.

For approximately 20 markers, it has often been found that there are usually 6 to 10 markers that appear in all of the 20 best results. These then are matched with 2 to 4 other markers from the set. This suggests that there might be some flexibility in selecting markers for a diagnostic panel. The top twenty best outcomes are generally similar in accuracy but may differ significantly in sensitivity and specificity. Looking at all possible combinations of markers in this manner provides an insight into combinations that might be the most useful clinically.

B. Weighted Scoring Method

As discussed previously herein, this method is a weighted scoring method that involves converting the measurement of one marker into one of many potential scores. Those scores are derived using the equation:

Score=AUC*factor/(1−specificity)

The marker Cytokeratin 19 can be used as an illustrative example. Cytokeratin 19 levels range from 0.4 to 89.2 ng/mL in the small cohort. Using the Analyze-it software, a ROC curve was generated with the Cytokeratin 19 data such that cancers were positive. The false positive rate (1-specificity) was plotted on the x-axis and the true positive rate (sensitivity) was plotted on the y-axis and a spreadsheet with the Cytokeratin 19 value corresponding to each point on the curve was generated. At a cutoff of 3.3 ng/mL, the specificity was 90% and the false positive rate was 10%. A factor of three was arbitrarily given for this marker since its AUC was greater than 0.7 and less than 0.8 (See, Table 2). However, any integral number can be used as a factor. In this case, increasing numbers are used with biomarkers having higher AUC indicating better clinical performance. The score for an individual with a Cytokeratin 19 value greater than or equal to 3.3 ng/mL was thus calculated.

Score=AUC*factor/(1−specificity)

Score=0.70*3/(1−0.90)

Score=21

For any value of Cytokeratin 19 greater than 3.3 ng/mL, a score of 21 was thus given. For any value of Cytokeratin 19 greater than 1.9 but less than 3.3, a score of 8.4 was given and so on (See Table 17a, below).

TABLE 17a

The 4 possible scores given for Cytokeratin 19.

| | CYTOKERATIN 19 | |
| --- | --- | --- |
| | AUC | 0.70 |
| cutoff | Specificity | Score |
| 3.3 | 0.90 | 21 |
| 1.9 | 0.75 | 8.4 |
| 1.2 | 0.50 | 4.2 |
| 0 | 0 | 0.0 |

The score increases in value as the specificity level increases. The chosen values of specificity can be tailored to any one marker. The number of specificity levels chosen for any one marker can be tailored. This method allows specificity to improve the contribution of a biomarker to a panel.

A comparison of the weighted scoring method was made to the binary scoring method described in Example 7A above. In this example, the panel constituted eight immunoassay biomarkers: CEA, Cytokeratin 19, Cytokeratin 18, CA125, CA15-3, CA19-9, proGRP, and SCC. The AUCs, factors, specificity levels chosen, and scores at each of these specificity levels are tabulated for each of the markers below in Table 17b. Using these individual cutoffs and scores, each sample was tabulated for the eight biomarkers. The total score for each sample was summed and plotted in a ROC curve. This ROC curve was compared to the ROC curves generated using the binary scoring method with either the small cohort cutoffs (split points)) or the large cohort cutoffs (split points) provided in Table 18 (See, Example 8A). The AUC values for the weighted scoring method, the binary scoring method large cohort cutoffs (split points), and the binary scoring method small cohort cutoffs (split points) were 0.78, 0.76, and 0.73 respectively. Aside from the improved overall performance of the panel as indicated by the AUC value, the weighted scoring method provides a larger number of possible score values for the panel. One advantage of the larger number of possible panel scores is there are more options to set the cutoff for a positive test (See, FIG. 5). The binary scoring method applied to an 8 biomarker panel can have as a panel output values ranging from 0 to 8 with increments of 1 (See, FIG. 5).

TABLE 17b

|  | CEA | CK-18 | proGRP | CA15-3 | CA125 | SCC | CK-19 | CA19-9 |
|---|---|---|---|---|---|---|---|---|
| AUC | 0.67 | 0.65 | 0.62 | 0.58 | 0.67 | 0.62 | 0.7 | 0.55 |
| Factor | 2 | 2 | 2 | 1 | 2 | 2 | 3 | 1 |
| value @ 50% specificity* | 2.02 | 47.7 | 11.3 | 16.9 | 15.5 | 0.93 | 1.2 | 10.6 |
| value @ 75% specificity* | 3.3 | 92.3 | 18.9 | 21.8 | 27 | 1.3 | 1.9 | 21.9 |
| value @ 90% specificity* | 4.89 | 143.3 | 28.5 | 30.5 | 38.1 | 1.98 | 3.3 | 45.8 |
| score below 50% specificity | 0 | 0 | 0 | 0 | 0 | 0 | 0 | 0 |
| score above 50% specificity | 2.68 | 2.6 | 2.48 | 1.16 | 2.68 | 2.48 | 4.2 | 1.1 |
| score above 75% specificity | 5.36 | 5.2 | 4.96 | 2.32 | 5.36 | 4.96 | 8.4 | 2.2 |
| score above 90% specificity | 13.4 | 13 | 12.4 | 5.8 | 13.4 | 12.4 | 21 | 5.5 |

*Each of these values represents a cutoff (split point).

The patent application entitled "Weighted Scoring Methods and Use Thereof In Screening", filed electronically on Jun. 29, 2007 as U.S. Patent Application No. 11/772,041, describes among other things, the Weighted Scoring Method and is incorporated herein by reference in its entirety for its teachings regarding same.

Example 8

Predictive Models for Lung Cancer Using the Split & Score Method (SSM)

A. SSM of Immunoassay Biomarkers

As discussed in Example 2, some biomarkers were detected by immunological assays. These included Cytokeratin 19, CEA, CA125, SCC, proGRP, Cytokeratin 18, CA19-9, and CA15-3. These data were evaluated using the SSM. These biomarkers together exhibited limited clinical utility. In the small cohort, representing the benign lung disease and lung cancer, the accuracy of the 8 biomarker panel with a threshold of 4 or higher as a positive result, achieved an average of 64.8% accuracy (AUC 0.69) across the 10 small cohort test sets. In the large cohort, representing normals as well as benign lung disease and lung cancer, the accuracy of the 8 biomarker panel with a threshold of 4 or higher as a positive result, achieved an average of 77.4% (AUC 0.79) across the 10 large cohort test sets.

Including the biometric parameter of pack-years improved the predictive accuracy of these biomarkers by almost 5%. Thus, the accuracy of the 8 biomarker and 1 biometric parameter panel with a threshold of 4 or higher as a positive result, achieved an average of 69.6% (AUC 0.75) across the 10 small cohort test sets.

TABLE 18

Split Points (Cutoffs) calculated for each individual Immunoassay marker using the SSM algorithm.

|  | small cohort | | large cohort | | |
|---|---|---|---|---|---|
|  | avg split point (predetermined cutoff) | Stdev | avg split point (predetermined cutoff) | stdev | control group |
| CEA | 4.82 | 0 | 9.2 | 0 | norm <= split point |
| CK 19 | 1.89 | 0.45 | 2.9 | 0.3 | norm <= split point |
| CA125 | 13.65 | 8.96 | 26 | 2.6 | norm <= split point |
| CA15-3 | 13.07 | 3.39 | 20.1 | 2.6 | norm <= split point |
| CA19-9 | 10.81 | 11.25 | 41.1 | 18.5 | norm <= split point |
| SCC | 0.92 | 0.11 | 1.1 | 0.1 | norm <= split point |
| proGRP | 14.62 | 8.53 | 17.6 | 0 | norm <= split point |
| CK-18 | 57.37 | 2.24 | 67.2 | 9.5 | norm <= split point |
| parainfluenza | 103.53 | 32.64 | 79.2 | 9.8 | norm >= split point |
| Pack-yr | 30 |  | 30 |  | Norm <= split point |

B. SSM of Biomarkers and Biometric Parameters Selected by ROC/AUC

In contrast to Example 6, where putative biomarkers were identified using multivariate statistical methods, a simple, non-parametric method which involved ROC/AUC analysis was used in this case to identify putative biomarkers. By applying this method, individual markers with acceptable clinical performance (AUC>0.6) were chosen for further analysis. Only the top 15 biomarkers and the biometric parameter (pack years) were selected and the groups will be referred to as the 16AUC groups (small and large) hereinafter. These markers are listed in Table 19 below.

TABLE 19

Top 15 biomarkers and a biometric parameter (pack years)

| large cohort | | | small cohort | | |
|---|---|---|---|---|---|
| Marker | #obs | AUC | Marker | #obs | AUC |
| pub17338 | 513 | 0.813 | pub11597 | 236 | 0.766 |
| pub17858 | 513 | 0.812 | acn9459 | 244 | 0.761 |
| pub8606 | 513 | 0.798 | pub4861 | 250 | 0.75 |
| pub8662 | 513 | 0.796 | pack-yr | 257 | 0.739 |
| pub4628 | 513 | 0.773 | pub4750 | 250 | 0.729 |
| pub6798 | 513 | 0.765 | pub7499 | 250 | 0.725 |
| pub7499 | 513 | 0.762 | pub2433 | 250 | 0.719 |
| pub4750 | 513 | 0.76 | CK 19 | 248 | 0.718 |
| pub15599 | 513 | 0.757 | pub4789 | 250 | 0.718 |
| pub11597 | 513 | 0.751 | pub17338 | 250 | 0.718 |
| pub4487 | 513 | 0.747 | pub8662 | 250 | 0.713 |
| tfa6453 | 538 | 0.744 | acn9471 | 244 | 0.712 |
| pack years | 249 | 0.741 | pub15599 | 250 | 0.711 |
| pub8734 | 513 | 0.741 | tfa6652 | 236 | 0.71 |
| pub14430 | 513 | 0.741 | pub8606 | 250 | 0.703 |
| hic3959 | 529 | 0.741 | acn6681 | 244 | 0.703 |

Optimized combinations (panels) of the 16AUC small cohort markers were determined using the SSM on each of the 10 training subsets. This process was done both in the absence (Table 20a) and presence (Table 20b) of the biometric parameter smoking history (pack years) using the SSM. Thus, 15 biomarkers (excluding the biometric parameter pack-yr) or 15 biomarkers and the 1 biometric parameter (pack years) (the 16 AUC) were input variables for the split and score method. The optimal panel for each of the 10 training sets was determined based on overall accuracy. Each panel was tested against the remaining, untested samples and the performance statistics were recorded. The 10 panels were then compared and the frequency of each biomarker was noted. The process was performed twice, including and excluding the biometric pack year. The results of these two processes are presented in Tables 20a and 20b, below. Once again, robust markers with a frequency greater than or equal to 5 were selected for further consideration. The process was repeated for the large cohort and the results are presented in Table 20c. Tables 20a and 20b contain a partial list of the SSM results of the small cohort showing the frequency of the markers for a) the 15AUC biomarkers only and b) the 15AUC biomarkers and the biometric parameter pack yrs. Note that in the first table (20a) only 5 markers have frequencies greater than or equal to 5. In Table 20b, 7 markers fit that criterion. Table 20c contains a partial list of the SSM results of the large cohort showing the frequency of the markers for the 15AUC markers. Note that 11 markers have frequencies greater than or equal to 5.

TABLE 20a

| Train Set # | CK 19 | pub4789 | acn9459 | Pub11597 | tfa6652 | pub2433 | pub4713 |
|---|---|---|---|---|---|---|---|
| 1 | x | x | x | x | | | |
| 2 | x | x | x | x | | | x |
| 3 | x | x | x | | x | | |
| 4 | x | x | | x | | x | |
| 5 | x | x | x | | x | | |
| 6 | x | x | x | | x | | |
| 7 | x | x | x | x | | | x |
| 8 | x | x | x | x | x | x | |
| 9 | x | x | x | | x | | x |
| 10 | x | x | x | x | | x | |
| Frequency | 10 | 10 | 9 | 6 | 5 | 3 | 3 |

TABLE 20b

| Train Set # | acn 9459 | CK 19 | pkyrs | Pub 11597 | pub 4789 | pub 2433 | pub 4861 | tfa 6652 | acn 9471 |
|---|---|---|---|---|---|---|---|---|---|
| 1 | x | x | x | | | x | x | | |
| 2 | x | x | x | x | x | x | | | |
| 3 | x | x | x | x | x | | | x | |
| 4 | x | x | x | x | x | x | | x | x |
| 5 | x | x | x | x | | | x | x | |
| 6 | x | | x | | x | | | | x |
| 7 | x | x | x | x | x | x | x | | |
| 8 | x | x | x | | | x | | x | x |
| 9 | x | x | x | x | | | | x | |
| 10 | x | x | | x | x | x | | | x |
| Frequency | 10 | 9 | 9 | 8 | 7 | 5 | 5 | 4 | 4 |

TABLE 20c

| Train Set # | pub 11597 | pub 4487 | pub 17338 | pub 8606 | Pub 6798 | Tfa 6453 | pub 4750 | hic 3959 | pub 8662 | pub 4628 | pub 17858 |
|---|---|---|---|---|---|---|---|---|---|---|---|
| 1 | x | x | x | x | x | x |  | x |  |  |  |
| 2 | x | x | x | x | x | x | x | x | x |  |  |
| 3 | x | x | x | x |  |  | x | x | x |  | x |
| 4 | x |  | x |  | x | x |  | x |  |  |  |
| 5 | x | x | x | x |  |  | x | x |  | x | x |
| 6 | x | x |  | x | x | x | x | x | x |  |  |
| 7 | x | x |  |  | x | x | x | x | x | x | x |
| 8 | x | x | x |  | x |  |  |  | x | x |  |
| 9 | x | x |  | x |  |  | x |  |  | x | x |
| 10 | x | x | x | x | x | x | x | x |  | x | x |
| Frequency | 10 | 9 | 7 | 7 | 7 | 7 | 7 | 7 | 6 | 6 | 5 |

C. SSM of Biomarkers Selected by MVM

An example of one multi-variate method is decision tree analysis. Biomarkers identified using decision tree analysis alone were taken together and used in SSM. This group of biomarkers demonstrated similar clinical utility to that group of biomarkers designated as 16AUC. As an example, testing set 1 (of 10) has AUC of 0.90 (testing) without the biometric parameter pack years, and 0.91 (testing) with the biometric parameter pack years.

The DT biomarkers were combined with biomarkers identified using PCA and DA to generate the MVM group. The 14MVM group was evaluated with and without the biometric parameter smoking history (pack years) using the SSM. Once again, robust markers with a frequency greater than or equal to 5 were selected for further consideration (results not shown). As can be seen in the tables above, pack years (smoking history) has an effect on the number and type of biomarkers that emerge as robust markers. This is not totally unexpected since some biomarkers may have synergistic or deleterious effects on other biomarkers. One aspect of this invention involves finding those markers that work together as a panel in improving the predictive capability of the model. Along a similar vein, those biomarkers that were identified to work synergistically with the biometric parameter pack years in both methods (AUC and MVM) were combined in an effort to identify a superior panel of markers (See, Example 8D).

The multivariate markers identified for the large cohort were evaluated with the SSM. Once again, only those markers with frequencies greater than or equal to 5 were selected for further consideration. Table 21 below summarizes the SSM results for the large cohort.

TABLE 21

Partial list of the SSM results of the large cohort showing the frequency of the markers for the 11MVM markers. Note that 7 markers have frequencies greater than or equal to 5.

| Train Set # | pub 3743 | pub 4861 | pub 8606 | Pub 17338 | pub 17858 | acn 6399 | tfa 2331 |
|---|---|---|---|---|---|---|---|
| 1 | x | x | x | x | x | x |  |
| 2 | x | x | x | x | x |  | x |
| 3 | x | x | x | x |  | x |  |
| 4 | x | x |  | x | x | x |  |
| 5 | x | x | x | x |  |  | x |
| 6 | x | x | x |  | x | x |  |
| 7 | x | x | x | x | x | x | x |
| 8 | x | x | x | x |  |  |  |
| 9 | x | x | x | x |  | x | x |
| 10 | x |  | x | x | x |  | x |
| Frequency | 10 | 9 | 9 | 8 | 6 | 6 | 5 |

D. SSM of Combined Markers (AUC+MVM+Pack Years)

In a subsequent step, all the markers (biomarkers and biometric parameters) with frequencies greater than or equal to 5 (in the 10 training sets) were combined to produce a second list of markers containing markers from both the AUC and MVM groups for both cohorts. From the SSM results, 16 unique markers from the small cohort and 15 unique markers from the large cohort with frequencies greater than or equal to five were selected. Table 22 below summarizes the markers that were selected.

TABLE 22

Combined markers from both AUC and MVM groups.

| | small cohort | | | | large cohort | | |
|---|---|---|---|---|---|---|---|
| | AUC Markers | 16AUC | 14MVM | | AUC Markers | 15AUC | 11MVM |
| 1 | 0.77 Pub11597 | x | | 1 | 0.813 Pub17338 | x | x |
| 2 | 0.76 Acn9459 | x | x | 2 | 0.812 pub17858 | x | x |

TABLE 22-continued

Combined markers from both AUC and MVM groups.

| small cohort | | | | | large cohort | | | |
|---|---|---|---|---|---|---|---|---|
| | AUC | Markers | 16AUC | 14MVM | | AUC | Markers | 15AUC | 11MVM |
| 3 | 0.75 | Pub4861 | x | x | 3 | 0.798 | pub8606 | x | x |
| 4 | 0.74 | pkyrs | x | x | 4 | 0.796 | pub8662 | x | |
| 5 | 0.72 | Pub2433 | x | | 5 | 0.773 | pub4628 | x | |
| 6 | 0.72 | CK 19 | x | | 6 | 0.765 | pub6798 | x | |
| 7 | 0.72 | Pub4789 | x | | 7 | 0.76 | pub4750 | x | |
| 8 | 0.71 | Tfa6652 | x | | 8 | 0.751 | pub11597 | x | |
| 9 | 0.66 | cea | | x | 9 | 0.747 | pub4487 | x | |
| 10 | 0.64 | Pub2951 | | x | 10 | 0.744 | tfa6453 | x | |
| 11 | 0.63 | Pub6052 | | x | 11 | 0.741 | hic3959 | x | |
| 12 | 0.6 | Tfa2759 | | x | 12 | 0.72 | pub4861 | | x |
| 13 | 0.6 | Tfa9133 | | x | 13 | 0.69 | pub3743 | | x |
| 14 | 0.59 | Acn4132 | | x | 14 | 0.67 | acn6399 | | x |
| 15 | 0.58 | Acn6592 | | x | 15 | 0.66 | tfa2331 | | x |
| 16 | 0.57 | Pub7775 | | x | | | Total | 11 | 7 |
| | | Total | 8 | 11 | | | | | |

The above lists of markers were taken through a final evaluation cycle with the SSM. As previously stated, combinations of the markers were optimized for the 10 training subsets and the frequency of each biomarker and biometric parameter was determined. By applying the selection criterion that a marker be present in at least 50% of the training sets, 13 of the 16 markers for the small cohort were selected and 9 of the markers for the large cohort were selected.

TABLE 23a

List of markers with frequencies greater than or equal to 5.

| small cohort | | | | large cohort | | |
|---|---|---|---|---|---|---|
| | AUC | Markers | Frequency | | AUC | Markers | Frequency |
| 1 | 0.718 | CK 19 | 9 | 1 | 0.67 | acn6399 | 10 |
| 2 | 0.761 | acn9459 | 8 | 2 | 0.69 | pub3743 | 8 |
| 3 | 0.74 | pkyrs | 8 | 3 | 0.798 | pub8606 | 7 |
| 4 | 0.664 | cea | 8 | 4 | 0.751 | pub11597 | 7 |
| 5 | 0.603 | tfa2759 | 8 | 5 | 0.744 | tfa6453 | 7 |
| 6 | 0.766 | pub11597 | 7 | 6 | 0.747 | pub4487 | 6 |
| 7 | 0.718 | pub4789 | 7 | 7 | 0.72 | pub4861 | 6 |
| 8 | 0.6 | tfa9133 | 7 | 8 | 0.765 | pub6798 | 5 |
| 9 | 0.75 | pub4861 | 6 | 9 | 0.741 | hic3959 | 5 |
| 11 | 0.719 | pub2433 | 6 | | | | |
| 10 | 0.589 | acn4132 | 6 | | | | |
| 12 | 0.57 | Pub7775 | 6 | | | | |
| 13 | 0.635 | pub2951 | 5 | | | | |

For each marker, a split point (cutoff) was determined by evaluating each training dataset for the highest accuracy on classification as the level of marker was optimized. The split points (cutoffs) for the eight most frequent markers used in the small cohort are listed below.

TABLE 23b

| | Markers | Control Group | Ave | Stdev |
|---|---|---|---|---|
| 1 | CK 19 | Norm <= SP | 1.89 | 0.45 |
| 2 | acn9459 | Norm >= SP | 287.3 | 23.67 |
| 3 | pkyrs | Norm <= SP | 30.64 | 4.21 |
| 4 | cea | Norm <= SP | 4.82 | 0 |
| 5 | tfa2759 | Norm >= SP | 575.6 | 109.7 |
| 6 | pub11597 | Norm <= SP | 34.4 | 2.52 |
| 7 | pub4789 | Norm <= SP | 193.5 | 18.43 |
| 8 | tfa9133 | Norm >= SP | 203.6 | 46.38 |

Table 23b shows the list of the 8 most frequent markers with their average (Ave) split points (each a predetermined cutoff). Standard deviations for each split point (cutoff) are also included (Stdev). The position of the control group relative to the split point (cutoff) is given in the second column from the left. As an example, in Cytokeratin 19, the normal group or control group (non Cancer) is less than or equal to the split point (cutoff) value of 1.89.

Example 9

Validation of Predictive Models

Subsets of the list of 13 biomarkers and biometric parameters for the small cohort (See, Table 23a above) provide good clinical utility. For example, the 8 most frequent biomarkers and biometric parameters used together as a panel in the split and score method have an AUC of 0.90 for testing subset 1 (See, Table 23b above).

Predictive models comprising a 7-marker panel (markers 1-7, Table 23b) and an 8-marker panel (markers 1-8, Table 23b) were validated using 10 random test sets. Tables 24a and 24b below summarize the results for the two models. All conditions and calculation parameters were identical in both cases with the exception of the number of markers in each model.

TABLE 24a

| Test Set # | AUC | Accuracy (%) | Sensitivity (%) | Specificity (%) | # Of Markers | Threshold |
|---|---|---|---|---|---|---|
| 1 | 0.91 | 85 | 80.7 | 90.7 | 7 | 3 |
| 2 | 0.92 | 85 | 78.2 | 93.3 | 7 | 3 |
| 3 | 0.89 | 80 | 78.8 | 82.4 | 7 | 3 |
| 4 | 0.89 | 82 | 78.0 | 86.0 | 7 | 3 |
| 5 | 0.90 | 85 | 78.7 | 90.6 | 7 | 3 |
| 6 | 0.89 | 83 | 76.9 | 89.6 | 7 | 3 |
| 7 | 0.92 | 86 | 78.4 | 93.9 | 7 | 3 |
| 8 | 0.89 | 83 | 79.6 | 87.0 | 7 | 3 |
| 9 | 0.91 | 84 | 79.6 | 89.1 | 7 | 3 |
| 10 | 0.92 | 86 | 81.8 | 91.1 | 7 | 3 |
| Ave | 0.90 | 83.9 | 79.1 | 89.4 | | |
| Stdev | 0.01 | 1.9 | 1.4 | 3.5 | | |

Table 24a shows the clinical performance of the 7-marker panel with ten random test sets. The 7 markers and the average split points (cutoffs) used in the calculations were given in Table 16b. A threshold value of 3 was used for separating the diseased group from the non-diseased group. The average AUC for the model is 0.90, which corresponds to an average accuracy of 83.9% and sensitivity and specificity of 79.1% and 89.4% respectively.

TABLE 24b

| Test Set # | AUC | Accuracy (%) | Sensitivity (%) | Specificity (%) | # Of Markers | Threshold |
|---|---|---|---|---|---|---|
| 1 | 0.90 | 81 | 91.2 | 67.4 | 8 | 3 |
| 2 | 0.91 | 86 | 92.7 | 77.8 | 8 | 3 |
| 3 | 0.89 | 83 | 90.9 | 67.6 | 8 | 3 |
| 4 | 0.89 | 83 | 90.0 | 76.0 | 8 | 3 |
| 5 | 0.91 | 83 | 91.5 | 75.5 | 8 | 3 |
| 6 | 0.90 | 83 | 88.5 | 77.1 | 8 | 3 |
| 7 | 0.92 | 88 | 92.2 | 83.7 | 8 | 3 |
| 8 | 0.90 | 85 | 92.6 | 76.1 | 8 | 3 |
| 9 | 0.93 | 84 | 92.6 | 73.9 | 8 | 3 |
| 10 | 0.92 | 85 | 92.7 | 75.6 | 8 | 3 |
| Ave | 0.91 | 84.1 | 91.5 | 75.1 | | |
| Stdev | 0.01 | 1.8 | 1.4 | 4.7 | | |

Table 24b shows the clinical performance of the 8-marker panel with ten random test sets. The 8 markers and the average split points (cutoffs) used in the calculations were given in Table 16b. A threshold value of 3 (a predetermined total score) was used for separating the diseased group from the non-diseased group. The average AUC for the model is 0.91, which corresponds to an average accuracy of 84.1% and sensitivity and specificity of 91.5% and 71.5% respectively.

A comparison of Tables 24a and 24b shows that both models are comparable in terms of AUC and accuracy and differ only in sensitivity and specificity. As can be seen in Table 24a, the 7-marker panel shows greater specificity (89.4% vs. 75.1%). In contrast, the 8-marker panel shows better sensitivity (91.5% vs. 79.1%) as judged from their average values (Ave). It should be noted that the threshold (or predetermined total score) that maximized the accuracy of the classification was chosen, which is akin to maximizing the AUC of an ROC curve. Thus, the chosen threshold of 3 (a predetermined total score) not only maximized accuracy but also offered the best compromise between the sensitivity and specificity of the model. In practice, what this means is that a normal individual is considered to be at low "risk" of developing lung cancer if said individual tests positive for less than or equal to 3 out of the 7 possible markers in this model (or less than or equal to 3 out of 8 for the second model). Individuals with scores higher (a total score) than the set threshold (or predetermined total score) are considered to be at higher risk and become candidates for further testing or follow-up procedures. It should be noted that the threshold of the model (namely, the predetermined total score) can either be increased or decreased in order to maximize the sensitivity or the specificity of said model (at the expense of the accuracy). This flexibility is advantageous since it allows the model to be adjusted to address different diagnostic questions and/or populations at risk, e.g., differentiating normal individuals from symptomatic and/or asymptomatic individuals.

Various predictive models are summarized in Tables 25a and 25b below. For each predictive model, the biomarkers and biometric parameters that constitute the model are indicated, as is the threshold (namely, the predetermined total score), the average AUC, accuracy, sensitivity, and specificity with their corresponding standard deviations (enclosed in brackets) across the 10 test sets. The 8 marker panel outlined above is Mixed Model 2 and the 7 marker panel outlined above is Mixed Model 3. Mixed Model 1A and Mixed Model 1B contain the same markers. The only difference between Mixed Model 1A and Mixed Model 1B is in the threshold (namely, the predetermined total score). Likewise, Mixed Model 10A and Mixed Model 10B contain the same markers. The only difference between Mixed Model 10A and Mixed Model 10B is in the threshold (namely, the predetermined total score).

TABLE 25a

| | small cohort | | | | | | | | | | | |
|---|---|---|---|---|---|---|---|---|---|---|---|---|
| Markers | 8 IA model | 9 IA Model | IA-pkyrs Model | MS Model | MS pkyrs Model | Mixed Model 1A | Mixed Model 1B | Mixed Model 2 | Mixed Model 3 | Mixed Model 4 | Mixed Model 5 |
| CK 19 | x | x | x | | | x | x | x | x | | |
| CA 19-9 | x | x | x | | | | | | | | |
| CEA | x | x | x | | | x | x | x | x | x | x |
| CA15-3 | x | x | x | | | | | | | | |
| CA125 | x | x | x | | | | | | | | |
| SCC | x | x | x | | | | | | | | |
| CK 18 | x | x | x | | | | | | | | |
| ProGRP | x | x | x | | | | | | | | |
| Parainflu | | x | x | | | | | | | | |
| Pkyrs | | | x | | X | | | x | x | x | |
| Acn9459 | | | | X | X | x | x | x | x | x | x |
| Pub11597 | | | | X | X | x | x | x | x | x | x |
| Pub4789 | | | | X | X | x | x | x | x | x | x |
| TFA2759 | | | | X | X | x | x | x | x | x | x |
| TFA9133 | | | | X | X | x | x | x | | x | x |
| pub3743 | | | | | | | | | | | |
| pub8606 | | | | | | | | | | | |
| pub4487 | | | | | | | | | | | |
| pub4861 | | | | | | | | | | | |
| pub6798 | | | | | | | | | | | |
| tfa6453 | | | | | | | | | | | |
| hic3959 | | | | | | | | | | | |
| Threshold* | 1/8 | 4/9 | 4/10 | 3/5 | 3/6 | 2/7 | 3/7 | 3/8 | 3/7 | 3/7 | 3/6 |
| AUC | | 0.73 | 0.80 | 0.83 | 0.86 | | 0.87 | 0.91 | 0.90 | 0.89 | 0.86 |
| | | (0.04) | (0.03) | (0.02) | (0.02) | | (0.02) | (0.01) | (0.01) | (0.01) | (0.02) |
| Accuracy | | 66.0 | 70.0 | 77.0 | 80.0 | | 78.8 | 84.1 | 83.9 | 83.0 | 79.4 |
| | | (4.1) | (2.4) | (3.7) | (2.1) | | (2.0) | (2.0) | (1.9) | (1.9) | (3.6) |
| Sensitivity | 90.2 | 69.5 | 85.0 | 63.4 | 72.0 | 91.3 | 81.6 | 91.5 | 79.1 | 81.3 | 70.9 |
| | (3.1) | (8.5) | (5.0) | (4.6) | (3.5) | (2.0) | (2.3) | (1.4) | (1.4) | (1.8) | (4.3) |

TABLE 25a-continued small cohort

| Markers | 8 IA model | 9 IA Model | IA-pkyrs Model | MS Model | MS pkyrs Model | Mixed Model 1A | Mixed Model 1B | Mixed Model 2 | Mixed Model 3 | Mixed Model 4 | Mixed Model 5 |
|---|---|---|---|---|---|---|---|---|---|---|---|
| Specificity | 30 (4.7) | 62.0 (6.8) | 52.3 (3.9) | 93.3 (2.5) | 89.0 (2.6) | 42.7 (3.6) | 75.5 (3.1) | 75.1 (3.1) | 89.4 (3.5) | 84.8 (4.7) | 89.6 (3.0) |
| DFI | 0.71 | 0.49 | 0.50 | 0.37 | 0.30 | 0.58 | 0.31 | 0.26 | 0.23 | 0.24 | 0.31 |

*Predetermined Total Score. In the above Table, there is no difference between "x" and "X".

TABLE 25b small cohort

| Markers | Mixed model 6 | Mixed Model 7 | Mixed Model 8 | Mixed Model 9 | Mixed Model 10A | Mixed Model 10B |
|---|---|---|---|---|---|---|
| CK 19 | | x | | x | x | x |
| CA 19-9 | | | | | | |
| CEA | x | x | | x | x | x |
| CA15-3 | | | | | | |
| CA125 | | | | x | x | x |
| SCC | | | | x | x | x |
| CK 18 | x | | | x | x | x |
| ProGRP | | | | x | x | x |
| Parainflu | | | | | | |
| Pkyrs | x | | | | x | x |
| Acn9459 | x | x | | x | x | x |
| Pub11597 | x | x | x | x | x | x |
| Pub4789 | x | x | | x | x | x |
| TFA2759 | x | x | | x | x | x |
| TFA9133 | x | | | | | |
| pub3743 | | | x | | | |
| pub8606 | | | x | | | |
| pub4487 | | | x | | | |
| pub4861 | | | x | | | |
| pub6798 | | | x | | | |
| tfa6453 | | | x | | | |
| hic3959 | | | x | | | |
| Threshold* | 3/8 | 2/6 | 3/8 | 3/10 | 3/11 | 4/11 |
| AUC | 0.90 (0.01) | | | | | |
| Accuracy | 80.2 (1.7) | | | | | |
| Sensitivity | 92.6 (2.0) | 87.8 (2.3) | 88.2 (3.3) | 89.1 (3.4) | 94.3 (1.2) | 86.6 (4.40) |
| Specificity | 65.5 (2.7) | 63.7 (4.9) | 64.2 (3.7) | 52.3 (3.9) | 47.6 (4.9) | 63.9 (4.0) |
| DFI | 0.35 | 0.38 | 0.38 | 0.49 | 0.53 | 0.39 |

*Predetermined Total Score.
Tables 25a and b. Summary of various predictive models.

Similarly, for the large cohort, various predictive models can be optimized for overall accuracy, sensitivity, or specificity. Four potential models are summarized in Table 26 below.

TABLE 26

Four potential models.

large cohort

| Markers | MS Model 1 | MS Model 2 | MS Model 3 | MS Model 4 |
|---|---|---|---|---|
| acn6399 | x | x | x | x |
| pub3743 | x | x | x | x |
| pub8606 | x | x | x | x |
| pub11597 | x | x | x | x |
| tfa6453 | x | x | x | x |
| pub4487 | x | x | x | x |
| pub4861 | x | x | x | |
| pub6798 | x | x | | |
| hic3959 | x | | | |
| Threshold* | 3/9 | 3/8 | 3/7 | 2/6 |
| AUC | | | | |
| Accuracy | 75.7 (2.6) | 80.0 (2.0) | 84.2 (1.7) | 78.9 (2.6) |
| Sensitivity | 95.1 (2.0) | 89.7 (2.6) | 80.7 (4.4) | 88.5 (4.0) |
| Specificity | 67.7 (3.1) | 76.0 (2.2) | 85.7 (1.4) | 74.9 (2.7) |
| DFI | 0.33 | 0.26 | 0.24 | 0.28 |

*Predetermined Total Score.
In the above Table, there is no difference between "x" and "X".

Similarly, predictive models for the cyclin cohort (subset of individuals with measured anti-cyclin E2 protein antibodies and anti-cyclin E2 peptide antibodies) are summarized in Tables 27a and 27b below.

TABLE 27a

Cyclin cohort (234 samples)

| Markers | model A | model B | model C | model D | model E | model F | model G | model H | model I | model J | model |
|---|---|---|---|---|---|---|---|---|---|---|---|
| CK 19 | | | | | | | | | x | x | |
| CA 19-9 | | | | | | | | | | | |
| CEA | | | | | | | | | | | |
| CA15-3 | | | | | | | | | | | |
| CA125 | | | | | x | x | x | x | | | |
| SCC | | | | | | | | x | x | | |
| CK 18 | | | | | | | x | x | x | | |
| ProGRP | | | | | x | x | x | x | x | | |
| Parainflu | | | | | | | | | | | |
| Pkyrs | | | | x | x | x | x | x | x | | |
| Acn9459 | | | | | | | | | | | |
| Pub11597 | | | | | | | | | | x | x |
| Pub4789 | | | | | | | | | | | |

TABLE 27a-continued

Cyclin cohort (234 samples)

| Markers | model A | model B | model C | model D | model E | model F | model G | model H | model I | model J | model |
|---|---|---|---|---|---|---|---|---|---|---|---|
| TFA2759 | | | | | | | | | | | |
| TFA9133 | | | | | | | | | | | |
| Pub6453 | | | | | | | | | | | x |
| Pub2951 | | | | | | | | | | x | |
| Pub4861 | | | | | | | | | | x | |
| Pub2433 | | | | | | | | | | x | |
| Pub3743 | | | | | | | | | | | |
| Pub17338 | | | | | | | | | | | |
| TFA6652 | | | | | | | | | | | |
| Cyclin E2-1 pep | x | | | x | x | x | x | x | x | x | x |
| Cyclin E2 protein | | x | | | | | | | | | |
| Cyclin E2-2 pep | | | x | | | | | | | | |
| Threshold* | 0/1 | 0/1 | 0/1 | 0/2 | 0/3 | 0/4 | 0/5 | 0/6 | 0/7 | 2/6 | 1/3 |
| Accuracy | 79.0 | 75.4 | 67.4 | 84.1 | 86.2 | 85.2 | 83.5 | 81.2 | 80.4 | 88.4 | 88.4 |
| Sensitivity | 61.2 | 44.7 | 31.8 | 93.2 | 87 | 91.8 | 95.3 | 95.3 | 95.5 | 80.0 | 74.1 |
| Specificity | 89.9 | 94.2 | 89.2 | 72.9 | 85.6 | 81.3 | 76.2 | 72.7 | 71.4 | 93.5 | 97.1 |
| DFI | 0.40 | 0.56 | 0.69 | 0.28 | 0.19 | 0.20 | 0.24 | 0.28 | 0.29 | 0.21 | 0.26 |

*Predetermined Total Score.

TABLE 27b

Tables 27a and 27b provide predictive models for the cyclin cohort.

| Markers | model L | model M | model N | model O | model P | model Q | model R | model S | model T | model U | model V |
|---|---|---|---|---|---|---|---|---|---|---|---|
| CK 19 | | x | x | x | x | | | | | | |
| CA 19-9 | | | | | | | | | | | |
| CEA | | | x | x | x | x | x | | | | |
| CA15-3 | | | | | | | | | | | |
| CA125 | | | | | x | | | | | | |
| SCC | | | | | x | | | | | | |
| CK 18 | | | | | x | x | | | | | |
| ProGRP | | | | | x | x | x | x | x | x | |
| Parainflu | | | | | | | | | | | |
| Pkyrs | | | | | | | | | | | |
| Acn9459 | | | | | | | | | | | |
| Pub11597 | x | | | x | | | | | | | |
| Pub4789 | | | | | | | | | | | |
| TFA2759 | | | | | | | | | | | |
| TFA9133 | | | | | | | | | | | |
| Pub6453 | x | | | | | | | | | | |
| Pub2951 | | | | | | | | | | | |
| Pub4861 | | | | | | | | | | x | x |
| Pub2433 | | | | | | | | | | x | |
| Pub3743 | | | | | | | | | | x | x | x |
| Pub17338 | | | | | | | | | | x | x | x |
| TFA6652 | | | | | | | | | | x | | |
| Cyclin E2-1 pep | | x | x | x | x | x | x | x | x | x | |
| Cyclin E2 protein | x | | | | | | | | | | |
| Cyclin E2-2 pep | | | | | | | | | | | |
| Threshold* | 1/3 | 0/2 | 0/3 | 1/4 | 1/7 | 0/4 | 0/3 | 0/2 | 2/8 | 1/5 | 0/2 |
| Accuracy | 84.4 | 80.3 | 80.8 | 82.6 | 63.8 | 82.1 | 83.0 | 82.1 | 93.8 | 92.9 | 85.2 |
| Sensitivity | 64.7 | 80.0 | 81.1 | 58.8 | 94.1 | 80 | 75.3 | 72.9 | 90.6 | 89.4 | 85.9 |
| Specificity | 96.4 | 80.6 | 80.6 | 97.1 | 45.3 | 83.4 | 87.8 | 87.8 | 95.7 | 95 | 84.9 |
| DFI | 0.35 | 0.28 | 0.27 | 0.41 | 0.55 | 0.26 | 0.28 | 0.30 | 0.10 | 0.12 | 0.21 |

*Predetermined Total Score.

Similarly, predictive models using autoantibody assays are summarized in Table 28 below.

TABLE 28

Predictive models using autoAb assays.

| Markers | Model Aab1 | model Aab2 |
|---|---|---|
| TMP21 | x | x |
| NPC1L1C-domain | x | x |
| CCNE2BM-E2-1 | x | x |
| TMOD1 | x | x |
| CAMK1 | x | x |
| RGS1 | x | x |
| PACSIN1 | x | x |

TABLE 28-continued

Predictive models using autoAb assays.

| Markers | Model Aab1 | model Aab2 |
|---|---|---|
| p53 | x | x |
| RCV1 | x | |
| MAPKAPK3 | x | x |
| Threshold* | 1/10 | 1/9 |
| Accuracy | 82 | 82.9 |
| Sensitivity | 74.7 | 73.5 |
| Specificity | 86.4 | 88.4 |
| DFI | 0.29 | 0.29 |

*Predetermined Total Score.

Five of these models were used against the validation cohort. Table 29 below summarizes the clinical performance of each of the predictive models for the independent cohorts, small cohort and validation cohort.

TABLE 29

| | Mixed Model 7 | Mixed Model 1 | 8 IA model | MS Model 5 | Mixed Model 9 |
|---|---|---|---|---|---|
| CK 19 | x | x | x | | x |
| CEA | x | x | x | | x |
| CA19-9 | | | x | | |
| CA15-3 | | | x | | |
| CA125 | | | x | | x |
| SCC | | | x | | x |
| CK 18 | | | x | | x |
| proGRP | | | x | | x |
| parainfluenza | | | | | |
| acn9459 | x | x | | | x |
| pub11597 | x | x | | x | x |
| pub4789 | x | x | | | x |
| tfa2759 | x | x | | | x |
| tfa9133 | | x | | | |
| pub3743 | | | | x | |
| pub8606 | | | | x | |
| pub4487 | | | | x | |
| pub4861 | | | | x | |
| pub6798 | | | | x | |
| tfa6453 | | | | x | |
| hic3959 | | | | x | |
| pack-yr | | | | | |
| threshold | 2/6 | 2/7 | 1/8 | 3/8 | 3/10 |
| Small Cohort | | | | | |
| AUC | | | | | |
| accuracy | | | | | |
| sensitivity | 87.8 | 91.3 | 90.2 | 88.2 | 89.1 |
| specificity | 63.7 | 42.7 | 30.0 | 64.2 | 52.3 |
| DFI | 0.38 | 0.58 | 0.71 | 0.38 | 0.49 |
| Validation Cohort | | | | | |
| AUC | | | | | |
| accuracy | | | | | |
| sensitivity | 75.6 | 87.2 | 94.2 | 82.5 | 88.4 |
| specificity | 62.9 | 55.7 | 35.2 | 86.0 | 58.6 |
| DFI | 0.44 | 0.46 | 0.65 | 0.22 | 0.43 |

*Predetermined Total Score. In the above Table, there is no difference between "x" and "X".

Example 10

Biomarker Identification

A. HPLC Fractionation

In order to get the identity of the MS biomarker candidates in Table 22, it was necessary to first fractionate pooled and/or individual serum samples by reverse phase HPLC using standard protocols. Obtaining enough material for gel electrophoresis and for MS analysis necessitated several fractionation cycles. Individual fractions were profiled by MALDI-TOF MS and the fractions containing the peaks of interest were pooled together and concentrated in a speedvac. All other biomarker candidates were processed as described above.

Figure 2:
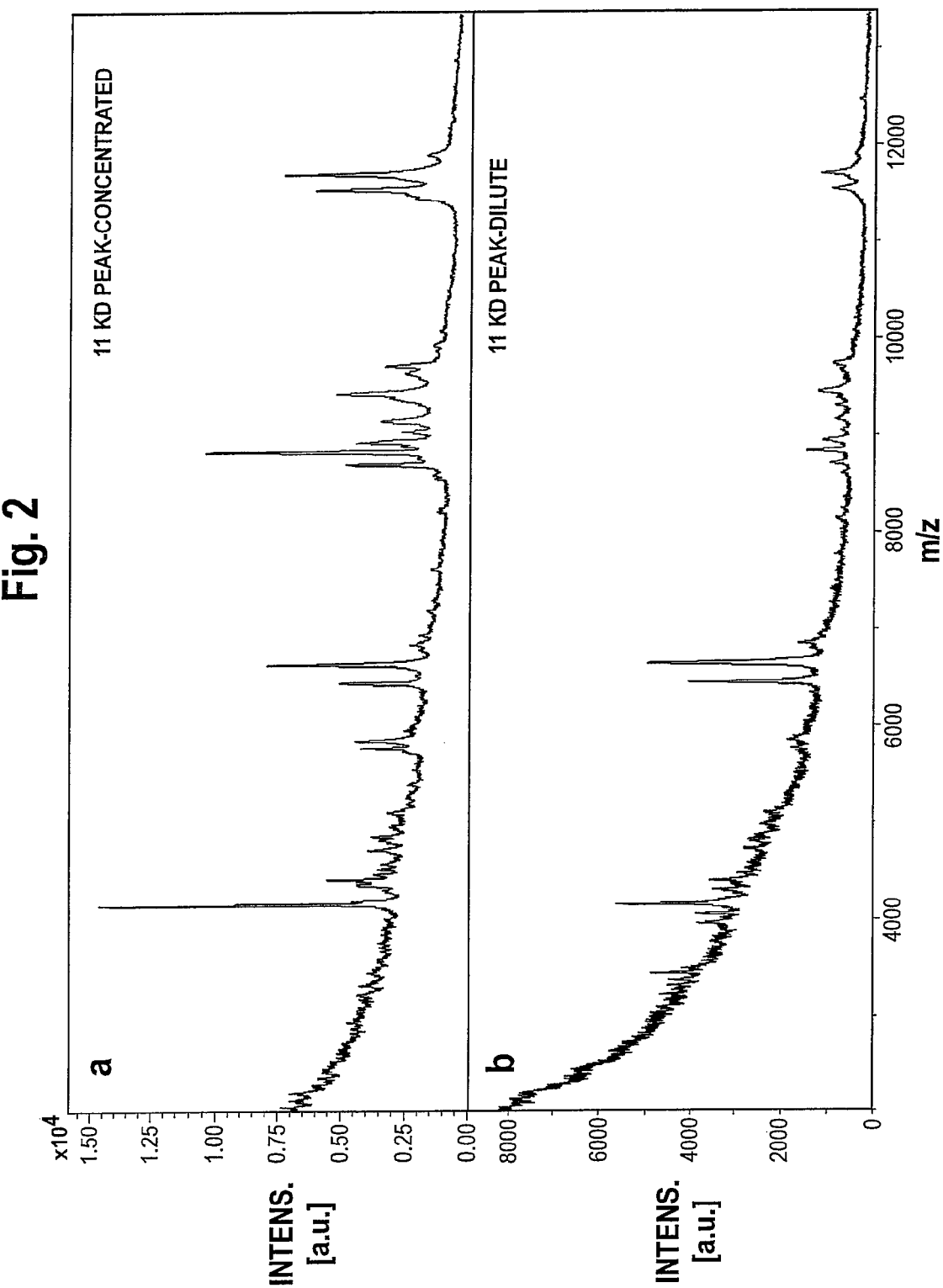
FIG. 2 is a MALDI-TOF MS Profile showing the Pub11597 biomarker candidate a) after concentrating pooled HPLC fractions and b) before the concentration process. The sample is still a complex mixture even after HPLC fractionation.

FIG. 2 shows a putative biomarker (pub11597) before and after concentration. Note that the biomarker candidate at 11 kDa in the starting sample is very dilute. After concentration the intensity is higher but the sample is not pure enough for analysis and necessitated further separation by SDS-PAGE in order to isolate the biomarker of interest.

B. In-Gel Digestion and LC-MS/MS Analysis

Figure 3:
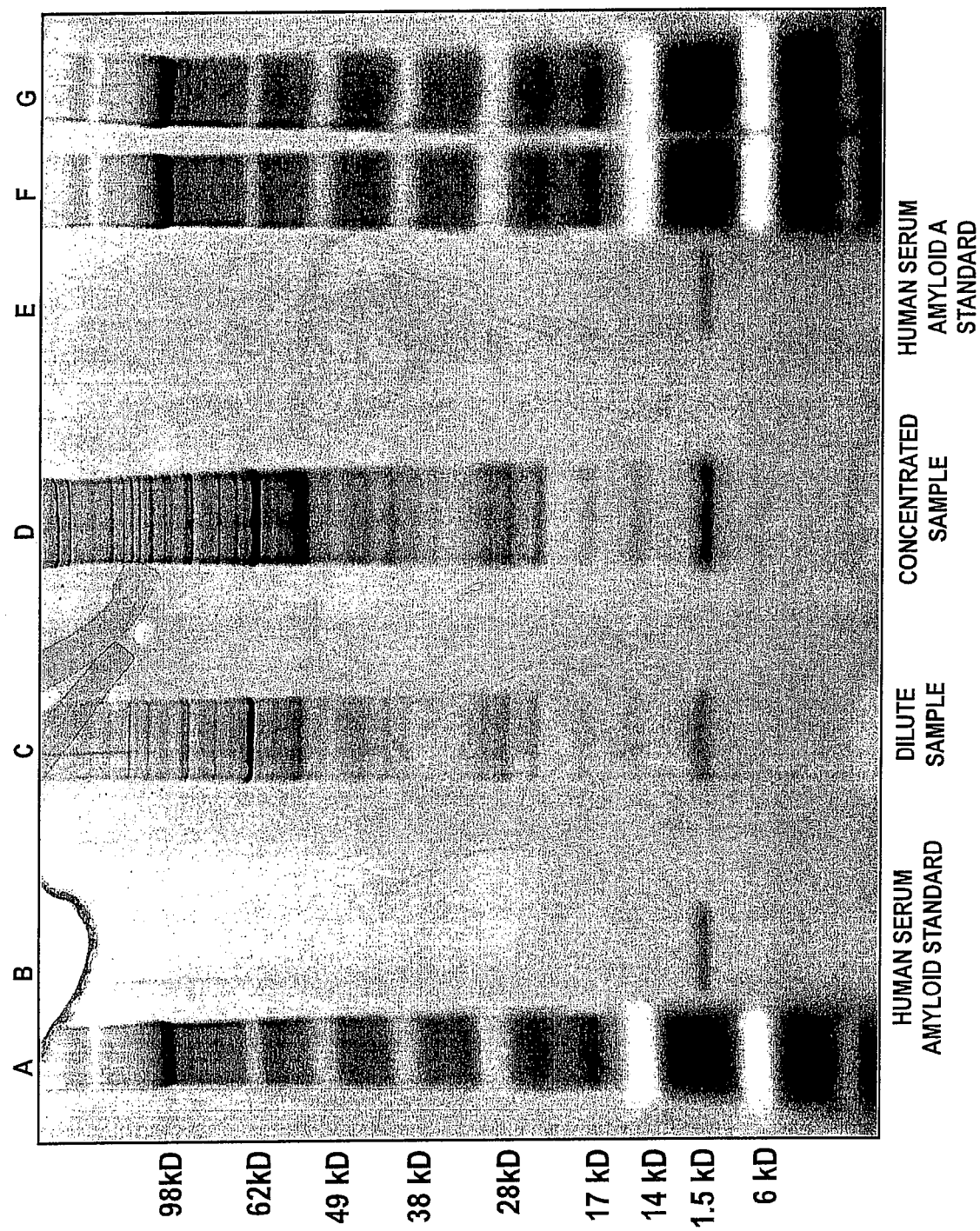
FIG. 3 is a stained gel showing the components of the various samples loaded in the gel. Lanes a, f and g show a mixture of standard proteins of known molecular masses for calibration purposes. Additionally, lanes b and e show a highly purified form of the suspected protein known as human serum amyloid A (HSAA), which was obtained commercially. Lanes c and d show the fractionated samples containing the putative biomarker. There is a component in the mixture that migrates the same distance as the HSAA standard. The bands having the same migration distance as the HSSA were excised from the gel and subjected to in-gel digestion and MS/MS analysis to confirm its identity.
Figure 4A:
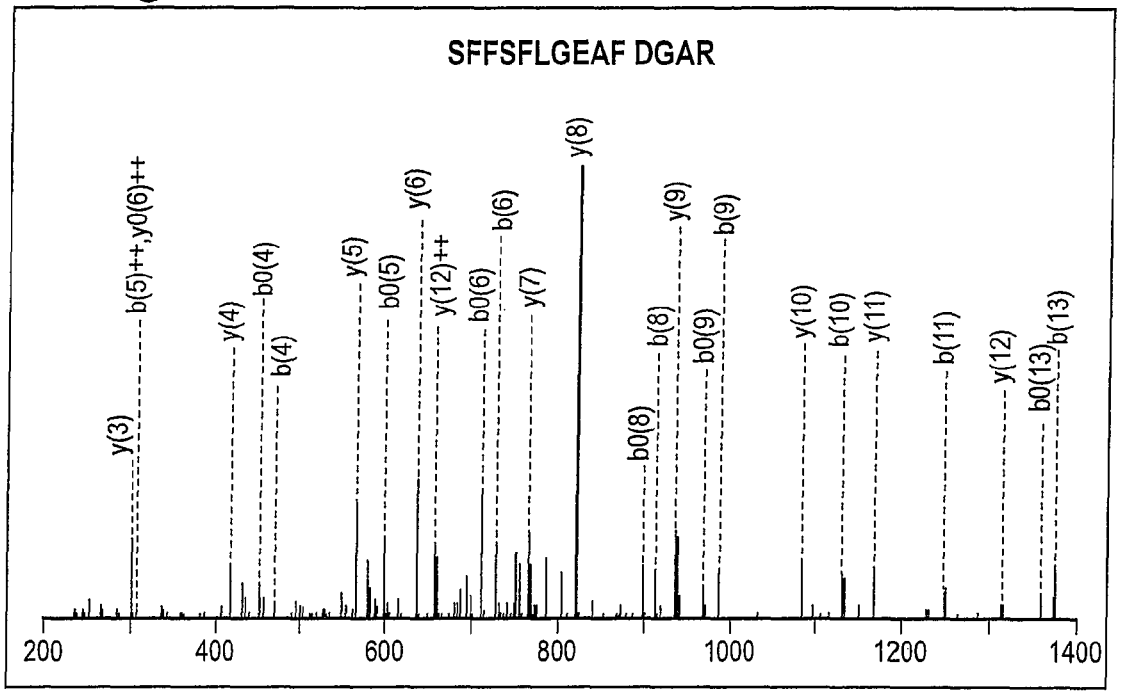
FIG. 4 is a LC-MS/MS of the tryptic digest of Pub11597. Panels a-d show the MS/MS of 4 major precursor ions. The b and y product ions have been annotated and the derived amino acid sequence is given for each of the four precursor ions. The database search using the molecular masses of the generated b and y ions identified the source protein as HSAA. The complete sequence of the observed fragment (MW=11526.51) is provided in SEQ ID NO:6.
Figure 4B:
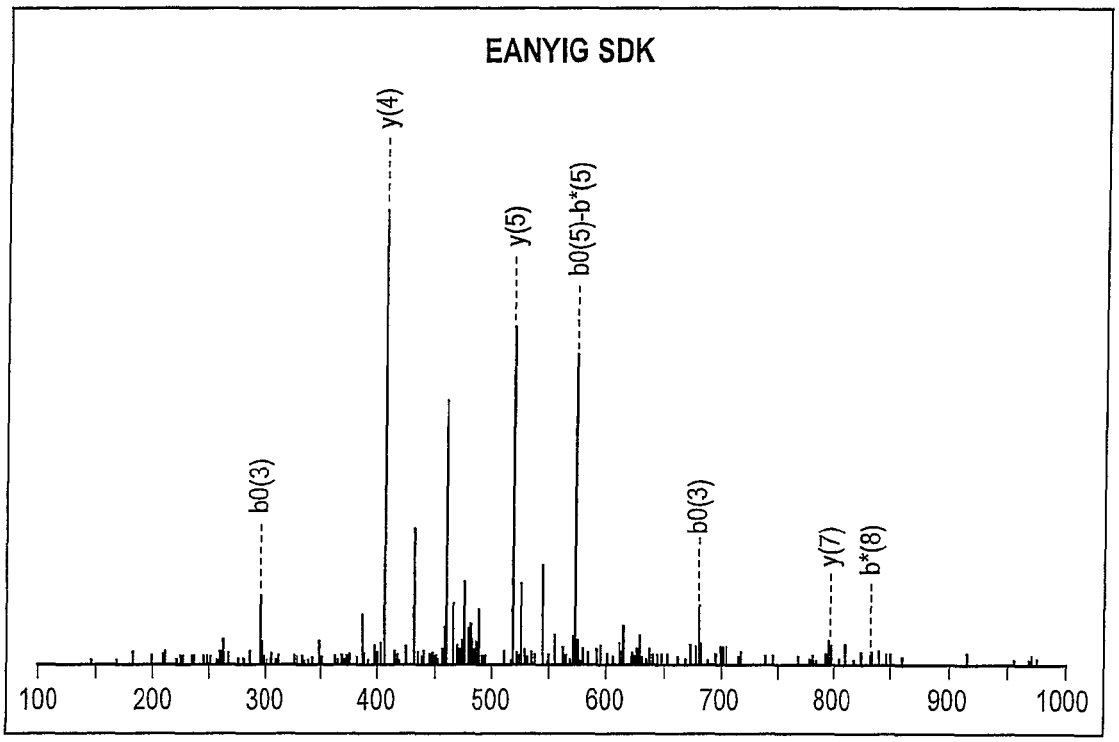
Figure 4C:
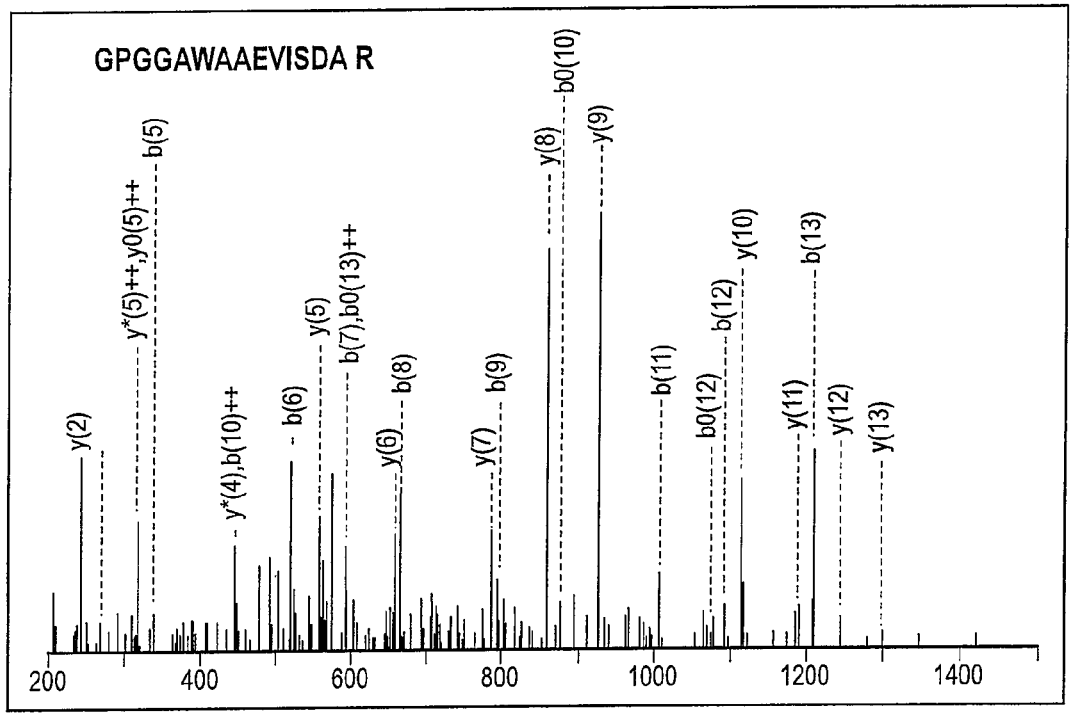
Figure 4D:
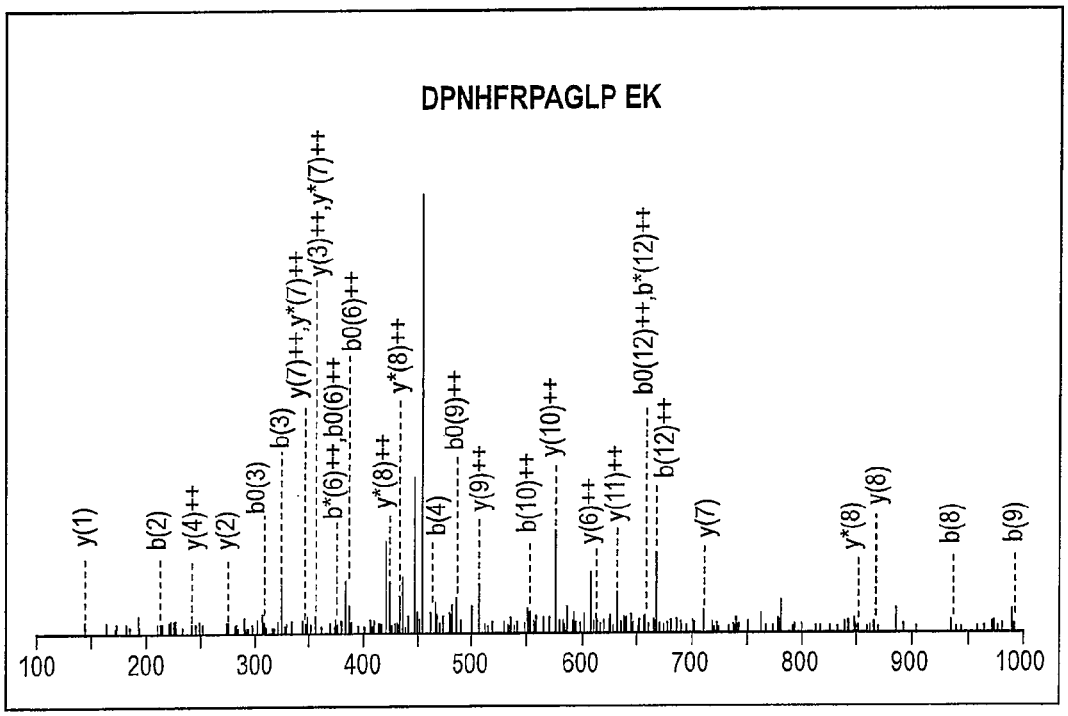

After concentration, the fractions containing the candidate biomarkers were subjected to SDS-PAGE to isolate the desired protein/peptide having the molecular mass corresponding to the candidate biomarker. Gel electrophoresis (SDS-PAGE) was carried out using standard methodology provided by the manufacturer (Invitrogen, Inc.). Briefly, the procedure involved loading the samples containing the candidate biomarkers and standard proteins of known molecular mass into different wells in the same gel as shown in FIG. 3. By comparing the migration distances of the standard proteins to that of the "unknown" sample, the band with the desired molecular mass was identified and excised from the gel.

The excised gel band was then subjected to automated in-gel tryptic digestion using a Waters MassPREP™ station. Subsequently, the digested sample was extracted from the gel and subjected to on-line reverse phase ESI-LC-MS/MS. The product ion spectra were then used for database searching. Where possible, the identified protein was obtained commercially and subjected to SDS-PAGE and in-gel digestion as previously described. Good agreement in the gel electrophoresis, MS/MS results and database search between the two samples was further evidence that the biomarker was correctly identified. As can be seen in FIG. 3, there is good agreement between the commercially available human serum amyloid A (HSAA) and the putative biomarker in the fractionated sample at 11.5 kDa. MS/MS analysis and database search confirmed that both samples were the same protein. FIG. 4 show the MS/MS spectra of the candidate biomarker Pub11597. The amino acid sequence derived from the b and y ions are annotated on top of each panel. The biomarker candidate was identified as a fragment of the human serum amyloid A (HSAA) protein.

The small candidate biomarkers that were not amenable to digestion were subjected to ESI-q-TOF and/or MALDI-TOF-TOF fragmentation followed by de-novo sequencing and database search (BLAST) to obtain sequence information and protein ID.

C. Database Search and Protein ID

In order to fully characterize the biomarker candidates it was imperative to identify the proteins from which they were derived. The identification of unknown proteins involved in-gel digestion followed by tandem mass spectrometry of the tryptic fragments. The product ions resulting from the MS/MS process were searched against the Swiss-Prot protein database to identify the source protein. For biomarker candidates having low molecular masses, tandem mass spectrometry followed by de-novo sequencing and database search was the method of choice for identifying the source protein. Searches considered only the Homo sapiens genome and mass accuracies of ±1.2 Da for precursor ions and ±0.8 Da for the product ions (MS/MS). Only one missed cleavage was allowed for trypsin. The only two variable modifications allowed for database searches were carbamidomethylation (C) and oxidation (M). A final protein ID was ascribed after reconciling Mascot search engine results and manual interpretation of related MS and MS/MS spectra. The accuracy of the results was verified by replicate measurements.

Table 30 above gives the source protein of the various candidate biomarkers with their protein ID. The markers were identified by in-gel digestion and LC-MS/MS and/or de-novo sequencing. Note that only the amino acid sequences of the observed fragments are shown and the average MW includes the PTM where indicated. Accession numbers were obtained from the Swiss-Prot database and are given as reference only. It is interesting to note that ACN9459 and TFA9133 are the same protein fragments with the exception that the latter has lost a sialic acid (−291.3 Da) from the glycosylated moiety. Both ACN9459 and TFA9133 were identified as a variant of apolipoprotein C III. Our findings are in agreement with the published known sequence and molecular mass of this protein (Bondarenko et. al, *J. Lipid Research*, 40:543-555 (1999)). Pub4789 was identified as alpha-1-antitrypsin protein. Close examination of the product ion spectra suggests that there might be a K to E substitution at the site indicated in Table 30. The uncertainty in the mass accuracy precluded the assignment. Additionally, the biomarkers in Table 30 above are known as acute phase proteins (which are also referred to herein as "acute phase responders (APR)" or "immune response biomarkers"). As discussed previously herein, acute phase proteins are members of the innate immune family of proteins.

Example 11

Detection of Lung Cancer

A. Immunoassay for peptide or protein: The biomarkers described in Example 9 above can be detected and measured by immunoassay techniques. For example, the Architect™ immunoassay system from Abbott Diagnostics is used for the automatic assay of an unknown in a sample suspected of containing a biomarker of the present invention. As is known in the art, the system uses magnetic microparticles coated with antibodies, which are able to bind to the biomarker of interest. Under instrument control, an aliquot of sample is mixed with an equal volume of antibody-coated magnetic microparticles and twice that volume of specimen diluent,

TABLE 30

| Candidate Marker | Accession # | Protein Name | Observed Peptide Sequence | Ave. MW (Da) |
|---|---|---|---|---|
| Pub11597 | Q6FG67 | Human Amyloid Protein A | SFFSFLGEAFDGARDMWRAYSDMREA NYIGSDKYFHARGNYDAAKRGPGGAW AAEVISDARENIQRFFGHGAEDSLAD QAANEWGRSGKDPNHFRPAGLPEKY (SEQ ID NO: 7) | 11526.51 |
| ACN9459 | P02656 | ApoCIII$_1$ | SEAEDASLLSFMQGYMKHATKTAKDA LSSVQESQVAQQARGWVTDGFSSLKD YWSTVKDKFSEFWDLDPEVRP*(T)S AVAA (SEQ ID NO: 8) *(Glycosylated site) | 9421.22 |
| TFA9133 | P02656 | ApoCIII$_1$ | ApoCIII$_1$after the loss of sialic acid | 9129.95 |
| Pub4789 | P01009 | alpha-1 anti-trypsin | LEAIPMSIPPEVKFN*(E)PFVFLMI DQNTKSPLFMGKVVNPTQK (SEQ ID NO: 8) *(possible K to E substitution) | 4776.69 |
| TFA2759 | Q56G89 | Human Albumin Peptide | DAHKSEVAHRFKDLGEENFKALVL (SEQ ID NO: 10) | 2754.10 | containing buffers, salt, surfactants, and soluble proteins. After incubation, the microparticles are washed with a wash buffer comprising buffer, salt, surfactant, and preservative. An aliquot of acridinium-labeled conjugate is added along with an equal volume of specimen diluent and the particles are redispersed. The mixture is incubated and then washed with wash buffer. The washed particles are redispersed in acidic pretrigger containing nitric acid and hydrogen peroxide to dissociate the acridinium conjugate from the microparticles. A solution of NaOH is then added to trigger the chemiluminescent reaction. Light is measured by a photomultiplier and the unknown result is quantified by comparison with the light emitted by a series of samples containing known amounts of the biomarker peptide used to construct a standard curve. The standard curve is then used to estimate the concentration of the biomarker in a clinical sample that was processed in an identical manner. The result can be used by itself or in combination with other markers as described below.

B. Multiplexed immunoassay for peptide or protein: When detection of multiple biomarkers from a single sample is needed, it may be more economical and convenient to perform a multiplexed assay. For each analyte in question, a pair of specific antibodies is needed and a uniquely dyed microparticle for use on a Luminex 100™ analyzer. Each capture antibody of the pair is individually coated on a unique microparticle. The other antibody of the pair is conjugated to a fluorophore such as R-Phycoerythrin. The microparticles are pooled and diluted to a concentration of about 1000 unique particles per microliter which corresponds to about 0.01% w/v. The diluent contains buffer, salt, and surfactant. If 10 markers are in the panel, total solids would be about 10,000 particles per microliter or about 0.1% solids w/v. The conjugates are pooled and adjusted to a final concentration of about 1 to 10 nM each in the microparticle diluent. To conduct the assay, an aliquot of sample suspected of containing one or more of the analytes is placed in an incubation well followed by a half volume of pooled microparticles. The suspension is incubated for 30 minutes followed by the addition of a half volume of pooled conjugate solution. After an additional incubation of 30 minutes, the reaction is diluted by the addition of two volumes of buffered solution containing a salt and surfactant. The suspension is mixed and a volume approximately twice that of the sample is aspirated by the Luminex 100™ instrument for analysis. Optionally, the microparticles can be washed after each incubation and then resuspended for analysis. The fluorescence of each individual particle is measured at 3 wavelengths; two are used to identify the particle and its associated analyte and the third is used to quantitate the amount of analyte bound to the particle. 100 microparticles of each type are measured and the median fluorescence for each analyte is calculated. Optionally, 50 or fewer microparticles of each type can be measured with little loss in precision and attendant sensitivity. The amount of analyte in the sample is calculated by comparison to a standard curve generated by performing the same analysis on a series of samples containing known amounts of the peptide or protein and plotting the median fluorescence of the known samples against the known concentration. An unknown sample is classified to be cancer or non-cancer based on the concentration of analyte (whether elevated or depressed) relative to known cancer or non-cancer specimens using models such as Split and Score Method or Split and Weighted Score Method as described in Example 7. Optionally, other methods such as Multiple of Median, described in Example 12, can be used as a scoring method for a panel of analytes.

For example, a patient may be tested to determine the patient's likelihood of having lung cancer using the 8 immunoassay (IA) panel of Table 18 and the Split and Score Method. After obtaining a test sample from the patient, the amount of each of the 8 biomarkers in the patient's test sample (i.e, serum) is quantified and the amount of each of the biomarkers is then compared to the corresponding predetermined split point (predetermined cutoff) for the biomarker, such as those listed in Table 18 (i.e, the predetermined cutoff that can be used for Cytokeratin 19 is 1.89 or 2.9). For each biomarker having an amount that is higher than its corresponding predetermined split point (predetermined cutoff), a score of 1 may be given. For each biomarker having an amount that is less than or equal to its corresponding predetermined split point (predetermined cutoff), a score of 0 may be given. The score for each of the 8 biomarkers are then combined mathematically (i.e., by adding each of the scores of the biomarkers together) to arrive at the total score for the patient. This total score becomes the panel score. The panel score is compared to the predetermined threshold (predetermined total score) of the 8 IA model of Table 25a, namely 1. A panel score greater than 1 would be a positive result for the patient. A panel score less than or equal to 1 would be a negative result for the patient. In the population study described in Example 9, this panel has demonstrated a specificity of 30%, a false positive rate of 70% and a sensitivity of 90%. A positive panel result for the patient has a 70% chance of being falsely positive. Further, 90% of lung cancer patients will have a positive panel result. Thus, the patient having a positive panel result may be referred for further testing for an indication or suspicion of lung cancer.

By way of a further example, again using the 8 IA panel and the Weighted Score Method, after obtaining a test sample from a patient, the amount of each of the 8 biomarkers in the patient's test sample (i.e, serum) is quantified and the amount of each of the biomarkers is then compared to the predetermined split points (predetermined cutoffs) such as those split points (cutoffs) listed in Table 17b (i.e, the predetermined cutoffs that can be used for Cytokeratin 19 are 1.2, 1.9 and 3.3). In this example, each biomarker has 3 predetermined split points (predetermined cutoffs). Therefore, 4 possible scores that may be given for each biomarker. The score for each of the 8 biomarkers are then combined mathematically (i.e., by adding each of the scores of the biomarkers together) to arrive at the total score for the patient. The total score then becomes the panel score. The panel score can be compared to the predetermined threshold (or predetermined total score) for the 8 IA model, which was calculated to be 11.2. A patient panel score greater than 11.2 would be a positive result. A patient panel score less than or equal to 11.2 would be a negative result. In the population study described in Example 9, this panel has demonstrated a specificity of 34%, a false positive rate of 66% and a sensitivity of 90%. The positive panel result has a 66% chance of being falsely positive. Further, 90% of lung cancer patients have a positive panel result. Thus, the patient having a positive panel result may be referred for further testing for an indication or suspicion of lung cancer.

C. Multiplexed immunoassay for patient autoantibodies: If the biomarker or biomarkers which are used to make a clinical diagnosis are circulating autoantibodies, an approach similar to that described above in Examples 11A and 11B can be used. If a single or small number of autoantibodies are to be used, the assay can be performed on an automated analyzer such as the Architect™ immunoassay system available from Abbott Diagnostics, Abbott Park, Ill. Positivity or negativity of the patient's serum for the biomarker is determined by comparison of the signal generated by the test serum with a standard or control serum and the patient is determined positive if the value exceeds a cutoff. If multiple autoantibodies are needed to make a determination, the Luminex 100™ analyzer, or related instruments, available from Luminex Corporation, Austin, Tex., is used. Pooled microparticles coated with the chosen autoantigens, as described in Example 12, below, are exposed to a diluted aliquot of the patient's serum (or plasma). After the first incubation, the particles are washed and exposed to a detection reagent comprising an antibody against human IgG tagged with a detectable label. After the second incubation, the particles are again washed and the detectable reagent is detected by use of a fluorescent label; if the detectable label is biotin, the fluorescent label can be either anti-biotin, avidin, or streptavidin attached to R-Phycoerythrin. Following a third incubation and wash (or aspiration), the particles are resuspended in buffer and introduced into the Luminex 100™ analyzer. Control particles can be carried through the process to test for non-specific binding (negative control) and specific binding (positive control). Likewise a procedural control, for example a particle coated with anti-human IgG, can be included. By comparison of the values obtained from the patient sample with negative samples, a single biomarker can be determined to be positive or negative. When measuring multiple autoantibodies, each biomarker in turn is measured and the results combined to arrive at an overall assessment of positivity or negativity for the patient. Multiple results can be optimally combined by using a data analysis tool such as the Split and Score method described in Example 11 B, above, or the Multiple of the Median (MOM) described in Example 12.

If both antigens and autoantibodies are desired to be run on each patient sample and the concentrations of the antigens are high enough to allow dilution comparable to that used in the autoantibody measurement, all the microparticles can be combined into one reagent and the test run on one aliquot of patient serum or plasma. The only modification to the autoantibody protocol is that in addition to the anti-human IgG reagent, detectably labelled antibodies against each of the antigen analytes must be included in the second reagent. All can be detected with a suitable r-Phycoerythrin reagent at the last step. The antigen assays may require high sensitivity, and therefore, the sample cannot be diluted appropriately for the autoantibody determination. In this case, the antigens are measured in a minimally diluted serum sample and the autoantibodies are measured in a highly diluted serum sample. Although doubling the number of determinations, both types of measurements can be easily performed on the Luminex family of instruments. Alternatively, the measurements can be made on other flow cytometers, such as those available from BD Biosciences, San Jose, Calif. Changing the format to an array, similar to the ProtoArray from Invitrogen, Carlsbad, Calif., removes the convenience of individually prepared microparticle reagents, but is technically feasible.

D. Immuno mass spectrometric analysis: Sample preparation for mass spectrometry can also use immunological methods as well as chromatographic or electrophoretic methods. Superparamagnetic microparticles coated with antibodies specific for a peptide biomarker are adjusted to a concentration of approximately 0.1% w/v in a buffer solution containing salt. An aliquot of patient serum sample is mixed with an equal volume of antibody-coated microparticles and twice that volume of diluent. After an incubation, the microparticles are washed with a wash buffer containing a buffering salt and, optionally, salt and surfactants. The microparticles are then washed with deionized water. Immunopurified analyte is eluted from the microparticles by adding a volume of aqueous acetonitrile containing trifluoroacetic acid. The sample is then mixed with an equal volume of sinapinic acid matrix solution and a small volume (approximately 1 to 3 microliters) is applied to a MALDI target for time of flight mass analysis. The ion current at the desired m/z is compared to the ion current derived from a sample containing a known amount of the peptide biomarker which has been processed in an identical manner.

It should be noted that the ion current is directly related to concentration and the ion current (or intensity) at a particular m/z value (or ROI) can be converted to concentration if so desired. Such concentrations or intensities can then be used as input into any of the model building algorithms described in Example 7.

E. Mass spectrometry for ROIs: A blood sample is obtained from a patient and allowed to clot to form a serum sample. The sample is prepared for SELDI mass spectrometric analysis and loaded onto a Protein Chip in a Bioprocessor and treated as provided in Example 2. The ProteinChip is loaded onto a Ciphergen 4000 MALDI time of flight mass spectrometer and analyzed as in Example 3. Each spectrum is tested for acceptance using multivariate analysis. For example, the total ion current and the spectral contrast angle (between the unknown sample and a known reference population) are calculated. The Mahalanobis distance is then determined. For the spectrum whose Mahalanobis distance is less than the established critical value, the spectrum is qualified. For the spectrum whose Mahalanobis distance is greater than the established critical value, the spectrum is precluded from further analysis and the sample should be re-run. After qualification, the mass spectrum is normalized.

The resulting mass spectrum is evaluated by measuring the ion current in regions of interest appropriate for the data analysis model chosen. Based on the outcome of the analysis, the patient is judged to be at risk for or have a high likelihood of having lung cancer and should be taken through additional diagnostic procedures.

For use of the Split and Score Method, the intensities in the ROIs at the m/z values given in Table 5 are measured for the patient. The patient result is scored by noting whether the patient values are on the cancer side or the non-cancer side of the average split point values given in Table 7. A score of 1 is given for each ROI value found to be on the cancer side of the split point. Scores of 3 and above indicate the patient is at elevated risk for cancer and should be referred for additional diagnostic procedures.

Example 12

Multiple of Median Method

The multiple of median (MoM) method of data integration allows scoring of a panel of biomarkers. In the multiple of median method, the median value of each biomarker in a normal cohort is determined. This median value is used to normalize all measurements of that specific biomarker. The MoM has been used to analyze both serum antibody and serum antigen levels. W. Kutteh, et al. (*Obstet. Gynecol.* 84:811-815 (1994)) used the MoM to report anti-phospholipid antibody levels in patients. Additionally, G. Palomaki et al., (*Clinc. Chem. Lab. Med.*) 39:1137-1145 (2001)) have used the MoM to analyze serum protein levels. Thus any measured biomarker level is divided by the median of the normal group, resulting in a multiple of the median. These multiples of median values are combined (namely, summed or added) for each biomarker in the panel resulting in a panel MoM value or MoM score for each sample. For clinical purposes, a cutoff can be determined for the panel MoM value indicating the presence or risk of disease.

Figure 6:
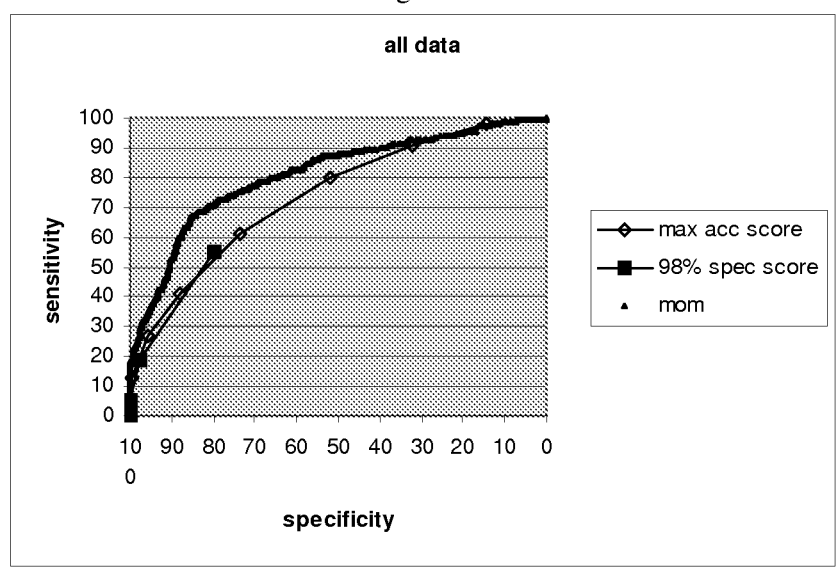
FIG. 6 gives the AUC for a 7 autoantibody panel tested on lung cancer, benign and normal subjects and the values for all the measurements determined using the multiple of median (MoM) method and the split and scoring method (SSM).

A feature of the MoM method is the retention of the distribution of the data in the population. As an example, seven autoantibodies were measured in 1059 individuals (291 lung cancer, 387 benign lung disease, and 381 normals). The median values of the seven autoantibody measurements was determined for the normal cohort and all measurements were converted to a multiple of median value. The seven multiple of median values were summed for all 1059 individuals. These 1059 panel MoM values were subjected to a receiver-operator characteristic curve (ROC curve). The resulting curve is shown in FIG. 6. Also plotted in FIG. 6 are the resulting curves from the binary split and scoring method using split points determined by maximum accuracy or by 98% specificity requirements.

Example 13

An Autoantibody Bead Array

A. Commercially available human proteins (See, Table 31, below) were attached to Luminex™ SeroMap™ beads (Austin, Tex.) and the individual beadsets were combined to prepare the reagent. Portions of the reagent were exposed to the human serum samples under conditions that allow any antibodies present to bind to the proteins. The unbound material was washed off and the beads were then exposed to a fluorescent conjugate of R-phycoerythrin linked to an antibody that specifically binds to human IgG. After washing, the beads were passed through a Luminex™ 100 instrument, which identified each bead according to its internal dyes, and measured the fluorescence bound to the bead, corresponding to the quantity of antibody bound to the bead. In this way, the immune responses of 772 samples (251 lung cancer, 244 normal, 277 benign) against 21 human proteins, as well as several non-human proteins for controls (bovine serum albumin (BSA) and tetanus toxin), were assessed.

B. Coating of Luminex SeroMap™ Beads with Antigens

Beads for this study were coated as indicated by the direct method described in Example 3B, the preactivation method described in Example 4E, or by passive adsorption described here:

To 100 uL Luminex SeroMap bead added the appropriate volume corresponding to 2.5 ug of the protein to be coated, and the mixture vortexed, and left at room temperature in the dark. After 90 min the mixtures were placed at 37° C. for 60 minutes, then 1 mL PBN/Tween added and the mixtures vortexed and spun down. The pellets were resuspended in 1 mL PBN/Tween and the mixtures sonicated. The beads were spun down and the pellets resuspended in 500 uL PBN/Tween.

C. Testing of Serum Samples with Coated Beads

Serum samples were prepared in microplates at a 1:30 dilution in PBN, with 80 samples per microplate. Protocol: to wells of 1.2u Supor filter plate 100 uL PBN/Tween was added After about 5 minutes, a vacuum was applied. When the wells were empty, the bottom of the plate was blotted with paper towel and 50 uL IX Master Mix added per well. To each well 20 uL 1:30 sample was added from sample plate and then incubate for 60 minutes on shaker at maximum shake. A vacuum was applied to remove all liquid. 100 uL PBN/Tween was added and a vacuum applied to remove all liquid. 100 uL PBN/Tween was added, placed on shaker for 10 minutes and then a vacuum applied to remove all liquid. 100 uL PBN/Tween was added, placed on a shaker for 10 minutes and a vacuum applied to remove all liquid. 100 uL 1:500 conjugate (20.8 uL RPEantiHumanIgG in 10.4 mL PBN/Tween) was added to each well, agitated with pipets, placed on the shaker for 30 minutes and a vacuum applied to remove all liquid. 100 uL PBN/Tween was added, agitated with pipets, transferred to a microplate and run on Luminex.

D. Analysis of Autoantibody Panels a. ROC Analysis

The raw result recorded for each autoantigen tested with individual samples was the median value. These results were subjected to a Receiver Operator Characteristic (ROC) analysis and the Area Under the Curve (AUC) was calculated for discriminating cancer from not cancer groups. Table 31 below, reports the AUC values for the individual autoantigens.

TABLE 31

| Bead | Prep | Coating | name | Source | AUC |
|---|---|---|---|---|---|
| 43 | Oct. 03, 2006 | Preactivate | CCNE2 | Abnova | 0.60 |
| 1 | Oct. 04, 2006 | Preactivate | TMP21-ECD | Abbott | 0.64 |
| 5 | Oct. 04, 2006 | Preactivate | NPC1L1C-domain | Abbott | 0.64 |
| 14 | Oct. 04, 2006 | Preactivate | PSEN2 (1-86aa) his | Abbott | 0.60 |
| 55 | Oct. 05, 2006 | Preactivate | CAMK-1 | Invitrogen | 0.61 |
| 49 | Oct. 18, 2006 | Direct | CCNE2 | Genway | 0.70 |
| 61 | Dec. 05, 2006 | Preactivate | tropomyosin1 | Invitrogen | 0.60 |
| 62 | Dec. 05, 2006 | Preactivate | PDZK1 | Invitrogen | 0.57 |
| 63 | Dec. 05, 2006 | Preactivate | ACRV1 | Invitrogen | 0.59 |
| 64 | Dec. 05, 2006 | Preactivate | DNAJB1 | Invitrogen | 0.58 |
| 65 | Dec. 05, 2006 | Preactivate | NRBF2 | Invitrogen | 0.59 |
| 66 | Dec. 05, 2006 | Preactivate | C21orf7 | Invitrogen | 0.56 |
| 67 | Dec. 05, 2006 | Preactivate | MAPKAPK3 | Invitrogen | 0.58 |
| 68 | Dec. 05, 2006 | Preactivate | PKCCKS | Invitrogen | 0.58 |
| 69 | Dec. 05, 2006 | Preactivate | SMAD1 | Invitrogen | 0.57 |
| 70 | Dec. 05, 2006 | Preactivate | DDAH2 | Invitrogen | 0.55 |
| 71 | Dec. 05, 2006 | Preactivate | UROS | Invitrogen | 0.59 |
| 72 | Dec. 05, 2006 | Preactivate | CDCA4 | Invitrogen | 0.54 |
| 73 | Dec. 05, 2006 | Preactivate | IITP | Invitrogen | 0.54 |
| 74 | Dec. 05, 2006 | Preactivate | LRRIQ2 | Invitrogen | 0.56 |
| 75 | Dec. 05, 2006 | Preactivate | SCF7m6os | Invitrogen | 0.60 |
| 76 | Dec. 05, 2006 | Preactivate | SH3PX3 | Invitrogen | 0.57 |
| 77 | Dec. 05, 2006 | Preactivate | TFPT | Invitrogen | 0.58 |
| 79 | Dec. 05, 2006 | Preactivate | RPE | Invitrogen | 0.55 |
| 56 | Dec. 11, 2006 | Preactivate | WW-E3 | Invitrogen | 0.60 |
| 57 | Dec. 11, 2006 | Preactivate | C1orf117 | Invitrogen | 0.62 |
| 58 | Dec. 11, 2006 | Preactivate | C9orf11 | Invitrogen | 0.60 |
| 59 | Dec. 11, 2006 | Preactivate | paralemmin | Invitrogen | 0.61 |
| 60 | Dec. 11, 2006 | Preactivate | CDC37-1 | Invitrogen | 0.60 |
| 78 | Dec. 11, 2006 | Preactivate | TFE3 | Invitrogen | 0.56 |
| 80 | Dec. 11, 2006 | Preactivate | CCNE2 | Invitrogen | 0.58 |
| 26 | Feb. 13, 2007 | Passive | p53 | Biomol | 0.69 |
| 27 | Feb. 13, 2007 | Passive | MAPKAPK3 | Genway | 0.70 |
| 30 | Feb. 13, 2007 | Direct | BM-E2-1 | Abbott | 0.73 |
| 31 | Feb. 13, 2007 | Passive | Aldolase | Sigma | 0.62 |
| 36 | Feb. 14, 2007 | Preactivate | TMOD-1 | Lab Vision | 0.67 |
| 32 | Feb. 15, 2007 | Direct | NY-ESO-1 | NeoMarkers | 0.66 |
| 33 | Feb. 15, 2007 | Direct | HDJ1 | Alexis | 0.64 |
| 23 | Feb. 19, 2007 | Direct | IgG | Abbott | 0.53 |
| 38 | Feb. 19, 2007 | Direct | BSA | Sigma | 0.60 |
| 40 | Feb. 19, 2007 | Direct | H. Pylori | Fitzgerald | 0.81 | b. Scoring Method

A binary scoring method was used to assess multiple panels of biomarkers in discriminating cancer from not cancer groups. Table 32, below, lists the split point (cutoff) used for each biomarker. Table 33 below identifies the individual markers in each panel and the AUC for each panel.

TABLE 32

| Biomarker | split point (max acc) | above split point |
|---|---|---|
| p53 | 84 | Cancer |
| NY-ESO-1 | 100 | Cancer |
| cyclin e2-1 pep | 653 | Cancer |
| Mapkapk | 54.5 | Cancer |
| Cyfra | 1.89 | Cancer |
| Cea | 4.82 | Cancer |
| ca125 | 22.4 | Cancer |
| Scc | 1.1 | Cancer |
| Tps | 55.5 | Cancer |
| Progrp | 11.8 | Cancer |
| 4789 | 193.4 | Cancer |
| 11597 | 34.4 | Cancer |

TABLE 32-continued

| Biomarker | split point (max acc) | above split point |
|---|---|---|
| 2759 | 575.5 | not cancer |
| acn9459 | 287.3 | not cancer |

C. Multiple of Median

The raw data for each biomarker was converted to a multiple of median value by dividing by the median value of the "normal" group. For each panel, the multiple of median values are summed to provide a panel multiple of median value for each sample. These panel multiple of median values are subjected to a Receiver Operator Characteristic analysis and the AUC is reported in Tables 33a and 33b below.

TABLE 33a

| | Markers | Aab/IA/MS | | | | | | | | | | | | | |
|---|---|---|---|---|---|---|---|---|---|---|---|---|---|---|---|
| | | 4/6/4 | 4/4/2 | 4/4/1 | 4/2/1 | 4/0/4 | 4/4/0 | 4/6/0 | 4/2/0 | 0/4/1 | 0/6/0 | 0/4/0 | 4/0/0 | 8/0/0 | 0/0/4 |
| 8 auto antigens | cyclin e2-1 | x | x | x | x | x | x | x | x | | | | x | x | |
| | mapkapk3 | x | x | x | x | x | x | x | x | | | | x | x | |
| | p53 | x | x | x | x | x | x | x | x | | | | x | x | |
| | tmod-1 | | | | | | | | | | | | | x | |
| | nyeso | x | x | x | x | x | x | x | x | | | | x | x | |
| | hdj1 | | | | | | | | | | | | | x | |
| | npc111c | | | | | | | | | | | | | x | |
| | tmp21 | | | | | | | | | | | | | x | |
| 6 immuno Assays | ck19 | x | x | x | x | | x | x | x | x | x | x | | | |
| | cea | x | x | x | x | | x | x | x | x | x | x | | | |
| | ca125 | x | x | x | | | x | x | | x | x | x | | | |
| | scc | x | | | | | x | | | | x | | | | |
| | progrp | x | x | x | | | x | x | | x | x | x | | | |
| | tps | x | | | | | x | | | | x | | | | |
| 4 mass spec | pub11597 | x | x | x | x | x | | | | x | | | | | x |
| | pub4789 | x | | | | x | | | | | | | | | x |
| | tfa2759 | x | | | | x | | | | | | | | | x |
| | acn9459 | x | x | | | x | | | | | | | | | x |
| AUC | binary score | 0.88 | 0.88 | 0.87 | 0.85 | 0.85 | 0.84 | 0.83 | 0.81 | 0.81 | 0.77 | 0.77 | 0.77 | 0.75 | 0.78 |
| | MoM | 0.88 | 0.88 | 0.88 | 0.86 | 0.82 | 0.88 | 0.88 | 0.85 | 0.83 | 0.81 | 0.82 | 0.81 | 0.81 | 0.76 |

TABLE 33b

Leave-one-out analysis on 14 marker panel using MoM data

| | Markers | Aab/IA/MS | | | | | | | | | | | |
|---|---|---|---|---|---|---|---|---|---|---|---|---|---|
| | | 2/1/0 | 2/2/0 | 3/2/0 | 3/3/0 | 3/4/0 | 4/4/0 | 4/4/1 | 4/4/2 | 4/4/3 | 4/5/3 | 4/5/4 | 4/6/4 |
| 8 auto Antigens | Cyclin e2-1 | x | x | X | x | x | x | x | X | x | x | x | x |
| | mapkapk3 | | | | | | x | x | X | x | x | x | x |
| | p53 | x | x | X | x | x | x | x | X | x | x | x | x |
| | tmod-1 | | | | | | | | | | | | |
| | NY-ESO-1 | | | | X | x | x | x | X | x | x | x | x |
| | hdj1 | | | | | | | | | | | | |
| | npc111c | | | | | | | | | | | | |
| | tmp21 | | | | | | | | | | | | |
| 6 immuno Assays | ck19 | | | | | x | x | x | X | x | x | x | x |
| | Cea | | x | X | x | x | x | x | X | x | x | x | x |
| | ca125 | | | | x | x | x | x | X | x | x | x | x |
| | Scc | | | | | | | | | | | | x |
| | Progrp | x | x | X | x | x | x | x | X | x | x | x | x |
| | Tps | | | | | | | | | | x | x | x |
| 4 mass spec | pub11597 | | | | | | | | | | | x | x |
| | pub4789 | | | | | | | | | X | x | x | x |
| | tfa2759 | | | | | | | | x | X | x | x | x |
| | acn9459 | | | | | | | | | x | x | x | x |
| AUC | Binary score | 0.76 | 0.79 | 0.82 | 0.83 | 0.83 | 0.84 | 0.86 | 0.87 | 0.88 | 0.88 | 0.88 | 0.88 |
| | MoM | 0.82 | 0.84 | 0.86 | 0.87 | 0.88 | 0.88 | 0.88 | 0.88 | 0.88 | 0.88 | 0.88 | 0.88 |

As can be seen comparing the panels in the above Tables 33a and 33b with only autoantigens as biomarkers, the 4/0/0 panel including NY-ESO-1, p53, mapkapk3, and cyclin E2-1 peptide was as good as the 8/0/0 panel including four more autoantigens. Furthermore, the highest AUC values were obtained when at least three autoantigens were included in the panel, namely, NY-ESO-1, p53 and cyclin E2-1 peptide.

In the leave-one-out analysis (Table 33b above), the same AUC was achieved by both the Multiple of Median (MoM) and the binary scoring methods. However, a larger panel of biomarkers was required with the binary score method compared to the MoM analysis method. This method (Multiple of Median) determined that panel 3/4/0 including autoantibodies against NY-ESO-1, p53, and cyclin E2-1 and tumor antigens CK19, CEA, CA125 and proGRP provided the highest AUC achievable with the fewest biomarkers. Adding additional biomarkers, at least in this Example, did not change the AUC. However, using the binary score method, the panel with the highest AUC and fewest biomarkers was 4/4/3 including autoantibodies against NY-ESO-1, p53, cyclin E2-1, and mapkapk3 and tumor antigens CK19, CEA, CA 125, and proGRP and mass spectrometry biomarkers PUB4789, Tfa2759, and ACN9459.

Figure 7:
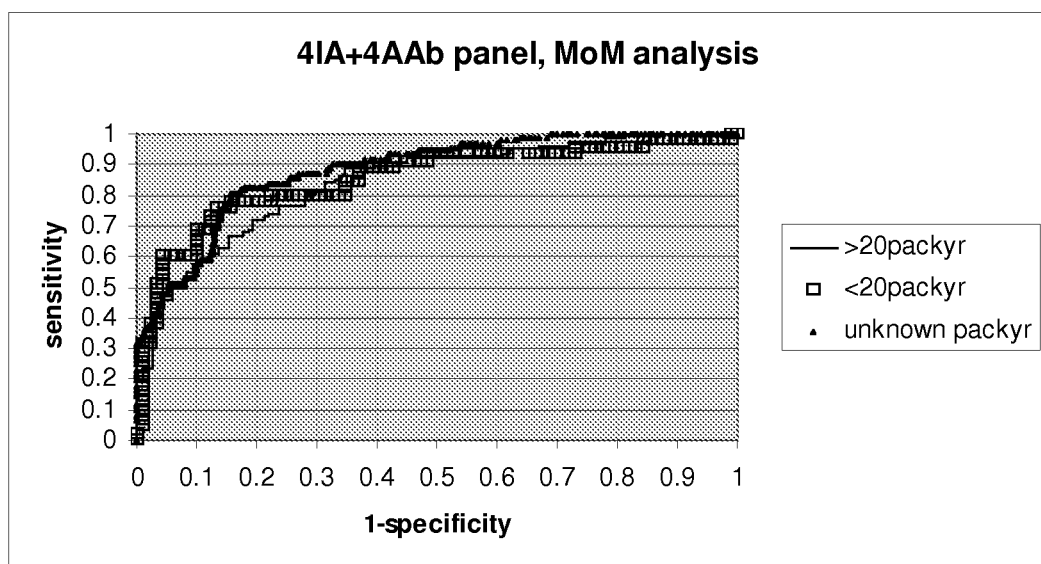
FIG. 7 gives the AUC for a 4 immunoassay and 4 autoantigen panel tested on subjects with a heavy smoking history (greater than 20 pack years), on subjects with a light smoking or non-smoking history (less than 20 pack years) and on subjects whose smoking history was unknown.

The panel 4/4/0 (Tables 33a and 33b above) was tested in the heavy smoker group (≥20 packyrs), the light smoker and non-smoker group (<20 packyrs) and the group with unknown packyear history. Individual patients were represented in only one group (Table 34). The panel performed similarly in distinguishing cancers from non-cancers whether all individuals were heavy smokers, whether all individuals were light or non-smokers or whether smoking histories were unknown (See, FIG. 7). The test performed equally well in all three groups demonstrating the result to be independent of smoking history. The ability to distinguish cancer from non-cancer patients in a heavy smoking cohort was 0.84, in a light or non-smoking cohort was 0.85 and in a cohort with unknown smoking history was 0.88.

TABLE 34

|  | >20 py | <20 py | unknown py |
|---|---|---|---|
| cancer | 127 | 45 | 92 |
| early | 85 | 25 | 46 |
| late | 42 | 20 | 46 |
| not cancer | 118 | 89 | 305 |
| benign | 109 | 85 | 76 |
| normal | 9 | 4 | 229 |
| AUC | 0.844 | 0.852 | 0.881 |

The individual cancer patients were grouped according to stage of lung cancer at diagnosis. Early stage lung cancer was defined as stages I and II. Late stage lung cancer was defined as stages III and IV. The 4/4/0 panel was tested for its ability to differentiate cancer from non-cancer using either the benign lung disease cohort as control or the normal cohort as control. Individual patients were represented in only one group. Table 35, below identifies the number of patients in each group and the AUC for each comparison.

TABLE 35

|  |  |  | cancer | |
|---|---|---|---|---|
|  |  | n | early (156) | late (108) |
| not cancer | normal | (241) | 0.869 | 0.927 |
|  | benign | (270) | 0.814 | 0.894 |

Significant improvement has been made in the differentiation of early stage lung cancer and benign lung disease using the 4/4/0 panel and others similarly composed. In the FIG. 8 and Table 36a, each individual biomarker was tested for its ability to differentiate early and late stage lung cancer from normal and benign lung disease cohorts. It is clear that tumor antigens (CK19, CA19-9, CEA, CA15-3, CA125, SCC, CK18, and proGRP) all demonstrate a significant stage dependence, in that late stage disease is differentiated from normals and benigns with some proficiency (AUC-0.7-0.8), however, differentiation of early stage lung cancer from normals and benigns is less proficient (AUC~0.5-0.7).

Figure 8:
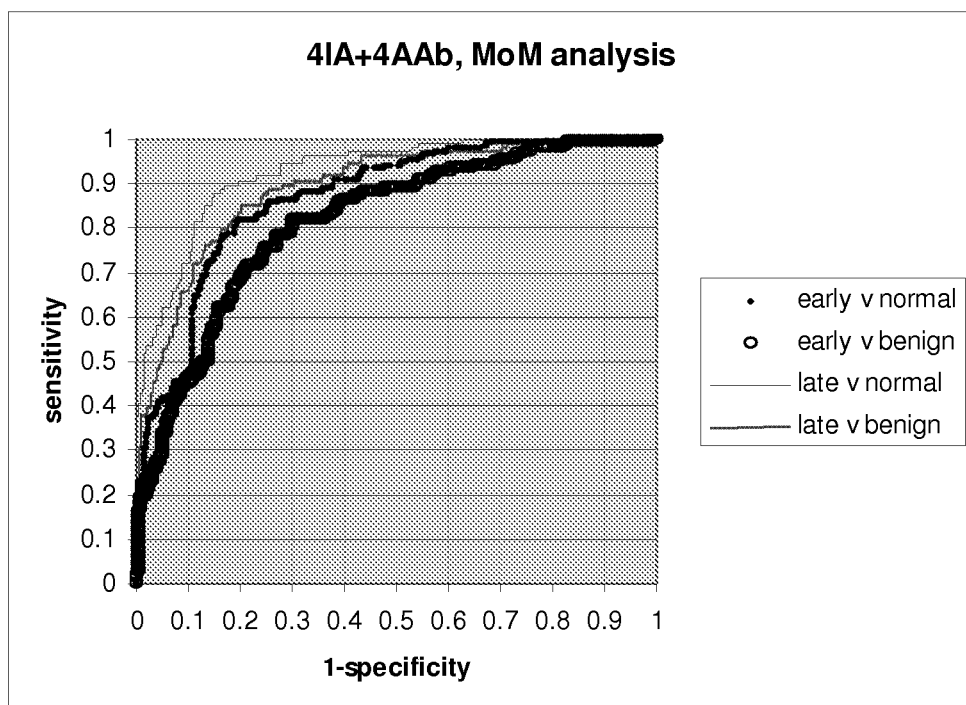
FIG. 8 gives the AUC for a 4 immunoassay and 4 autoantigen panel tested on subjects having early stage lung cancer and benign lung disease. This

Immune response markers including haptoglobin, serum amyloid A, C-reactive protein, and apolipoprotein CIII demonstrate a similar stage dependence as the tumor antigens (FIG. 8).

The autoantibodies as individual biomarkers are much less stage dependent. Early and late stage lung cancers are differentiated from normals and benigns with almost equivalent proficiency. The better performing autoantigens include, p53, mapkapk3, cyclin E2-1, NY-ESO-1, HDJ1 and tmod, having AUCs ranging from 0.6-0.75.

The MS markers (4789, 11597, 2759, and ACN9459, each of which is a APR) behave similarly to the autoantibodies in that there is less stage dependence in their behavior.

Figure 9:
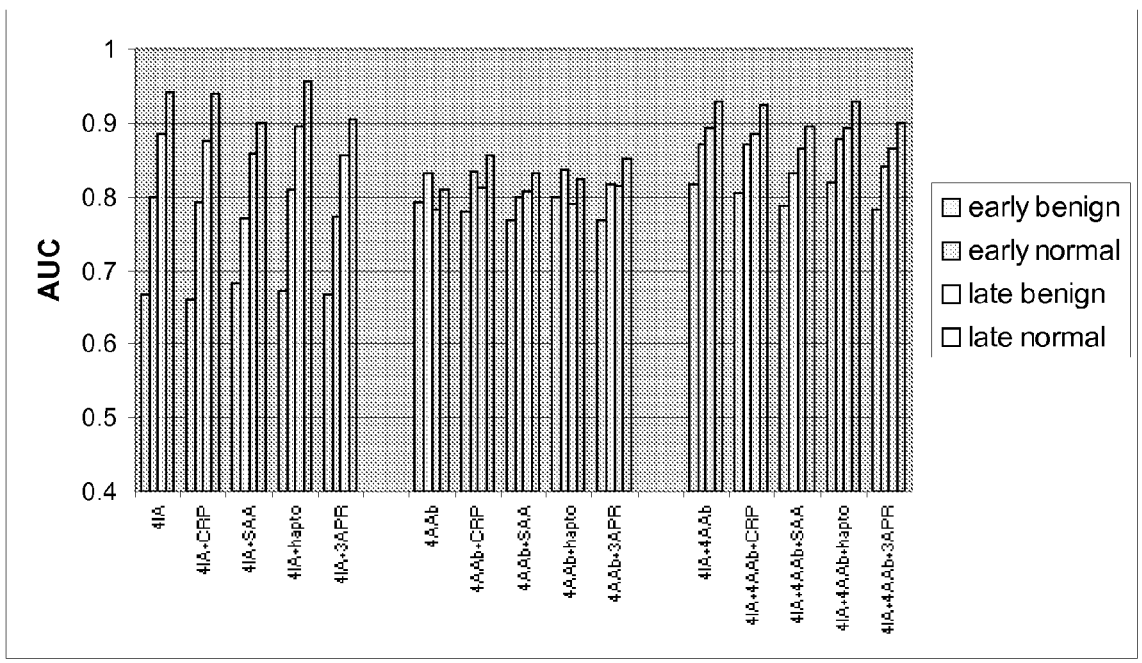
FIG. 9 gives the AUC for a 4 immunoassay, a 4 autoantigen, a 4 immunoassay and one immune response marker (haptoglobin, serum amyloid A, C-reactive protein and apolipoprotein A), a 4 autoantigen and one immune response marker and a 4 immunoassay, 4 autoantigen and one immune response marker panel in differentiating early stage and late stage lung cancer from benign lung disease. For each biomarker panel, four bars are plotted. The first bar represents the AUC for discriminating early stage lung cancer from benign lung disease patients; the second bar represents the AUC for discriminating early stage lung cancer from normals; the third bar represents the AUC for discriminating late stage lung cancer from benign lung disease patients; and the fourth bar represents the AUC for discriminating late stage lung cancer from normals.

The power of these combinations becomes clear in FIG. 9 and Table 36b. Combining the tumor antigens with the immune response markers provides a panel with significantly enhanced stage dependence and a persistent inability to differentiate the early stage lung cancer from benign lung disease (AUC~0.65-0.68). Early stage lung cancer is differentiated from the normal cohort with AUC~0.75-0.8.

Combining the autoantigen biomarkers with the immune response markers provides a panel with greater overall consistency in differentiating cancer from not cancer including early and late stage lung cancer from normal and benign lung disease (FIG. 9). Early stage lung cancer is proficiently differentiated from normals and benign lung disease with AUC~0.75-0.82. AUC for late stage disease and normal or benign lung disease is similar (0.75-0.85) and not quite as good as when using tumor antigens.

The combination of tumor antigens and autoantibodies provides a good panel. The 4/4/0 panel described as 4IA+4Aab in the FIG. 9 differentiates early stage lung cancer from benign lung disease with AUC~0.82. Further combining immune response markers (C-reactive protein, serum amyloid A, or haptoglobin) makes little improvement. Indeed, addition of 3 immune response markers to the 4/4/0 panel actually reduces performance of the panel.

TABLE 36a

| Biomarkers | case group control group | early stage lung cancer | | late stage lung cancer | |
|---|---|---|---|---|---|
|  |  | benign | Normal | benign | normal |
| immune response biomarkers | haptoglobin | 0.56 | 0.65 | 0.69 | 0.76 |
|  | SAA | 0.47 | 0.63 | 0.72 | 0.74 |
|  | CRP | 0.56 | 0.64 | 0.73 | 0.8 |
|  | apoCIII | 0.6 | 0.52 | 0.67 | 0.58 |
| mass spec biomarkers | 4789 | 0.65 | 0.65 | 0.75 | 0.75 |
|  | 11597 | 0.75 | 0.66 | 0.83 | 0.76 |
|  | 2759 | 0.66 | 0.63 | 0.66 | 0.64 |
|  | acn9459 | 0.64 | 0.69 | 0.64 | 0.69 |
| Autoantibodies | tmp21 | 0.6 | 0.64 | 0.59 | 0.63 |
|  | npc111c | 0.59 | 0.58 | 0.61 | 0.6 |
|  | p53 | 0.63 | 0.67 | 0.69 | 0.73 |
|  | mapkapk | 0.68 | 0.7 | 0.71 | 0.74 |
|  | E2-1 | 0.69 | 0.72 | 0.72 | 0.75 |
|  | NYESO | 0.62 | 0.62 | 0.68 | 0.68 |
|  | hdj1 | 0.65 | 0.61 | 0.68 | 0.65 |

TABLE 36a-continued

| Biomarkers | case group control group | early stage lung cancer | | late stage lung cancer | |
|---|---|---|---|---|---|
| | | benign | Normal | benign | normal |
| tumor antigens | tmod | 0.61 | 0.64 | 0.71 | 0.73 |
| | E2 Abnova | 0.58 | 0.58 | 0.61 | 0.61 |
| | E2 Genway | 0.65 | 0.65 | 0.72 | 0.74 |
| | CYFRA | 0.6 | 0.63 | 0.76 | 0.79 |
| | 19-9 | 0.56 | 0.51 | 0.65 | 0.69 |
| | CEA | 0.61 | 0.7 | 0.72 | 0.78 |
| | 15-3 | 0.56 | 0.62 | 0.63 | 0.69 |
| | CA125 | 0.61 | 0.68 | 0.78 | 0.83 |
| | SCC | 0.55 | 0.57 | 0.61 | 0.63 |
| | TPS | 0.6 | 0.64 | 0.72 | 0.75 |
| | proGRP | 0.55 | 0.69 | 0.59 | 0.69 |

TABLE 36b (Tables 36a and 36b have tabulated the AUC values shown in FIGS. 8 and 9)

| Case group control group | early stage lung cancer | | late stage lung cancer | | all lung cancer benign + normal | |
|---|---|---|---|---|---|---|
| | benign | normal | benign | normal | | |
| | AUC | AUC | AUC | AUC | DFI | AUC |
| 4IA | 0.668 | 0.8 | 0.886 | 0.942 | 0.39 | 0.8 |
| 4IA + CRP | 0.66 | 0.792 | 0.875 | 0.938 | 0.38 | 0.8 |
| 4IA + SAA | 0.681 | 0.769 | 0.859 | 0.9 | | 0.81 |
| 4IA + hapto | 0.672 | 0.81 | 0.894 | 0.955 | 0.37 | 0.78 |
| 4IA + 3APR | 0.666 | 0.772 | 0.855 | 0.904 | | 0.78 |
| 4Aab | 0.793 | 0.83 | 0.781 | 0.808 | 0.36 | 0.8 |
| 4Aab + CRP | 0.779 | 0.833 | 0.812 | 0.856 | 0.34 | 0.81 |
| 4Aab + SAA | 0.767 | 0.8 | 0.806 | 0.832 | | 0.81 |
| 4Aab + hapto | 0.798 | 0.836 | 0.789 | 0.824 | | 0.8 |
| 4Aab + 3APR | 0.767 | 0.817 | 0.815 | 0.85 | 0.37 | 0.81 |
| 4IA + 4Aab | 0.816 | 0.87 | 0.893 | 0.93 | 0.28 | 0.87 |
| 4IA + 4Aab + CRP | 0.803 | 0.87 | 0.885 | 0.923 | 0.3 | 0.86 |
| 4IA + 4Aab + SAA | 0.786 | 0.832 | 0.866 | 0.895 | 0.28 | 0.87 |
| 4IA + 4Aab + hapto | 0.818 | 0.877 | 0.892 | 0.929 | 0.33 | 0.84 |
| 4IA + 4Aab + 3APR | 0.782 | 0.841 | 0.865 | 0.9 | 0.34 | 0.84 |

Example 14

Thymosin β4 EIA (Tβ4)

Figure 10:
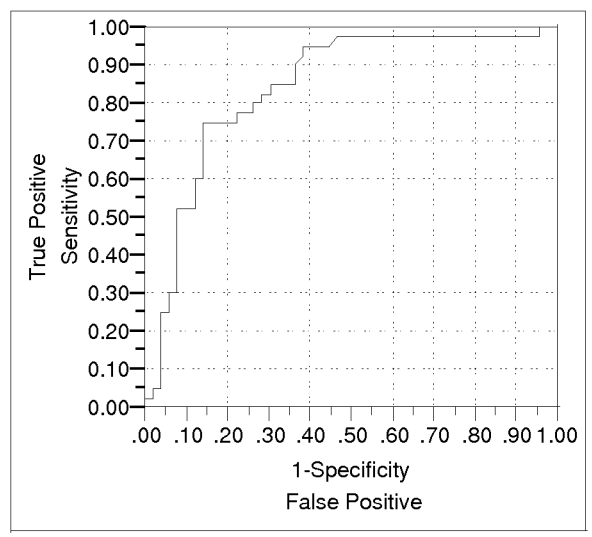
FIG. 10 gives the AUC for Tβ4 assay run on a total of 118 samples (44 lung cancer and 74 non-cancer) containing normal, benign and cancer patient samples. The AUC=0.8393.

The thymosin β4 EIA kit was purchased from ALPCO Diagnostics, (Salem, N.H.). The assays were run according to the manufacturer's instructions. The serum samples were used directly without diluting them. A selected group of 118 samples containing normal, benign and cancer patient samples, were run. The concentrations of the analytes were derived from a 4-parameter logistic curve fit (4PLC) of known standard concentrations as instructed in the manufacturer's protocol. All calculations were performed using the non-linear curve-fitting algorithm provided in the JMP 5.0 statistical package. The AUC obtained for the Tβ4 assay is shown in FIG. 10.

As shown above, Tβ4 by itself was able to discriminate between the diseased and non-diseased groups relatively well. However, at high specificity, its sensitivity is relatively poor as shown in Table 37, below (Specificity=90%, Sensitivity=53%). Here, the improvement in performance of some preferred multi-marker panels when Tβ4 was included in the panels was assessed. Three different groups of marker panels (4IA (CK19, CEA, CA125 and ProGRP), 4Aab (Cyclin E2-1, MAPKAPK3, P53 and NY-ESO-1) and 3APR (Serum amyloid A (pub11597), C-reactive protein, and haptoglobin (suspected to be the 17858 mass)) were used. Table 37 below compares the performance of the panels with and without Tβ4. The AUC and sensitivities at two different specificities (Hspec and Lspec) were also compared. Hspec was set to 90% and Lspec to 70% in order to compare the performance of the panels at high and low specificities respectively.

TABLE 37

Performance of selected panels with and without Tβ4. Hspec was set at 90% and Lspec at 70%.

| Panels | AUC | Sens@Hspec | Sens@Lspec |
|---|---|---|---|
| Tβ4 | 0.84 | 0.53 | 0.83 |
| 4Aab | 0.9 | 0.8 | 0.9 |
| 4Aab + Tβ4 | 0.9 | 0.75 | 0.93 |
| 4IA | 0.86 | 0.72 | 0.78 |
| 4IA + Tβ4 | 0.92 | 0.83 | 0.93 |
| 4APR | 0.64 | 0.38 | 0.5 |
| 4APR + Tβ4 | 0.74 | 0.35 | 0.7 |

As can be seen in the Table 37 above, the best panel without Tβ4 is 4Aab with an AUC of 0.9. The sensitivity of this panel is about 80% and 90% at high and low specificities respectively. However, when Tβ4 is added to this panel, the performance deteriorates slightly at high specificity (Hspec) as the sensitivity drops from 80% to 75%. Since the AUC remains the same, this suggests that the panel is able to compensate for the loss, by gaining some specificity. The 4IA panel, however, shows an overall improvement in both the AUC and the sensitivity at high and low specificity. This suggests that Tβ4 has a synergistic effect on the performance of this panel. As shown in the above Table 37, the AUC improves from 0.86 to 0.92 and the sensitivity at high specificity improves about 10%. At low specificity, the improvement is even greater (ca. 15%). However, although the 3APR panel shows some improvement when Tβ4 is included, it may not be robust enough to be used as clinical assay for discriminating between disease and non-diseased states. The sensitivity of the panel is relatively poor at both high and low specificities.

Thus, the above results suggest that Tβ4 may be used with the 4IA panel as it improves the discriminating power of the panel at both high and low specificities. Such a combined panel would then be more useful than either one used by itself. Close inspections of the performance parameters suggest that the performance of the combined panel is adequate for a relatively robust clinical assay (AUC=0.92, at Specificity=90%, Sensitivity=83%). Moreover, correlation analysis between Tβ4 and the members of the panel shows no correlation at all, confirming the independence of the markers.

One skilled in the art would readily appreciate that the present invention is well adapted to carry out the objects and obtain the ends and advantages mentioned, as well as those inherent therein. The compositions, formulations, methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

What is claimed is:

1. A method of aiding in a diagnosis of a subject suspected of lung cancer, the method comprising the steps of:
   (a) quantifying in a test sample obtained from a subject the amount of biomarkers: anti-p53, anti-NY-ESO-1, pro-GRP, CEA, cytokeratin 19, CA125, and human amyloid protein A;
   (b) comparing the amount of each quantified biomarker to a number of predetermined cutoffs for said biomarker and assigning one of a number of predetermined weighted scores for each biomarker based on said comparison, wherein the assigned weighted score for each biomarker is calculated based on a specificity of the predetermined cutoff nearest to and less than the quantified amount of said biomarker, wherein the specificities of the number of predetermined cutoffs are 0.9, 0.75 and 0.5, and wherein the weighted score is zero if the amount of the biomarker is less than the lowest predetermined cutoff for the biomarker;
   (c) combining the assigned weighted score for each biomarker quantified in step a to obtain a total score for said subject;
   (d) comparing the total score determined in step c with a predetermined total score; and
   (e) determining whether said subject has lung cancer based on the comparison of the total score in step d;
   wherein the Distance from Ideal (DFI) of the biomarkers relative to lung cancer is less than about 0.4.

2. The method of claim 1, further comprising quantifying in the test sample the amount of at least one biomarker selected from the group consisting of: anti-TMP21, anti-HDJ1, anti-NPC1L1C-domain, anti-TMOD1, anti-CAMK1, anti-RGS1, anti-PACSIN1, anti-RCV1, anti-MAPKAPK3, and anti-Cyclin E2.

3. The method of claim 1, further comprising quantifying in the test sample the amount of at least one biomarker selected from the group consisting of: cytokeratin 8, cytokeratin 18, CA19-9, CA15-3, SCC, alpha-1-anti-trypsin, apolipoprotein CIII and thymosin β4.

4. A method of aiding in a diagnosis of a subject suspected of lung cancer, the method comprising the steps of:
   (a) obtaining a value for at least one biometric parameter of a subject;
   (b) comparing the value of the at least one biometric parameter against a predetermined cutoff for each said biometric parameter and assigning a score for each biometric parameter based on said comparison;
   (c) quantifying in a test sample obtained from a subject the amount of biomarkers: anti-p53, anti-NY-ESO-1, pro-GRP, CEA, cytokeratin 19, CA125, and human amyloid protein A;
   (d) comparing the amount of each quantified biomarker to a number of predetermined cutoffs for said biomarker and assigning one of a number of predetermined weighted scores for each biomarker based on said comparison, wherein the assigned weighted score for each biomarker is calculated based on a specificity of the predetermined cutoff nearest to and less than the quantified amount of said biomarker, wherein the specificities of the number of predetermined cutoffs are 0.9, 0.75 and 0.5, and wherein the weighted score is zero if the amount of the biomarker is less than the lowest predetermined cutoff for the biomarker;
   (e) combining the assigned weighted score for each biomarker quantified in step c and the assigned score for each biometric parameter in step b to obtain a total score for said subject;
   (f) comparing the total score determined in step e with a predetermined total score; and
   (g) determining whether said subject has lung cancer based on the comparison of the total score in step f,
   wherein the Distance from Ideal (DFI) of the biomarkers relative to lung cancer is less than about 0.4.

5. The method of claim 4, further comprising quantifying in the test sample the amount of at least one biomarker selected from the group consisting of: anti-TMP21, anti-HDJ1, anti-NPC1L1C-domain, anti-TMOD1, anti-CAMK1, anti-RGS1, anti-PACSIN1, anti-RCV1, anti-MAPKAPK3, and anti-Cyclin E2.

6. The method of claim 4, further comprising quantifying in the test sample the amount of at least one biomarker selected from the group consisting of: cytokeratin 8, cytokeratin 18, CA15-3, SCC, CA19-9, alpha-1-anti-trypsin, apolipoprotein CIII and thymosin β4.

7. The method of claim 4, wherein the biometric parameter is selected from the group consisting of: the subject's smoking history, age, carcinogen exposure, and gender.

8. The method of claim 7, wherein the biometric parameter is pack-years of smoking.

9. The method of claim 4, wherein step b comprises comparing the value of each biometric parameter against a number of predetermined cutoffs for said biometric parameter and assigning one of a number of possible scores for each said biometric parameter based on said comparison.

10. The method of claim 4, wherein the biometric parameter is pack-years of smoking.

11. The method of claim 1, wherein the method comprises quantifying the amount of seven or more biomarkers.

12. The method of claim 4, wherein the method comprises quantifying the amount of seven or more biomarkers.

* * * * *

SEQUENCE LISTING

<160> NUMBER OF SEQ ID NOS: 10

<210> SEQ ID NO 1
<211> LENGTH: 296
<212> TYPE: PRT
<213> ORGANISM: Homo sapiens

<400> SEQUENCE: 1

```
Met Ser Lys Glu Val Trp Leu Asn Met Leu Lys Lys Glu Ser Arg Tyr
1               5                   10                  15

Val His Asp Lys His Phe Glu Val Leu His Ser Asp Leu Glu Pro Gln
            20                  25                  30

Met Arg Ser Ile Leu Leu Asp Trp Leu Leu Glu Val Cys Glu Val Tyr
        35                  40                  45

Thr Leu His Arg Glu Thr Phe Tyr Leu Ala Gln Asp Phe Phe Asp Arg
    50                  55                  60

Phe Met Leu Thr Gln Lys Asp Ile Asn Lys Asn Met Leu Gln Leu Ile
65                  70                  75                  80

Gly Ile Thr Ser Leu Phe Ile Ala Ser Lys Leu Glu Glu Ile Tyr Ala
                85                  90                  95

Pro Lys Leu Gln Glu Phe Ala Tyr Val Thr Asp Gly Ala Cys Ser Glu
            100                 105                 110

Glu Asp Ile Leu Arg Met Glu Leu Ile Ile Leu Lys Ala Leu Lys Trp
        115                 120                 125

Glu Leu Cys Pro Val Thr Ile Ile Ser Trp Leu Asn Leu Phe Leu Gln
130                 135                 140

Val Asp Ala Leu Lys Asp Ala Pro Lys Val Leu Leu Pro Gln Tyr Ser
145                 150                 155                 160

Gln Glu Thr Phe Ile Gln Ile Ala Gln Leu Leu Asp Leu Cys Ile Leu
                165                 170                 175

Ala Ile Asp Ser Leu Glu Phe Gln Tyr Arg Ile Leu Thr Ala Ala Ala
            180                 185                 190

Leu Cys His Phe Thr Ser Ile Glu Val Val Lys Lys Ala Ser Gly Leu
        195                 200                 205

Glu Trp Asp Ser Ile Ser Glu Cys Val Asp Trp Met Val Pro Phe Val
    210                 215                 220

Asn Val Val Lys Ser Thr Ser Pro Val Lys Leu Lys Thr Phe Lys Lys
225                 230                 235                 240

Ile Pro Met Glu Asp Arg His Asn Ile Gln Thr His Thr Asn Tyr Leu
                245                 250                 255

Ala Met Leu Glu Glu Val Asn Tyr Ile Asn Thr Phe Arg Lys Gly Gly
            260                 265                 270

Gln Leu Ser Pro Val Cys Asn Gly Gly Ile Met Thr Pro Pro Lys Ser
        275                 280                 285

Thr Glu Lys Pro Pro Gly Lys His
    290                 295
```

<210> SEQ ID NO 2
<211> LENGTH: 374
<212> TYPE: PRT
<213> ORGANISM: Homo sapiens

```
<400> SEQUENCE: 2

Met Ser Arg Arg Ser Arg Leu Gln Ala Lys Gln Gln Pro Gln Pro
1               5                   10                  15

Ser Gln Thr Glu Ser Pro Gln Glu Ala Gln Ile Ile Gln Ala Lys Lys
            20                  25                  30

Arg Lys Thr Thr Gln Asp Val Lys Arg Arg Glu Val Thr Lys
                35                  40                  45

Lys His Gln Tyr Glu Ile Arg Asn Cys Trp Pro Pro Val Leu Ser Gly
        50                  55                  60

Gly Ile Ser Pro Cys Ile Ile Ile Glu Thr Pro His Lys Glu Ile Gly
65                  70                  75                  80

Thr Ser Asp Phe Ser Arg Phe Thr Asn Tyr Arg Phe Lys Asn Leu Phe
                85                  90                  95

Ile Asn Pro Ser Pro Leu Pro Asp Leu Ser Trp Gly Cys Ser Lys Glu
            100                 105                 110

Val Trp Leu Asn Met Leu Lys Lys Glu Ser Arg Tyr Val His Asp Lys
        115                 120                 125

His Phe Glu Val Leu His Ser Asp Leu Glu Pro Gln Met Arg Ser Ile
    130                 135                 140

Leu Leu Asp Trp Leu Leu Glu Val Cys Glu Val Tyr Thr Leu His Arg
145                 150                 155                 160

Glu Thr Phe Tyr Leu Ala Gln Asp Phe Phe Asp Arg Phe Met Leu Thr
                165                 170                 175

Gln Lys Asp Ile Asn Lys Asn Met Leu Gln Leu Ile Gly Ile Thr Ser
            180                 185                 190

Leu Phe Ile Ala Ser Lys Leu Glu Glu Ile Tyr Ala Pro Lys Leu Gln
        195                 200                 205

Glu Phe Ala Tyr Val Thr Asp Gly Ala Cys Ser Glu Glu Asp Ile Leu
    210                 215                 220

Arg Met Glu Leu Ile Ile Leu Lys Ala Leu Lys Trp Glu Leu Cys Pro
225                 230                 235                 240

Val Thr Ile Ile Ser Trp Leu Asn Leu Phe Leu Gln Val Asp Ala Leu
                245                 250                 255

Lys Asp Ala Pro Lys Val Leu Leu Pro Gln Tyr Ser Gln Glu Thr Phe
            260                 265                 270

Ile Gln Ile Ala Gln Leu Leu Asp Leu Cys Ile Leu Ala Ile Asp Ser
        275                 280                 285

Leu Glu Phe Gln Tyr Arg Ile Leu Thr Ala Ala Leu Cys His Phe
    290                 295                 300

Thr Ser Ile Glu Val Val Lys Lys Ala Ser Gly Leu Glu Trp Asp Ser
305                 310                 315                 320

Ile Ser Glu Cys Val Asp Trp Met Val Pro Phe Val Asn Val Val Lys
                325                 330                 335

Ser Thr Ser Pro Val Lys Leu Lys Thr Phe Lys Lys Ile Pro Met Glu
            340                 345                 350

Asp Arg His Asn Ile Gln Thr His Thr Asn Tyr Leu Ala Met Leu Cys
        355                 360                 365

Met Ile Ser Ser His Val
    370

<210> SEQ ID NO 3
<211> LENGTH: 38
<212> TYPE: PRT
<213> ORGANISM: Homo sapiens
```

```
<400> SEQUENCE: 3

Cys Glu Glu Val Asn Tyr Ile Asn Thr Phe Arg Lys Gly Gly Gln Leu
1               5                   10                  15

Ser Pro Val Cys Asn Gly Gly Ile Met Thr Pro Pro Lys Ser Thr Glu
            20                  25                  30

Lys Pro Pro Gly Lys His
            35

<210> SEQ ID NO 4
<211> LENGTH: 37
<212> TYPE: PRT
<213> ORGANISM: Homo sapiens

<400> SEQUENCE: 4

Glu Glu Val Asn Tyr Ile Asn Thr Phe Arg Lys Gly Gly Gln Leu Ser
1               5                   10                  15

Pro Val Cys Asn Gly Gly Ile Met Thr Pro Pro Lys Ser Thr Glu Lys
            20                  25                  30

Pro Pro Gly Lys His
            35

<210> SEQ ID NO 5
<211> LENGTH: 19
<212> TYPE: PRT
<213> ORGANISM: Homo sapiens

<400> SEQUENCE: 5

Cys Asn Gly Gly Ile Met Thr Pro Pro Lys Ser Thr Glu Lys Pro Pro
1               5                   10                  15

Gly Lys His

<210> SEQ ID NO 6
<211> LENGTH: 103
<212> TYPE: PRT
<213> ORGANISM: Homo sapiens

<400> SEQUENCE: 6

Ser Phe Phe Ser Phe Leu Gly Glu Ala Phe Asp Gly Ala Arg Asp Met
1               5                   10                  15

Trp Arg Ala Tyr Ser Asp Met Arg Glu Ala Asn Tyr Ile Gly Ser Asp
            20                  25                  30

Lys Tyr Phe His Ala Arg Gly Asn Tyr Asp Ala Ala Lys Arg Gly Pro
        35                  40                  45

Gly Gly Ala Trp Ala Ala Glu Val Ile Ser Asp Ala Arg Glu Asn Ile
    50                  55                  60

Gln Arg Phe Phe Gly His Asp Ala Glu Asp Ser Leu Ala Asp Gln Ala
65                  70                  75                  80

Ala Asn Glu Trp Gly Arg Ser Gly Lys Asp Pro Asn His Phe Arg Pro
                85                  90                  95

Ala Gly Leu Pro Glu Lys Tyr
            100

<210> SEQ ID NO 7
<211> LENGTH: 103
<212> TYPE: PRT
<213> ORGANISM: Homo sapiens
```

```
<400> SEQUENCE: 7

Ser Phe Phe Ser Phe Leu Gly Glu Ala Phe Asp Gly Ala Arg Asp Met
1               5                   10                  15

Trp Arg Ala Tyr Ser Asp Met Arg Glu Ala Asn Tyr Ile Gly Ser Asp
            20                  25                  30

Lys Tyr Phe His Ala Arg Gly Asn Tyr Asp Ala Ala Lys Arg Gly Pro
        35                  40                  45

Gly Gly Ala Trp Ala Ala Glu Val Ile Ser Ala Arg Glu Asn Ile
    50                  55                  60

Gln Arg Phe Phe Gly His Gly Ala Glu Asp Ser Leu Ala Asp Gln Ala
65              70                  75                  80

Ala Asn Glu Trp Gly Arg Ser Gly Lys Asp Pro Asn His Phe Arg Pro
                85                  90                  95

Ala Gly Leu Pro Glu Lys Tyr
            100

<210> SEQ ID NO 8
<211> LENGTH: 79
<212> TYPE: PRT
<213> ORGANISM: Homo sapiens

<400> SEQUENCE: 8

Ser Glu Ala Glu Asp Ala Ser Leu Leu Ser Phe Met Gln Gly Tyr Met
1               5                   10                  15

Lys His Ala Thr Lys Thr Ala Lys Asp Ala Leu Ser Ser Val Gln Glu
            20                  25                  30

Ser Gln Val Ala Gln Ala Arg Gly Trp Val Thr Asp Gly Phe Ser
        35                  40                  45

Ser Leu Lys Asp Tyr Trp Ser Thr Val Lys Asp Lys Phe Ser Glu Phe
    50                  55                  60

Trp Asp Leu Asp Pro Glu Val Arg Pro Thr Ser Ala Val Ala Ala
65              70                  75

<210> SEQ ID NO 9
<211> LENGTH: 42
<212> TYPE: PRT
<213> ORGANISM: Homo sapiens

<400> SEQUENCE: 9

Leu Glu Ala Ile Pro Met Ser Ile Pro Pro Glu Val Lys Phe Asn Glu
1               5                   10                  15

Pro Phe Val Phe Leu Met Ile Asp Gln Asn Thr Lys Ser Pro Leu Phe
            20                  25                  30

Met Gly Lys Val Val Asn Pro Thr Gln Lys
        35                  40

<210> SEQ ID NO 10
<211> LENGTH: 24
<212> TYPE: PRT
<213> ORGANISM: Homo sapiens

<400> SEQUENCE: 10

Asp Ala His Lys Ser Glu Val Ala His Arg Phe Lys Asp Leu Gly Glu
1               5                   10                  15

Glu Asn Phe Lys Ala Leu Val Leu
            20
```